(12) United States Patent
Apuy et al.

(10) Patent No.: US 8,551,963 B2
(45) Date of Patent: Oct. 8, 2013

(54) IMIDAZOLOTHIAZOLE COMPOUNDS AND METHODS OF USE THEREOF

(75) Inventors: Julius L. Apuy, San Diego, CA (US); Darren E. Insko, San Diego, CA (US); Joyce J. James, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 13/127,978

(22) PCT Filed: Nov. 5, 2009

(86) PCT No.: PCT/US2009/063367
§ 371 (c)(1),
(2), (4) Date: Oct. 18, 2011

(87) PCT Pub. No.: WO2010/054058
PCT Pub. Date: May 14, 2010

(65) Prior Publication Data
US 2012/0070410 A1    Mar. 22, 2012

Related U.S. Application Data

(60) Provisional application No. 61/112,146, filed on Nov. 6, 2008.

(51) Int. Cl.
*C07D 513/00* (2006.01)
*A01N 43/78* (2006.01)
*A01N 57/00* (2006.01)
*A01N 43/66* (2006.01)
*A01N 43/04* (2006.01)
*A01N 45/00* (2006.01)
*A61K 31/425* (2006.01)
*A61K 31/66* (2006.01)
*A61K 31/70* (2006.01)
*A61K 31/553* (2006.01)
*A61K 31/50* (2006.01)
*A61K 31/497* (2006.01)

(52) U.S. Cl.
USPC ............... 514/32; 514/49; 514/133; 514/151; 514/171; 514/252.01; 514/254.06; 514/366; 548/151

(58) Field of Classification Search
None
See application file for complete search history.

(56) References Cited

FOREIGN PATENT DOCUMENTS

| WO | WO 2007/109120 | * | 9/2007 |
| WO | WO 2007/109210 | * | 9/2007 |

* cited by examiner

*Primary Examiner* — Anna Pagonakis
(74) *Attorney, Agent, or Firm* — Jones Day

(57) ABSTRACT

Compounds, compositions and methods are provided for modulating the activity of receptor kinases and for the treatment, prevention, or amelioration of one or more symptoms of disease or disorder mediated by receptor kinases.

5 Claims, 13 Drawing Sheets

IMIDAZOLOTHIAZOLE COMPOUNDS AND METHODS OF USE THEREOF

RELATED APPLICATIONS

This application is a National stage of International Application No. PCT/US2009/063367, filed Nov. 5, 2009 which claims priority to U.S. provisional application Ser. No. 61/112,146, filed Nov. 6, 2008, entitled "Imidazolothiazole Compounds And Methods Of Use Thereof". The disclosures of the above referenced applications are incorporated by reference herein in their entireties.

FIELD

Small molecule compounds, compositions and methods for treating disease are provided. The compounds provided are modulators of activity of enzymes, such as kinases, and are useful in the treatment, prevention, and/or amelioration of a disease or disorder related to enzyme activity, or one or more symptoms thereof.

BACKGROUND

Protein kinases (PKs) are enzymes that catalyze the phosphorylation of hydroxy groups on tyrosine, serine and threonine residues of proteins. Protein kinases, and in particular the receptor protein tyrosine kinase (RTK) family of protein kinases, act primarily as growth factor receptors and play a central role in signal transduction pathways regulating a number of cellular functions, such as cell cycle, cell growth, cell differentiation and cell death. Aberrant or excessive activity or the disregulation of activity of receptor protein tyrosine kinase (RPTK) has been observed in many disease states including benign and malignant proliferative disorders as well as inflammatory disorders and immune system disorders that result from inappropriate activation of the immune system to cause, for example, autoimmune diseases.

It is additionally possible that inhibitors of certain kinases may have utility in the treatment of diseases when the kinase is not misregulated, but is nonetheless essential for maintenance of the disease state. In such cases, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994)).

Finally, while overactivation of RTK signaling pathways is often the underlying mechanism for cancer, impaired deactivation of RTKs such as the impaired down-regulation of RTKs via ligand-induced endocytosis or impaired negative feedback loops, may also be the cause of some malignancies. Another strategy for use of the molecules discussed herein therefore is to repair and promote any existing mechanism for down-regulating RTKs.

In view of the large number of protein kinase inhibitors and the multitude of PK-mediated proliferative, inflammatory and immune function diseases, there is an ever-existing need to provide compounds that are useful as PK inhibitors and thus in the treatment of PK related diseases, as discussed herein.

SUMMARY

In certain embodiment, compounds for use in medical treatment, pharmaceutical compositions and methods for modulating the activity, binding or subcellular distribution of kinases are provided. In one embodiment, a compound provided herein has formula:

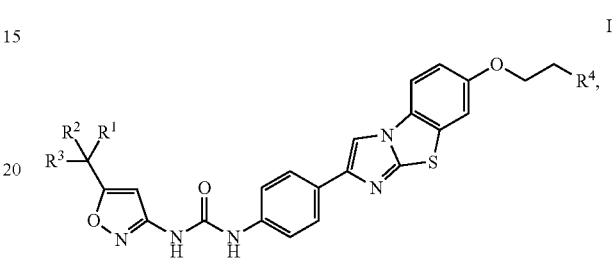

I or is a pharmaceutically acceptable salt, solvate, hydrate or prodrug thereof, wherein $R^1$, $R^2$ and $R^3$ are selected as follows:

i) $R^1$ and $R^2$ are each selected from $-CH_3$, and $-CH_2OH$; and $R^3$ is selected from $-CH_3$, $-CH(OH)_2$, $-CHO$, $-CH_2OH$,

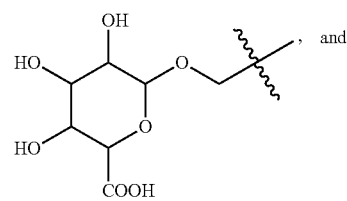

, and

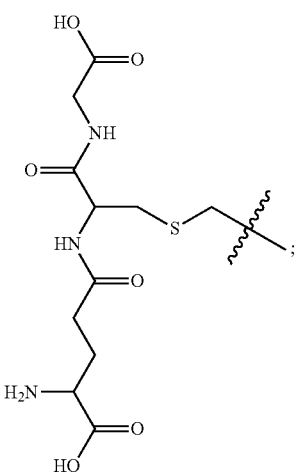

;

or ii) $R^1$, $R^2$ and $R^3$ are each selected from $-CH_3$ and $-COOH$; and $R^4$ is selected from:
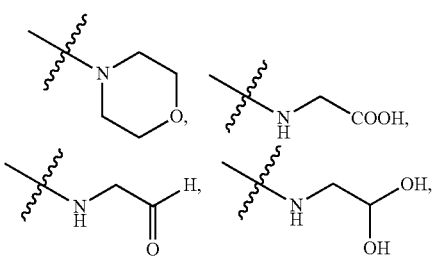
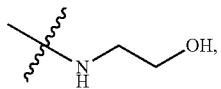
with a proviso that the compound is not N-(5-tert-butyl-isoxazol-3-yl)-N'-{4-[7-(2-morpholin-4-yl-ethoxy)imidazo[2,1-b][1,3]benzothiazol-2-yl]phenyl}urea.
In one embodiment, the compounds provided herein are selected from:
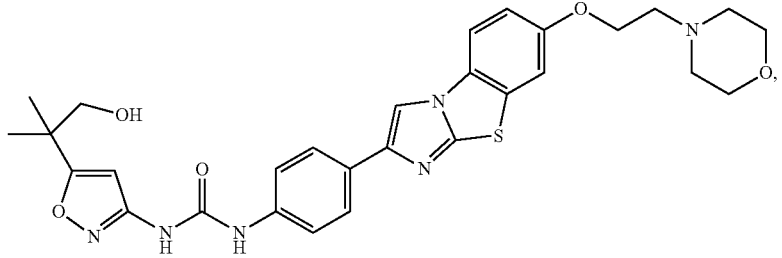
I-1
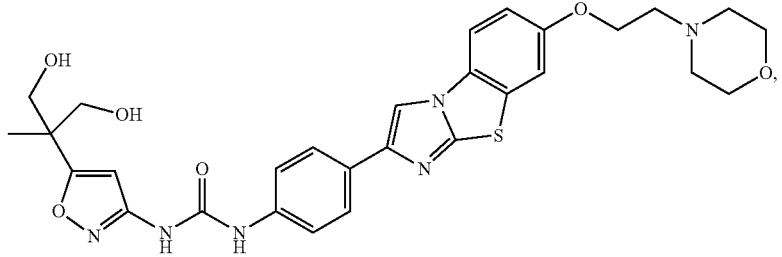
I-1a
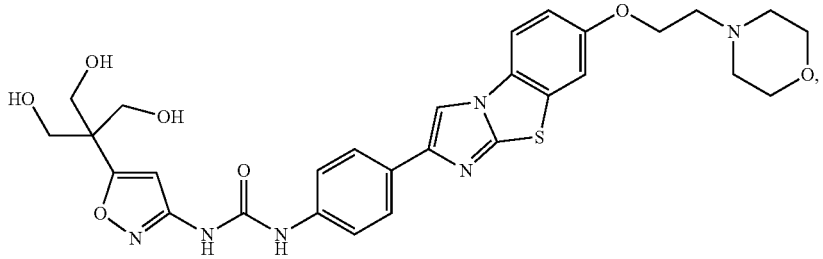
I-1b
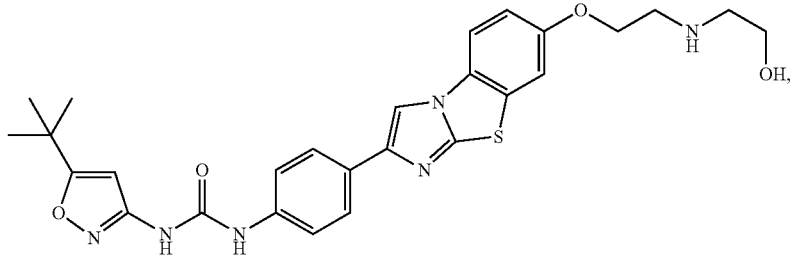
I-2

-continued
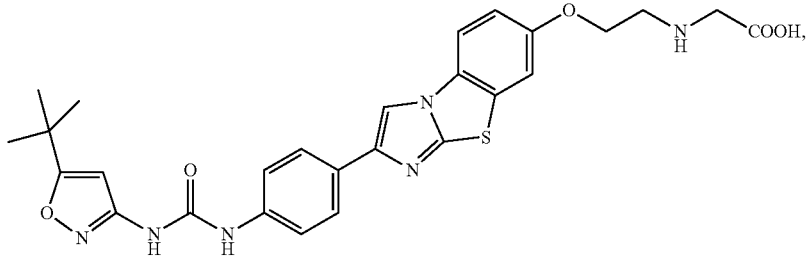
I-3
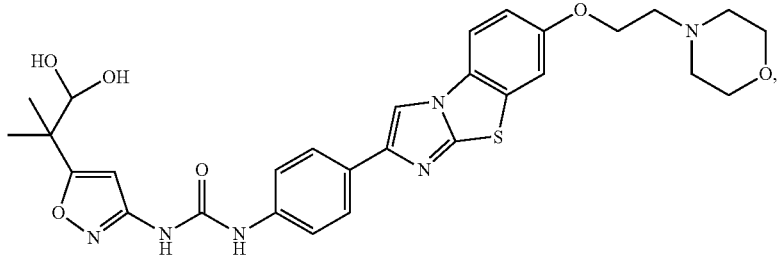
I-4
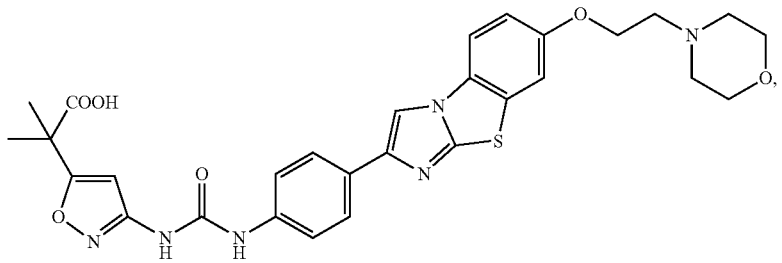
I-5
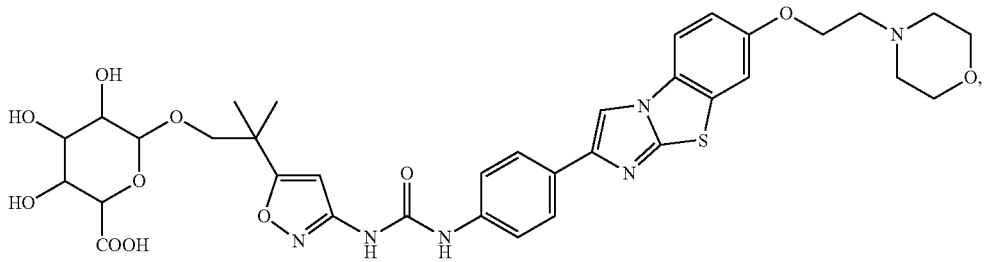
I-6
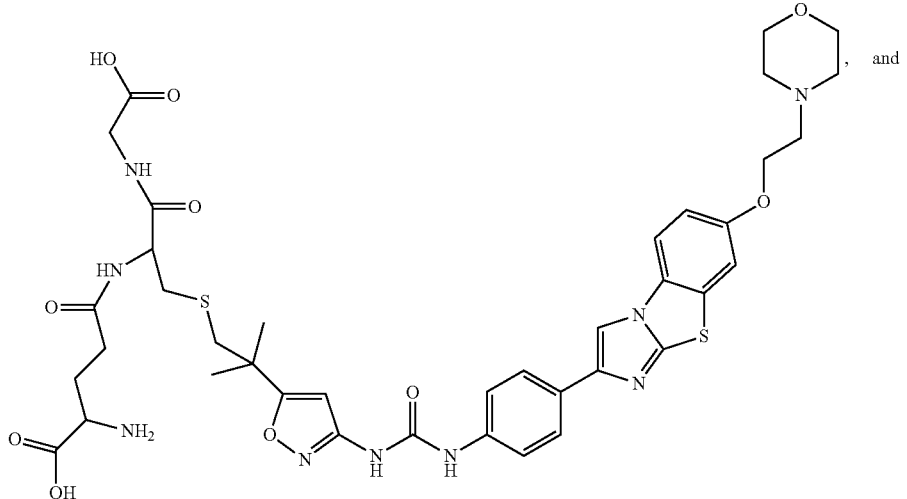
I-7
and

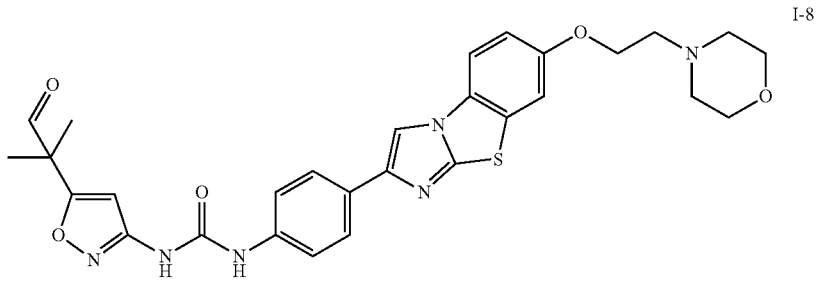 [SMILES: CC(C)(C=O)c1cc(NC(=O)Nc2ccc(-c3cn4c(n3)sc3cc(OCCN5CCOCC5)ccc34)cc2)no1]

or a pharmaceutically acceptable salt, solvate, hydrate or prodrug thereof.

In one embodiment, the compound provided herein is a glucuronidyloxy derivative of N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt, solvate, hydrate or prodrug thereof.

In one embodiment, the compound provided herein is a glutathionyl derivative of N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt, solvate, hydrate or prodrug thereof.

In one embodiment, the compound provided herein is a pharmaceutically acceptable salt of the compound of formula I-1, I-1a, I-1b, I-2, I-3, I-4, I-5, I-6, I-7 or I-8. In another embodiment, the compound provided herein is a solvate of the compound of formula I-1, I-1a, I-1b, I-2, I-3, I-4, I-5, I-6, I-7 or I-8. In yet another embodiment, the compound provided herein is a hydrate of compound of formula I-1, I-1a, I-1b, I-3, I-4, I-5, I-6, I-7 or I-8.

Such compounds or their salts or solvates can bind to one or more kinases with high affinity and modulate their activity. In certain embodiments, such compounds exhibit an $EC_{50}$, $IC_{50}$ or binding affinity of less than 1 μM, and in certain embodiments, less than about 0.5 μM, 250 nM, 100 nM or 50 nM. In one aspect, the compounds or their salts or solvates provided herein are selective for a specific kinase, or a specific subset of kinases, i.e. are at least 5, 10, or in another aspect, at least 20, 50, 100 times more potent, as measured by any of the in vitro assays known to one of skill in the art, in binding to the desired kinase(s) compared to a non preferred kinase or kinases. In one aspect, the compounds selectively inhibit the desired kinase(s) without significant effect on the non desired kinase(s).

Also provided are pharmaceutical compositions formulated for administration by an appropriate route and means containing effective concentrations of one or more of the compounds provided herein, or pharmaceutically acceptable salts, solvates, hydrates and prodrugs thereof, and optionally comprising at least one pharmaceutical carrier, excipient, vehicle, or diluent. The pharmaceutical compositions can further optionally comprise a binder, disintegrating agent, lubricant, glidant, sweetening agent, flavoring agent or a combination thereof.

Such pharmaceutical compositions comprise amounts effective for the treatment, prevention, or amelioration of diseases or disorders that are modulated or otherwise affected by protein kinases (PK related diseases) or one or more symptoms or causes thereof. Further such pharmaceutical compositions can deliver amounts effective for the treatment, prevention, or amelioration of diseases or disorders that are modulated or otherwise affected by protein kinases (PK related diseases) or one or more symptoms or causes thereof.

Such diseases or disorders are discussed including, but not limited to, diseases or disorders that are modulated or otherwise affected by protein kinases (PK related diseases) or one or more symptoms or causes thereof. Certain embodiments herein provide methods for the treatment, prevention or management of diseases or disorders including, but not limited to, proliferative diseases, including nonmalignant and malignant proliferative diseases, such as solid tumors and hematologic malignancies, fibroproliferative disorders, inflammatory diseases or disorders related to immune dysfunction, infectious diseases, and/or diseases or disorders that can be treated, prevented or managed by modulating the activity, binding or sub-cellular distribution of kinases, wherein such methods comprise administering to a subject, e.g., a human, in need of such treatment, prevention or management a therapeutically and prophylactically effective amount of a compound provided herein. Such diseases or disorders are further described herein.

Also contemplated herein are combination therapies using one or more compounds or compositions provided herein, or a pharmaceutically acceptable salt, solvate, hydrate or prodrug thereof, in combination with other pharmaceutically active agents for the treatment of the diseases and disorders described herein.

In one embodiment, such additional pharmaceutical agents include one or more of the following; anti-cancer agents, anti-inflammatory agents and anti-emetics.

The compound or composition provided herein, or pharmaceutically acceptable salt, solvate, hydrate or prodrug thereof, may be administered simultaneously with, prior to, or after administration of one or more of the above agents. Pharmaceutical compositions containing a compound provided herein and one or more of the above agents are also provided.

The compound provided herein may also be provided as a prodrug, which is a functional derivative of a compound, for example, of formula I-1, I-1a, I-1b, I-2, I-3, I-4, I-5, I-6, I-7 or I-8 and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv.*

Drug. Delivery Rev. 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems,"Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In certain embodiments, provided herein are methods of treating diseases or disorders that are modulated or otherwise affected by protein kinases (PK related diseases) or one or more symptoms or causes thereof by administering Compound I-1, I-1a, I-1b, I-2, I-3, I-4, I-5, I-6, I-7 or I-8 or a salt, solvate, hydrate or prodrug thereof. In another embodiment, the methods comprise administering a substantially pure Compound I-1, I-1a, I-1b, I-2, I-3, I-4, I-5, I-6, I-6, I-7 or I-8.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the diseases or disorders.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION

A. Definitions

Figure 1:
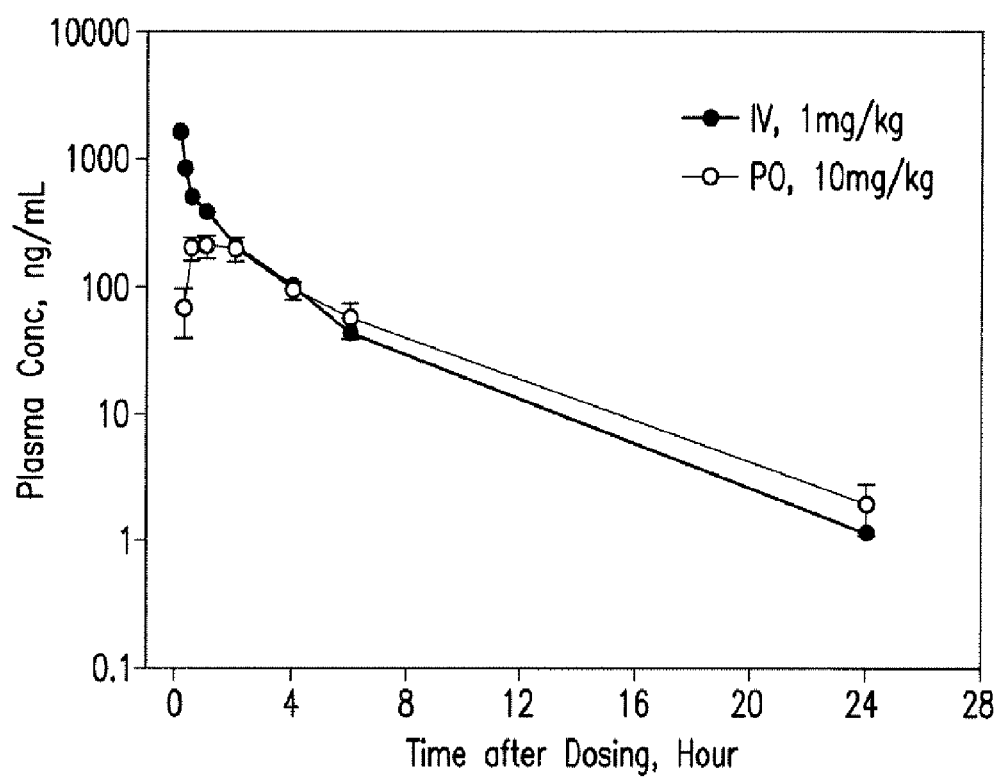
FIG. 1: provides rat IV and oral plasma concentration-time curves for compound I-1.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

The term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma cancers, lung cancers, breast cancers, colorectal cancers, prostate cancers, gastric cancers, esophageal cancers, colon cancers, pancreatic cancers, ovarian cancers, and hematologic malignancies.

The term "hematologic malignancy" refers to cancer of the bone marrow derived cells including the blood, bone marrow and lymphatic tissue. Examples of hematological malignancies include, for instance, myelodysplasia, lymphomas, leukemias, lymphomas (non-Hodgkin's lymphoma), Hodgkin's disease (also called Hodgkin's lymphoma), and myeloma, such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

The term "leukemia" refers to malignant neoplasms of the blood-forming tissues either of the lymphoid or myeloid lineage, including, but not limited to, chronic lymphocytic leukemia, chronic myelocytic leukemia, acute lymphoblastic leukemia, acute myeloid leukemia and acute myeloblastic leukemia. The leukemia can be relapsed, refractory, or resistant to conventional therapy.

The term "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of parts of chromosomes 15 and 17.

The term "acute lymphocytic leukemia," "acute lymphoblastic leukemia," or "ALL" refers to a malignant disease caused by the abnormal growth and development of early nongranular white blood cell or lymphocytes.

The term "T-cell leukemia" refers to a disease in which certain cells of the lymphoid system called T lymphocytes or T cells are malignant. T cells are white blood cells that normally can attack virus-infected cells, foreign cells, and cancer cells; and produce substances that regulate the immune response.

The term "relapsed" refers to a situation where a subject or a mammal, which has had a remission of cancer after therapy has a return of cancer cells.

The term "refractory or resistant" refers to a circumstance where a subject or a mammal, even after intensive treatment, has residual cancer cells in his body.

The term "anticancer agent" is meant to include anti-proliferative agents and chemotherapeutic agents, including, but not limited to, antimetabolites (e.g., pyrimidine analogs including but not limited to 5-fluoro uracil, floxuridine, capecitabine, clofarabine; fludarabine, 5-azacytidine; cytosine arabinoside (including but not limited to cytarabine, Ara-C, HDAC (high dose cytarabine)); folic acid analogs including but not limited to methotrexate; antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitibine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, doxorubicin, daunorubicin (including but not limited to, daunomycin, rubidomycin, or cerubidine), and mitoxantrone), topoisomerase inhibitors (e.g., etoposide and camptothecins), purine anatagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monocolonal antibodies (e.g., gemtuzumab ozogamicin, alemtuzumab, rituximab, and yttrium-90-ibritumomab tiuxetan), immunomodulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthemia and cryotherapy, and agents to attenuate any adverse effects (e.g., antiemetics).

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired. As used herein, the term "drug resistance" is meant to include imatinib-resistance, dasatinib-resistance, nilotinib-resistance, erlotinib-resistance, gefitinib-resistance, sunitinib-resistance, sorafenib-resistance, and/or lapatinib-resistance.

The term "subject" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject. "$IC_{50}$" refers to an amount, concentration or dosage of a particular test compound that achieves a 50% inhibition of a maximal response, such as cell growth or proliferation measured via any the in vitro or cell based assay described herein.

As used herein and unless otherwise specified, the term "pharmaceutically acceptable salts" refers to salts prepared from one of the following pharmaceutically acceptable acids: hydrochloric acid; hydrobromic acid; sulfuric acid; methanesulfonic acid; ethanesulfonic acid; ethane-1,2-disulfonic acid; benzenesulfonic acid; p-toluenesulfonic acid; naphthalene-2-sulfonic acid; adipic acid; fumaric acid; glycolic acid; hippuric acid; maleic acid; phosphoric acid; and DL-tartaric acid. Acid addition salts can be obtained, e.g., by contacting the neutral form of a compound provided herein with a sufficient amount of the desired acid, e.g., either neat or in a suitable solvent. As solids, salts can exist in crystalline or amorphous modifications, or mixtures thereof. Examples of methods for preparing and analyzing such salts are provided, e.g., in *Handbook of Pharmaceutical Salts: Properties, Selection and Use*, P. H. Stahl and C. G. Wermuth, Eds., (2002), Wiley, Weinheim. See also A. T. M. Serajuddin, Adv. Drug Deliv. Rev. (2007) 59: 603-16; P. L. Gould, Int. J. Pharm. (1986) 33: 201-17.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "prodrug" means a compound that, upon in vivo administration, is metabolized by one or more steps or processes or otherwise converted to the biologically, pharmaceutically or therapeutically active form of the compound.

As used herein and unless otherwise indicated, the term "glutathionyl derivative" means a compound bearing a γ-glutamylcysteylglycine group.

As used herein and unless otherwise indicated, the term "glucuronide" means a compound bearing a glycoside of glucuronic acid.

The terms "substantially pure", "pure" or "purified" with respect to a compound provided herein include a composition that includes at least 75%, 80%, 85%, 90%, 95%, 96%, 97%, 98%, 99%, 99.5%, 99.8%, 99.9% to 100% by weight, of the compound, the remainder comprising other chemical species. The purity of the compounds provided herein can be determined by standard methods of analysis, such as thin layer chromatography (TLC), gel electrophoresis, high performance liquid chromatography (HPLC) and mass spectrometry (MS), used by those of skill in the art to assess such purity. In certain embodiments, the compounds are sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Similarly, the term "isolated" with respect to a compound includes a composition that includes at least 75%, 80%, 85%, 90%, 95%, 98%, 99% to 100% by weight, of the compound, the remainder comprising other chemical species.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

As used herein, Compound IA or AC220 refers to N-(5-tert-butyl-isoxazol-3-yl)-N'-{4-[7-(2-morpholin-4-yl-ethoxy)imidazo[2,1-b][1,3]benzothiazol-2-yl]phenyl}urea and has the following formula:

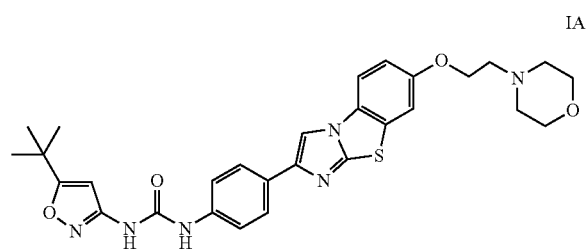 [SMILES: CC(C)(C)c1cc(NC(=O)Nc2ccc(-c3cn4c(n3)sc3cc(OCCN5CCOCC5)ccc34)cc2)no1]

IA

In the description herein, if there is any discrepancy between a chemical name and chemical structure, the structure preferably controls.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, moderate heating is intended to mean maintaining a temperature of from about 30° C. to about 150° C., or up to the boiling point of the reaction solvent, or up to 10° C. above the boiling point of the reaction solvent if the reaction is conducted in a sealed reaction vessel.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

In one embodiment, a compound provided herein has formula:

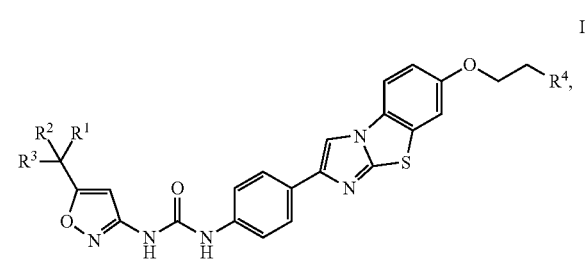

I or is a pharmaceutically acceptable salt, solvate, hydrate or prodrug thereof, wherein $R^1$, $R^2$ and $R^3$ are selected as follows:

i) $R^1$ and $R^2$ are each selected from —$CH_3$ and —$CH_2OH$; and $R^3$ is selected from —$CH_3$, —$CH(OH)_2$, —$CH_2OH$,

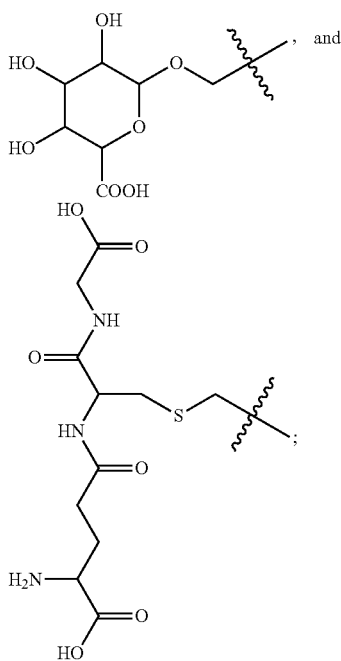

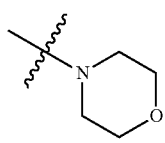

or ii) $R^1$, $R^2$ and $R^3$ are each selected from —$CH_3$ and —COOH; and $R^4$ is selected as follows:

i) $R^4$ is

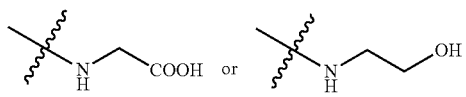 [SMILES: *NCC(=O)O ; *NCCO]

when at least one of $R^1$, $R^2$ or $R^3$ is other than —$CH_3$; or ii) $R^4$ is when $R^1$, $R^2$ and $R^3$ are each —$CH_3$.

In one embodiment, the compounds provided herein have formula:

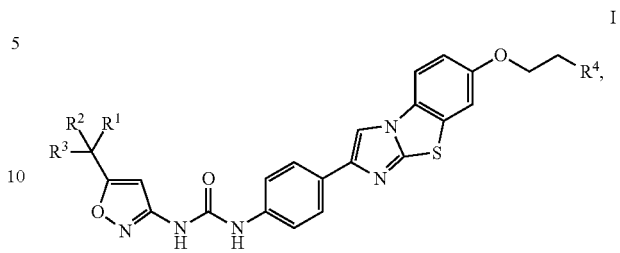

I or a pharmaceutically acceptable salt, solvate, hydrate thereof, wherein $R^1$, $R^2$ and $R^3$ are selected as follows:

i) $R^1$ and $R^2$ are each selected from —$CH_3$ or —$CH_2OH$; and $R^3$ is selected from —$CH_3$, —$CH(OH)_2$, —$CH_2OH$ and

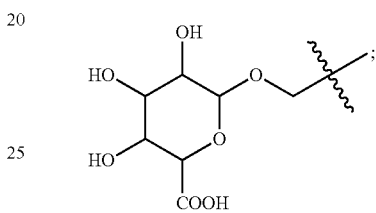

or ii) $R^1$, $R^2$ and $R^3$ are each selected from —$CH_3$ and —COOH; and $R^4$ is selected as follows:

i) $R^4$ is

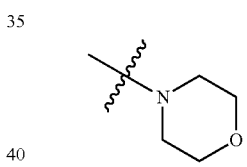

when at least one of $R^1$, $R^2$ or $R^3$ is other than —$CH_3$; or ii) $R^4$ is

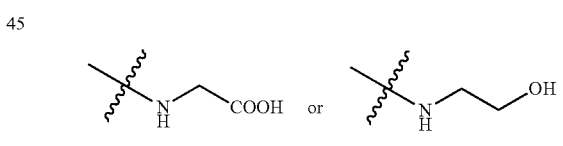

when $R^1$, $R^2$ and $R^3$ are each —$CH_3$.

In one embodiment, the compounds provided herein are:

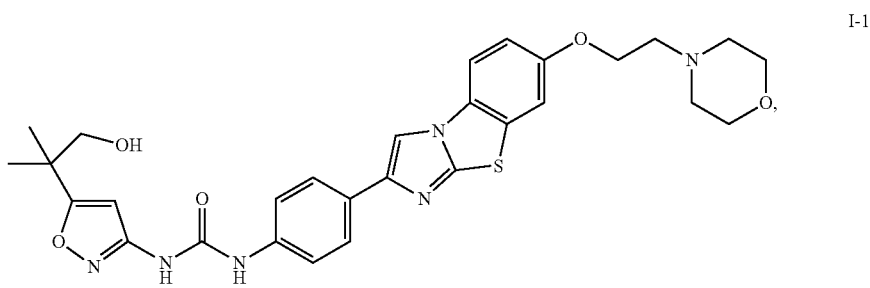

I-1

-continued
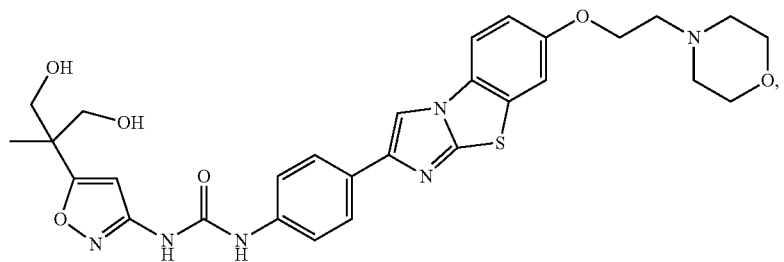
I-1a
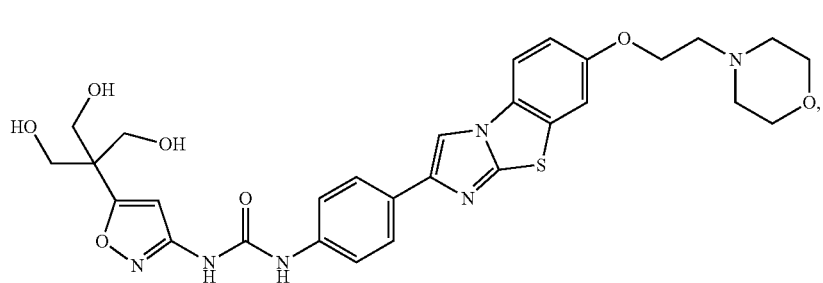
I-1b
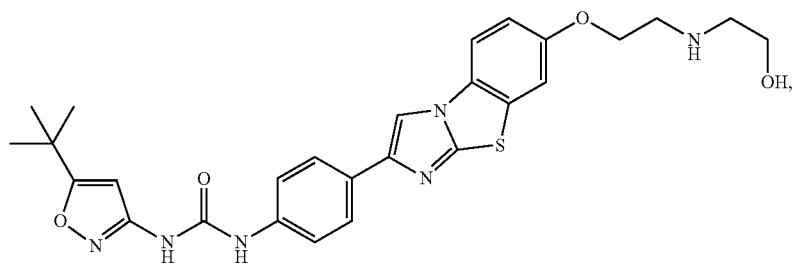
I-2
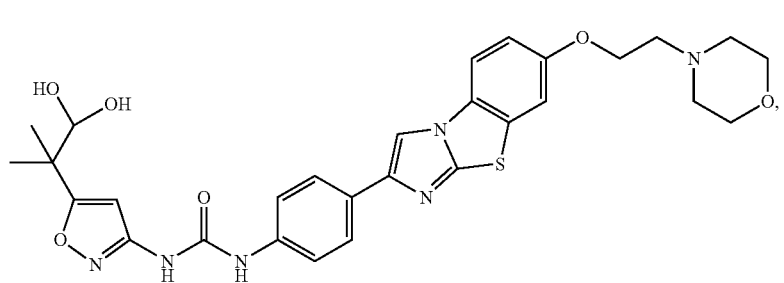
I-4
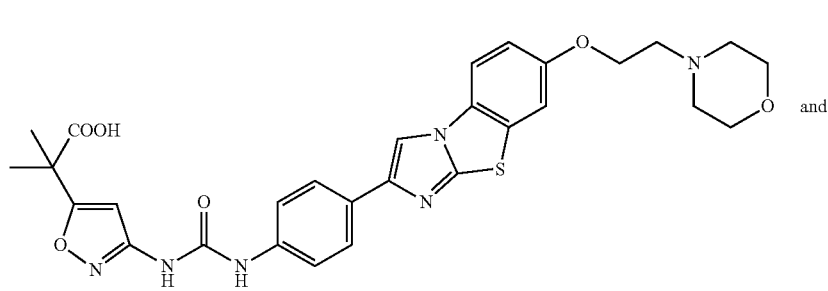
I-5 and
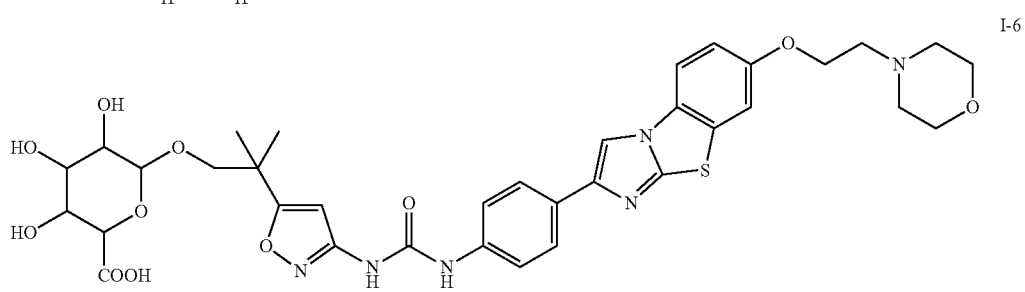
I-6 or a pharmaceutically acceptable salt, solvate, hydrate thereof.

In one embodiment, the compound provided herein is a glucuronidyloxy derivative of Compound IA.

In one embodiment, the compound provided herein is a glutathionyl derivative of Compound IA.

In one embodiment, the compound provided herein is a compound of formula I-1, I-1a, I-1b, I-2, I-3, I-4, I-5, I-6, I-7 or I-8.

In one embodiment, provided herein is a pure compound I-1. In another embodiment, provided herein is a pure compound I-2. In another embodiment, provided herein is a pure compound I-3. In another embodiment, provided herein is a pure compound I-1a. In another embodiment, provided herein is a pure compound I-1b. In one embodiment, provided herein is a pure compound I-4. In one embodiment, provided herein is a pure compound I-5. In one embodiment, provided herein is a pure compound I-6. In one embodiment, provided herein is a pure compound I-7. In one embodiment, the glucuronidyloxy derivative of Compound IA is pure. In one embodiment, the glutathionyl derivative of Compound IA is pure.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

In one embodiment, the compounds provided herein have activity as protein kinase modulators. Further provided are methods of treating, preventing or ameliorating diseases that are modulated by protein kinases and pharmaceutical compositions and dosage forms useful for such methods. The methods and compositions are described in detail in the sections below.

In one embodiment, compounds and compositions provided herein are effective in methods of modulating the activity of the platelet derived growth factor receptor (PDGFR) subfamily, which includes PDGFR α, PDGFR β, CSF-1R, c-kit and Flt3, including wild type and mutant ftl3.

In one embodiment, compounds and compositions provided herein are effective to modulate the activity the fetus liver kinase ("flk") receptor subfamily, which includes kinase insert domain-receptor fetal liver kinase-1 (KDR/FLK-1), flk-1R, flk-4 and fms-like tyrosine kinase 1 (flt-1).

In another aspect, compounds and compositions provided herein are effective to modulate the activity of the "HER" receptor tyrosine kinase subfamily, which includes EGFR (epithelial growth factor receptor), HER2, HER3 and HER4.

In one embodiment, compounds and compositions provided herein are effective to modulate the activity of the vascular endothelial growth factor ("VEGF") receptor subgroup.

In one embodiment, compounds and compositions provided herein are effective to modulate the activity of the fibroblast growth factor ("FGF") receptor subgroup, which includes the receptors FGFR1, FGFR 2, FGFR3, and FGFR4, and the ligands, FGF1, FGF2, FGF3, FGF4, FGF5, FGF6, and FGF7.

In another aspect, compounds and compositions provided herein are effective to modulate the activity of the c-Met receptor family.

In another aspect, compounds and compositions provided herein are effective to modulate the activity of the Abl protein tyrosine family.

In one embodiment, compounds and compositions provided herein are effective to modulate the activity of the fms-like tyrosine kinase 3 receptor kinase (FLT3 kinase).

In one embodiment, compounds and compositions provided herein are effective to modulate the activity of the Src subfamily, which includes Src, Yes, Fyn, Lyn, Lck, Blk, Hck, Fgr and Yrk.

In one embodiment, compounds and compositions provided herein are effective to modulate the activity of one or more kinases selected from the group consisting of sterile 20, sterile 11, sterile, the camk sub family (calmodulin regulated kinases and related kinases), the AGC sub family (protein kinase A, protein kinase G and protein kinase C), the CMGC sub family (cdk, map kinase, glycogen synthetase kinase and clk), the sterile 20 sub family, and Frk, Btk, Csk, Abl, Zap70, Fes, Fps, Fak, Jak and Ack, (and their respective subfamilies).

In another embodiment, provided herein are methods of using the disclosed compounds and compositions, or pharmaceutically acceptable salts, solvates, or hydrates thereof, for the local or systemic treatment or prophylaxis of human and veterinary diseases, disorders and conditions modulated or otherwise affected mediated via kinase activity.

C. Preparation of Compounds

The compounds provided herein can be prepared, isolated or obtained by any method apparent to those of skill in the art. Exemplary methods of preparation are described in detail in the examples below. Compound IA can be prepared by methods described in US Pub. No. 2007/0232604.

Starting materials in the synthesis examples provided herein are either available from commercial sources or via literature procedures either as cited or as found, for example in March *Advanced Organic Chemistry: Reactions, Mechanisms, and Structure*, (1992) 4th Ed.; Wiley Interscience, New York. All commercially available compounds were used without further purification unless otherwise indicated. Proton ($^1$H) nuclear magnetic resonance (NMR) spectra were recorded on a Bruker Avance 300 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) downfield relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Preparative HPLC was performed using Varian HPLC systems and Phenomenex columns.

It is understood that in the following description, combinations of substituents and/or variables of the depicted formulae are permissible only if such contributions result in stable compounds under standard conditions.

One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is, E/Z isomers, enantiomers and/or diastereomers.

Standard abbreviations and acronyms, for example, as defined in *J. Org. Chem.* 2007 72(1): 23A-24A are used herein. Certain abbreviations and acronyms used herein are as follows:

| ACN | Acetonitrile |
|---|---|
| DIEA | diisopropylethylamine |
| DCM | dichloromethane |
| EDCI | N-(3-Dimethylaminopropyl)-N'-ethylcarbodiimide hydrochloride |
| EtOAc | ethyl acetate |
| EtOH | ethanol |
| HOAc | acetic acid |
| MeOH | methanol |
| MRM | Multiple Reaction Monitoring |
| TEA | triethylamine |

In certain embodiments, compounds provided herein are synthesized according to the methods illustrated in Scheme 1. Compound 2, synthesized as described in Example 4 Procedure B, is treated with an appropriate 2-chloroethyl amine, in certain embodiments, in the presence of potassium iodide and normally in the presence of a base such as potassium carbonate or cesium carbonate in a solvent such as DMF or DMSO with moderate heating as necessary to afford aryloxy amine (A). The nitro group of (A) is reduced by, for example, catalytic hydrogenation using hydrogen gas or a hydrogen transfer reagent such as formic acid or ammonium formate in the presence of a noble metal catalyst such as Pd/C or Pd(OH)$_2$ or Raney nickel or PtO$_2$ in a solvent such as MeOH, EtOH, EtOAc, THF, or DMF, or mixtures thereof; or alternatively under dissolving metal conditions in the presence of acid, for example Sn or Fe or Zn in the presence of aqueous HCl or HOAc; or alternatively using a reagent such as SnCl$_2$ in a solvent such as EtOH or DMF, optionally in the presence of a tertiary amine base; or alternatively using a reagent such as sodium dithionite or titanium trichloride in a suitable solvent or solvent mixture. The resulting amino compound (B) may then be treated with a suitable isoxazolyl-carbamoylating agent, for example, an aryl isoxazol-3-ylcarbamate such as a phenyl isoxazol-3-ylcarbamate (C) prepared as described in Scheme 6, or, for example, a 3-isocyanato-isoxazole (D) prepared as described in Scheme 7, in a suitable dry solvent such as THF, dioxane, EtOAc, DMF, NMP, or DCM, optionally in the presence of a base such as DIEA, TEA, or an alkali metal carbonate, and optionally in the presence of DMAP, with moderate heating as necessary to complete the reaction to form compounds (Z).

Scheme 1

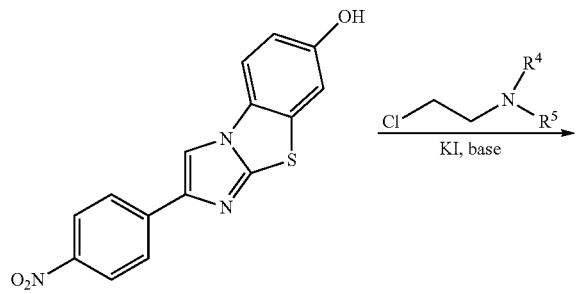

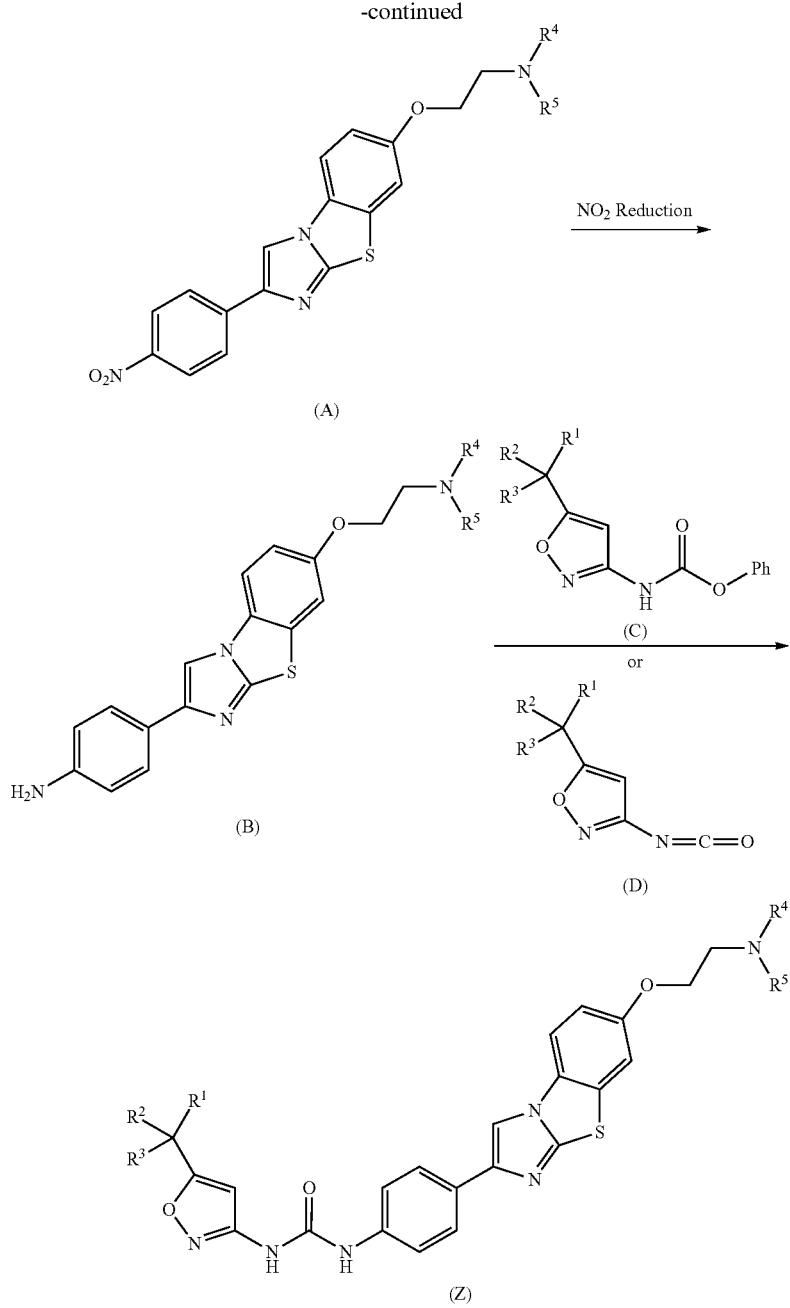

In certain embodiment, compounds provided herein are synthesized according to methods illustrated in Scheme 2. Compound 2, synthesized as described in Example 4, Procedure B, is treated with 1-bromo-2-chloroethane, in one embodiment, in the presence of potassium iodide and additionally in the presence of a base such as potassium carbonate or cesium carbonate in a solvent such as DMF or DMSO with moderate heating as necessary to afford chloride (E). The nitro group of (E) is reduced by one of the methods described in association with Scheme 1 for conversion of (A) to (B), and the resulting amino compound (F) is subsequently treated with a suitable isoxazolyl-carbamoylating agent to afford (G) in a procedure analogous to that described in association with Scheme 1 for conversion of (B) to (C).

The resulting chloride compound (G) is then treated with a secondary or primary amine, either in excess or alternatively in the presence of additional base such as DIEA, TEA or an alkali metal carbonate, in a suitable dry solvent such as THF, dioxane, DMF, NMP, or DCM, in one embodiment, in the presence of potassium iodide, and with moderate heating as necessary to complete the reaction to form compound (Z). As an alternative to use of a primary amine described above for the formation of (Z), a secondary amine in which one of the R groups, for example the $R^5$ group, is cleavable in a subsequent step may be used. For example, if $R^5$=benzyl or substituted benzyl, then $R^5$ may be subsequently removed by catalytic hydrogenation or other suitable means well known in the art to give the final product (Z) with $R^5$=H.

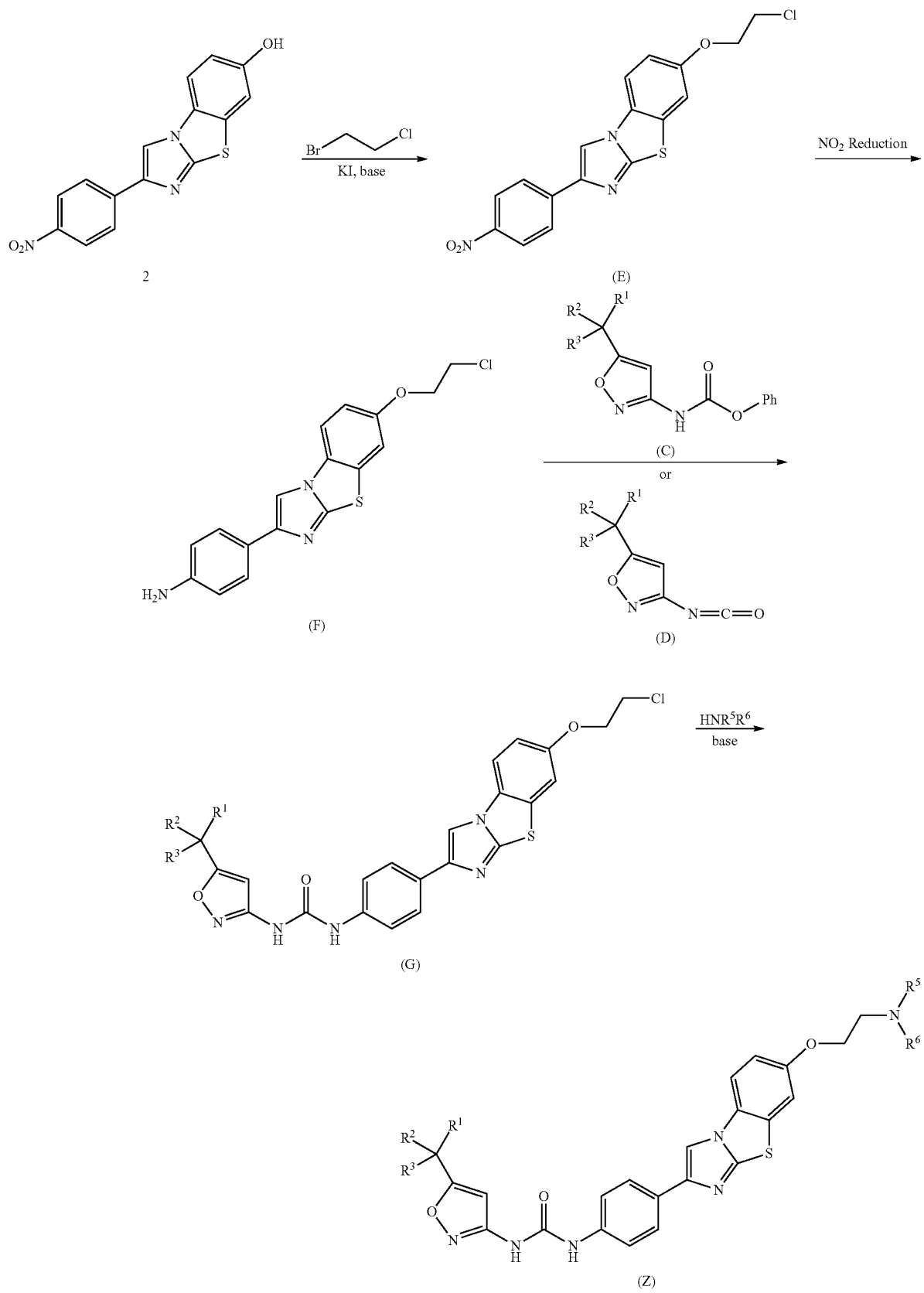

As illustrated in Scheme 3, in the case where one of the substituents $R^4$ or $R^5$, for example $R^4$, on the amino group of compounds (Z) consists of a —$CH_2CH_2OH$ group, prepared, for example as shown in Scheme 3, then this primary alcohol moiety may be oxidized to obtain further compounds provided herein, wherein the —$CH_2OH$ group has been transformed to a —COOH group, to give compounds (Z) wherein $R^4$=—$CH_2COOH$. Suitable conditions for oxidizing a —$CH_2OH$ group to —COOH include, for example, treatment with pyridinium dichromate in DMF. Alternatively, treatment of the primary alcohol with Dess-Martin periodinane in a solvent such as dichloromethane or alternatively treatment of the primary alcohol in a solvent, such as dichloromethane or DMSO, with a reagent formed by pretreating DMSO with oxalyl chloride (Swern conditions), acetic anhydride, or pyridine-sulfur trioxide, followed by treatment with a tertiary amine base such as triethylamine affords an intermediate aldehyde. The intermediate aldehyde may then be further oxidized to the carboxylic acid with a mild oxidizing agent such as silver oxide or sodium chlorite in a suitable solvent.

The immediately preceding transformations will be most effective when the isoxazole substituents $R^1$, $R^2$, $R^3$ do not contain oxidizable groups such as $CH_2OH$, or alternatively, when such groups are present in protected form, for example, in the case of exposed hydroxyl groups as silyl or benzyl ethers. In the latter case, such protecting groups may be removed at a suitable step in the sequence, for example by treatment with fluoride or acid in the case of a silyl ether, or by noble metal-catalyzed hydrogenolysis in the case of a benzyl ether. Accordingly, in Scheme 3, the isoxazole 5-substituent is represented as R(P), which shall be understood to mean a substituent where any of the associated R groups ($R^1$, $R^2$, $R^3$) that bear a hydroxyl or carboxyl group are in optionally in protected form, and such protection is removed at a suitable stage of the synthesis as dictated by specific circumstances, but in any case, is removed in the final step of the sequence if not sooner. This context-dependent deprotection step is expressed explicitly in Scheme 3 and is implicit in subsequent schemes where R(P) is used to represent the 5-substituent of the isoxazole ring. Strategies for protection and deprotection of common moieties such as hydroxyl, carboxyl, and amino groups are very well known in the art; for example see P. G. Wuts, T. W. Greene, "Greene's Protective Groups in Organic Synthesis", 4th edition, Wiley 2007.

Scheme 3

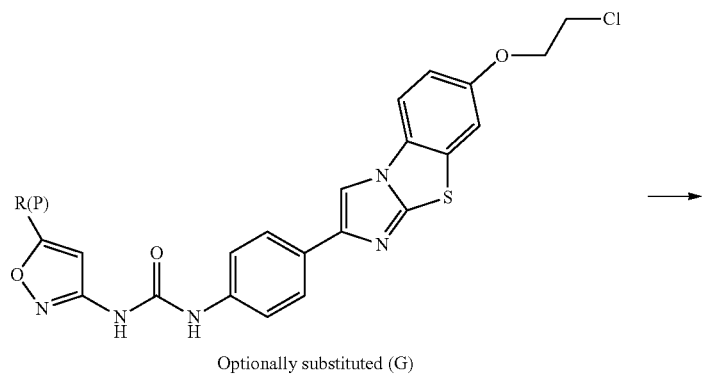

Optionally substituted (G)

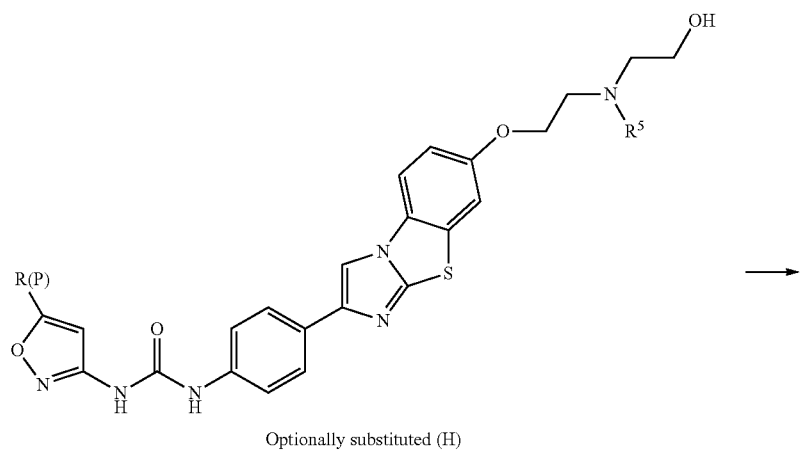

Optionally substituted (H)

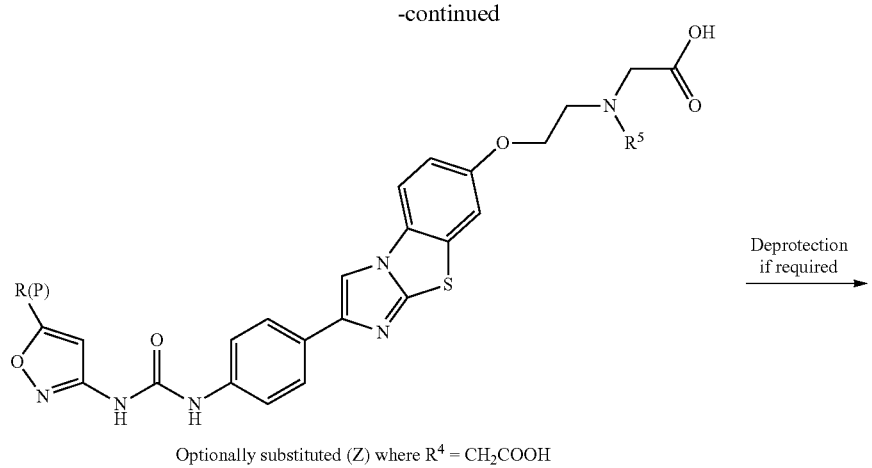

Optionally substituted (Z) where $R^4 = CH_2COOH$

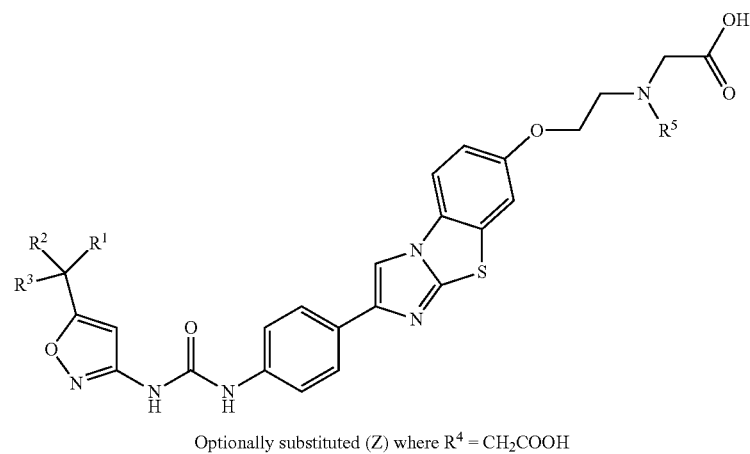

Optionally substituted (Z) where $R^4 = CH_2COOH$

An alternative approach to preparing compounds (Z) with $R^4=CH_2CH_2OH$ or $R^4=CH_2COOH$ is illustrated in Scheme 4. In Scheme 4, chloride compound (G), prepared as described in Scheme 2, is treated with a glycine ester derivative for example, glycine methyl ester, in the presence of base and heating as necessary to form the alkylated glycine ester derivative (H). Following isolation, ester (H) may be saponified to give (Z) ($R^4=CH_2COOH$) or ester (H) may be reduced, for example, with lithium borohydride in THF or calcium borohydride in ethanol/THF to form (Z) ($R^4=CH_2CH_2OH$).

Scheme 4

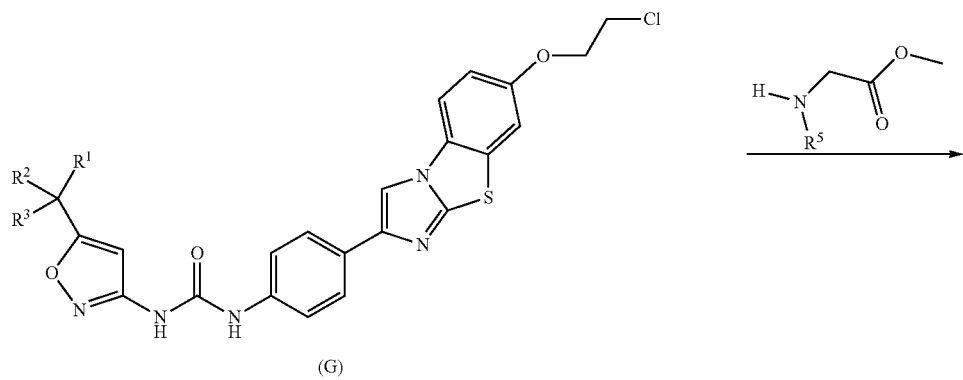

(G)

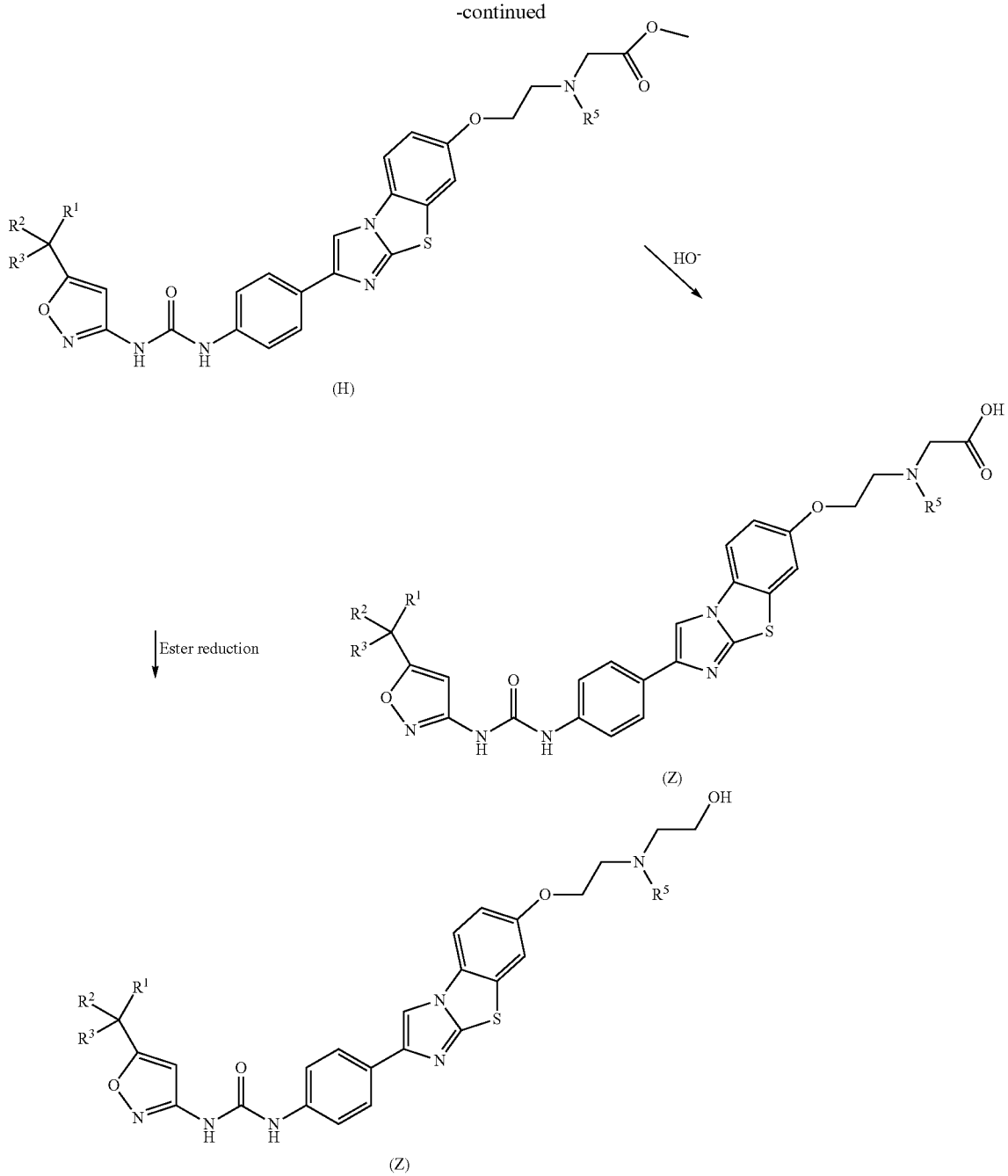

An alternative method for preparing compounds (Z) with R⁴=CH₂CH₂OH or R⁴—CH₂COOH is illustrated in Scheme 5. The hydroxyl group of compound 2 is alkylated with an ester of bromoacetic acid, for example, with methyl bromoacetate, in one embodiment, in the presence of potassium iodide, and normally in the presence of a base such as potassium carbonate or cesium carbonate, in a solvent such as DMF or DMSO, with moderate heating as necessary to afford an aryloxyacetic ester (I). As described in association with Scheme 1, the nitro group of (I) is then reduced to an amino group to provide compound (J), which may be converted to ureas (K) as described for Scheme 1. The ester group of a compound (K) is then transformed to an aldehyde (L) by methods well known in the art. For example, direct conversion of the ester to the aldehyde may be effected by treatment with diisobutylaluminum hydride in toluene. Alternatively, the ester may first be reduced to the primary alcohol by treatment with a reagent such as LiBH₄ in THF or CaBH₄ in alcohol/THF, or by saponification to the acid followed by treatment with BH₃ in THF. The intermediate primary alcohol is then oxidized to the aldehyde by treatment with Dess-Martin periodinane in a solvent such as dichloromethane, or alternatively by treatment of the primary alcohol in a solvent such as dichloromethane or DMSO with a reagent formed by pretreating DMSO with oxalyl chloride (Swern conditions), acetic anhydride, or pyridine-sulfur trioxide, followed by treatment with a tertiary amine base such as triethylamine. Aldehydes (L) thus formed are treated with a suitable ethanolamine derivative under reductive amination conditions, for example, in the presence of sodium cyanoborohydride or sodium triacetoxyborohydride in a solvent such as MeOH or MeOH/HOAc, to afford desired product (Z) (R$^4$=CH$_2$CH$_2$OH). Treatment of aldehydes (L) with a glycine ester derivative under the above reductive amination conditions followed by saponification of the ester provides compounds (Z) with R$^4$=CH$_2$COOH. As discussed in the context of Scheme 3, in cases where the R group of the isoxazole moiety contains groups, such as hydroxyl, which may be reactive under some of the above reaction conditions, such reactive groups may be carried through these steps in protected form with removal of protecting group(s) at a suitable stage of the synthesis.

Scheme 5

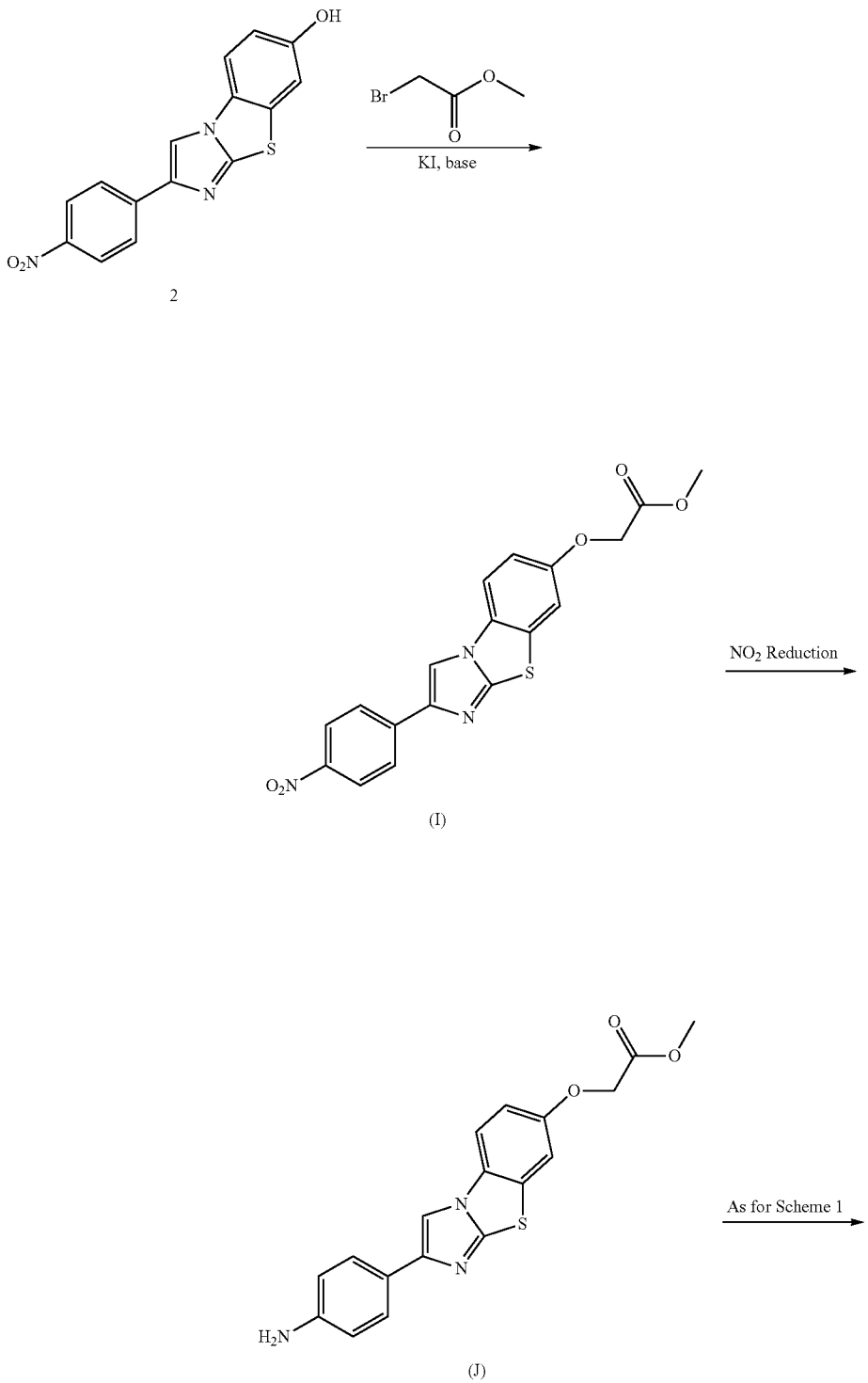

-continued
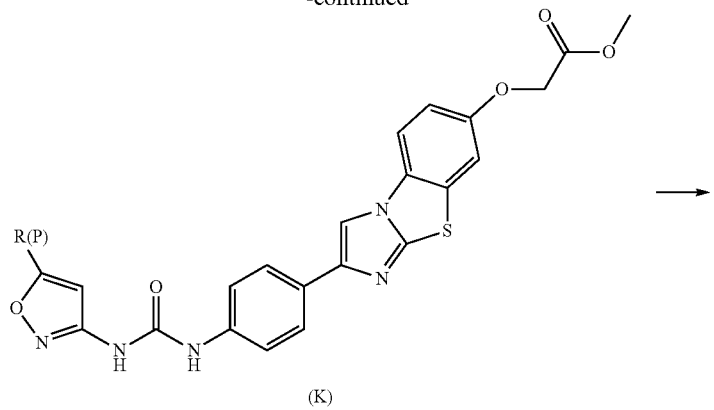
(K)
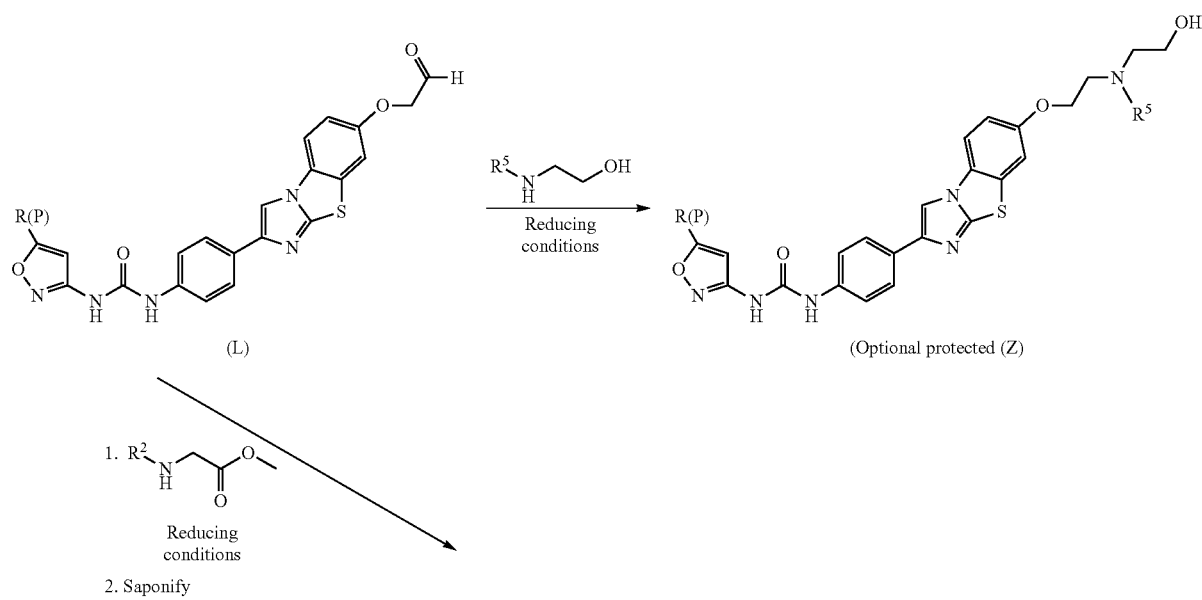
(L) → (Optional protected (Z))
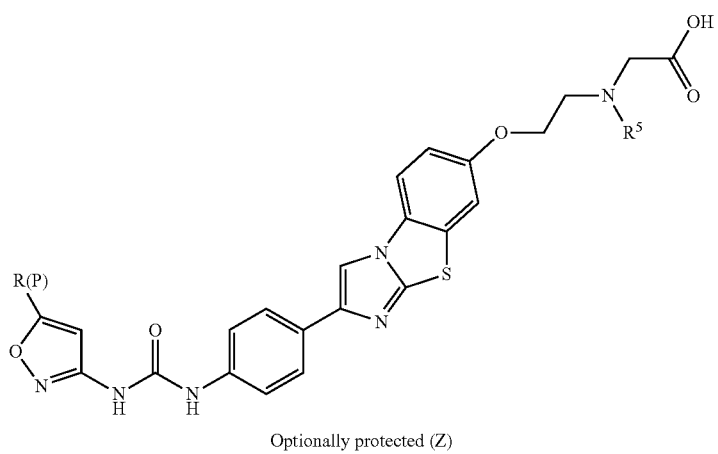
Optionally protected (Z)

The preparation of the isoxazolyl-carbamoylating agents required to form the urea moieties in Schemes 1, 2, and 5 are prepared as illustrated in Schemes 6 and 7. In Scheme 6, a precursor isoxazole-3-amine MMM, prepared as described in Scheme 8, is treated with an aryl chloroformate, for example with phenyl chloroformate, in the presence of a base such as alkali metal carbonate such as potassium carbonate or a tertiary amine such as diisopropylethylamine or triethylamine in a dry solvent such as THF, dichloromethane, ethyl acetate, or DMF to afford the required 3-(aryloxycarbonylamino)isoxazole.

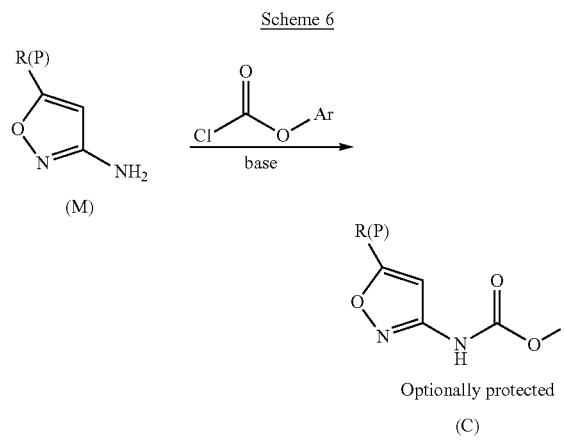

In Scheme 7, a precursor isoxazole-3-amine (M) prepared as described in Scheme 8 is treated with phosgene, diphosgene (trichloromethyl chloroformate) or triphosgene (bistrichloromethyl carbonate) in the presence of a base such as alkali metal carbonate, for example potassium carbonate, or a tertiary amine, for example, diisopropylethylamine or triethylamine, in a dry solvent such as THF, dichloromethane, ethyl acetate, or DMF with mild heating as necessary to afford the required 3-isocyanatoisoxazole.

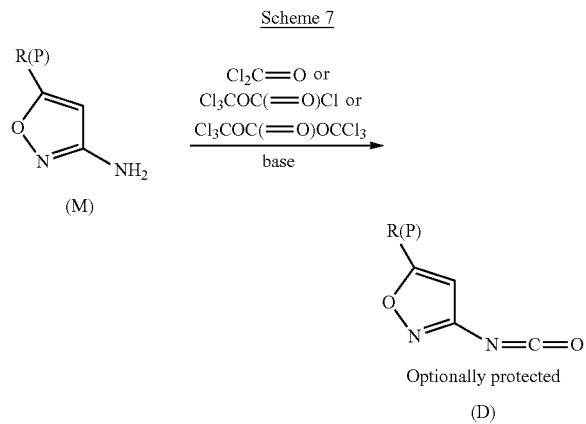

Preparation of the isoxazole-3-amines required as starting materials in Schemes 6 and 7 is illustrated in Scheme 8. The ester starting material, containing an R group (in protected form if the R group contains reactive moieties, for example hydroxyl groups; see discussion of Scheme 3) is treated with an alkali metal salt of acetonitrile, for example, the sodium salt, normally formed by treatment of acetonitrile with an alkali metal hydride, for example sodium hydride, in a dry solvent such as THF, dioxane, or DMF, with heating as necessary. The resulting β-oxonitrile (N) is then treated with hydroxylamine at an appropriate pH followed by heating with acid to form the required 3-aminoisoxazole. Some protecting groups, for example silyl groups, used to protect free hydroxyl moieties, are sensitive to the above acidic conditions. In such cases, the synthesis may proceed from β-oxonitrile (N) with the R group in unprotected form. Alternatively, if the synthesis requires R to be in protected form in order to most effectively execute one or more subsequent synthetic steps, then a protecting group may be chosen in the starting ester, for example, benzyl, that is less sensitive to acid conditions. Alternatively, if the synthesis requires R to be in protected form, then a reprotection step may be carried out at a suitable stage of the synthesis followed by deprotection at a suitable stage of the synthesis.

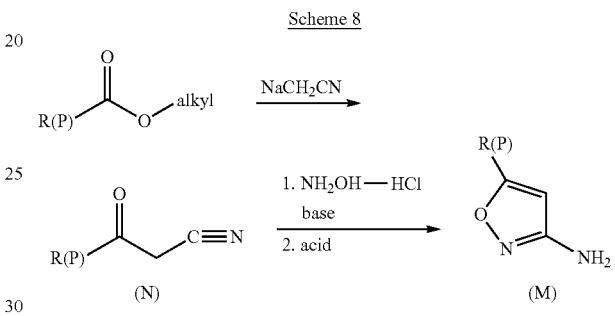

In certain embodiment, in the compounds provided herein, one or more of the R groups $R^1$, $R^2$, $R^3$ on the 5-position substituent of the isoxazole ring contains one or more carboxyl groups. In such cases, the sequence in Scheme 8 may be feasible with such carboxyl group(s) unprotected, followed by protection, for example, as an ester prior to conducting the remainder of the synthetic sequence, followed by deprotection of the carboxyl group (ester cleavage) at a suitable stage of the synthesis. Alternatively, the synthesis may be conducted with the R(P) group having the required number of protected or unprotected primary alcohol group(s), whereby oxidation of the alcohol group(s) to the carboxyl group(s) is effected at a suitable stage of the synthesis. Suitable methods for oxidizing a primary alcohol to a carboxylic acid are discussed above in association with Scheme 3. In cases where such oxidations are carried out when another R group in the molecule, for example, $R^4$, contains an oxidizable group, for example, a primary or secondary alcohol, then it is advisable that such group be in protected form during the oxidation step, and then subsequently deprotected at a suitable stage of the synthesis. As already described and referenced, required selective or orthogonal protection and deprotection strategies are well known in the art.

Compounds provided herein may consist of a glucuronic acid conjugate (glucuronide), produced when a hydroxyl group of a precursor such as (O) (Scheme 9) forms a bond with the glycosidic carbon atom of glucuronic acid. Synthetic preparation of glucuronides can be effected in vitro in the presence of UDP-glucuronysyltransferases, for example as described in Wilkinson, et al., *Org. Lett.* 2008, 10, 1585-1588. If the parent molecule (O) contains more than one free hydroxyl group prior to glucuronidation, it may be advisable that any hydroxyl group that should remain in free form following glucuronidation should be suitably protected during the glucuronidation step, either by a separate protection step or by incorporation in protected form, followed by deprotection at a suitable stage of the synthesis. Non-enzymatic methods for introduction of the glucuronyl moiety are also available (see, for example, Ramu and Backer, *J. Med. Chem.* 1995, 38, 1911-1921, references therein; Rousch, et al, *J. Am. Chem. Soc.* 1985, 107, 3354-3355; WO2007/35717).

fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such Scheme 9

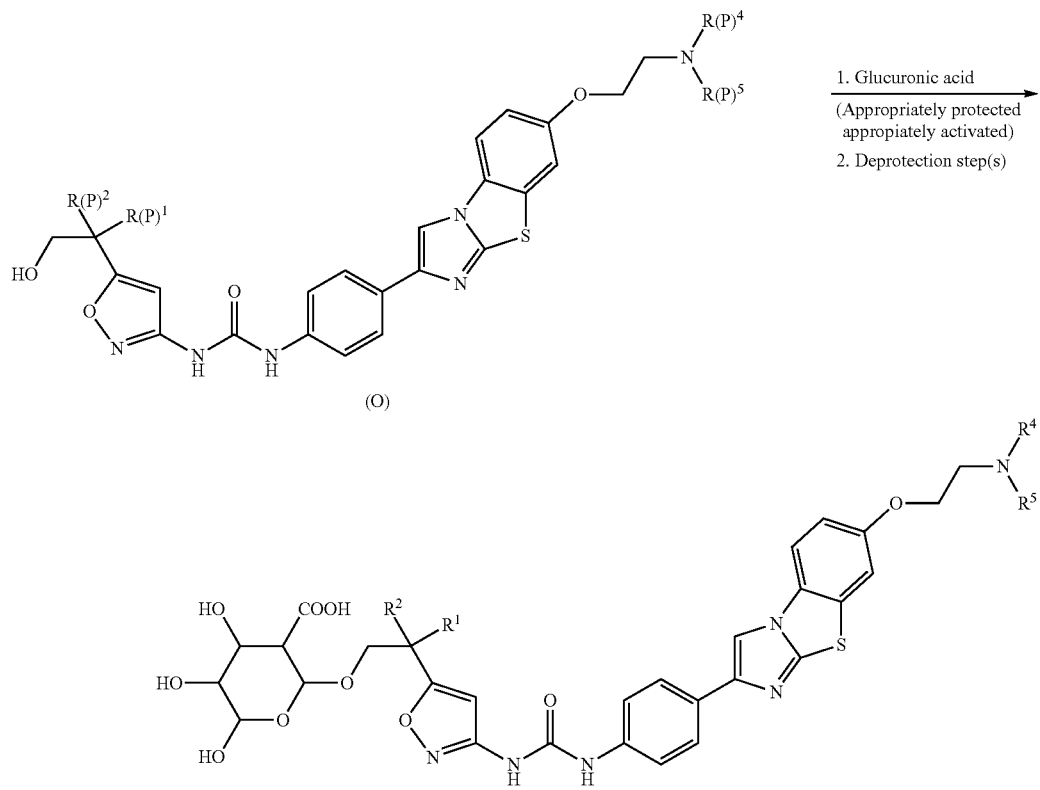

(O)

In one embodiment, Compound I-1, I-1a, I-1b, I-2, I-3, I-4, I-5, I-6 or I-7 is isolated in purified form.

D. Formulation of Pharmaceutical Compositions

In certain embodiments, provided herein are pharmaceutical compositions comprising a compound provided herein as an active ingredient. In one embodiment, pharmaceutical compositions comprise Compound I-1, I-1a, I-1b, I-2, I-3, I-4, I-5, I-6, I-7 or I-8 in a purified form.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salt, solvate, hydrate or prodrug is (are) mixed with a suitable pharmaceutical carrier or vehicle. The concentrations of the compounds in the compositions are effective for delivery of an amount, upon administration, that treats, prevents, or ameliorates one or more of the symptoms of kinase mediated diseases described herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

In certain embodiments, a composition is provided comprising the active compound in combination with a polyglycolyzed glyceride known to those of skill in the art. The compound may be incorporated into a semi-solid matrix comprising polyglycolized glycerides, such as GELUCIRE. The polyglycolized glyceride is e.g., a semi-solid excipient composed of fatty acid (C8-C18) esters of glycerol and polyethylene glycol (PEG) esters. In another embodiment, the polyglycolized glyceride GELUCIRE is e.g., a semi-solid excipient composed of fatty acid (C12-C18) esters of glycerol and polyethylene glycol (PEG) esters. The polyglycolized glyceride is optionally a semisolid surfactant.

The polyglycolyzed glyceride includes, e.g., a mixture of mono-, di- and triglycerides and polyethylene glycol (PEG) mono- and diesters, which may be of molecular weight between 200 and 600, where appropriate of free glycerol and free PEG, whose hydrophile-lipophile balance (HLB) value can be adjusted by the length of the PEG chain, and whose melting point can be adjusted by the length of the chains of the fatty acids, of the PEG and by the degree of saturation of the fatty chains, and hence of the starting oil. Examples of such mixtures include GELUCIRE. See, e.g., PCT publication no. WO 2007/038796 and U.S. Pat. Nos. 4,797,286, 5,433,951 and 6,171,615, the contents of which are hereby incorporated by reference in their entireties.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases described herein.

Typically a therapeutically effective dosage should produce a serum concentration of active ingredient of from about 1 ng/ml to about 50-100 μg/ml. The pharmaceutical compositions typically should provide a dosage of from about 10 mg to about 4000 mg of compound per kilogram of body weight per day. Pharmaceutical dosage unit forms are prepared to provide from about 10 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylenevinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-betacyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 50-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microtine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

E. Evaluation of The Activity of the Compounds

Standard physiological, pharmacological and biochemical procedures are available for testing the compounds to identify those that possess biological activities that selectively modulate the activity of kinases.

Such assays include, for example, biochemical assays such as binding assays, radioactivity incorporation assays, fluorescence polarization assays, fluorescence resonance energy transfer (FRET) based assays (see generally Glickman et al., *J. Biomolecular Screening,* 7 No. 1 3-10 (2002)), as well as a variety of cell based assays.

In one embodiment, inhibition is determined in vitro. In a specific embodiment, inhibition is assessed by phosphorylation assays. Any suitable phosphorylation assay can be employed. For example, membrane autophosphorylation assays, receptor autophosphorylation assays in intact cells, and ELISA's can be employed. See, e.g., Gazit, et al., *J. Med. Chem.* (1996) 39:2170-2177, Chapter 18 in CURRENT PROTOCOLS IN MOLECULAR BIOLOGY (Ausubel, et al., eds. 2001).

In addition a variety of cell based assay methodologies can be successfully used in screening assays to identify and profile the specificity of compounds provided herein. Cells useful in such assays include cells with wildtype or mutated forms. In one embodiment, the wildtype is a kinase that is not constitutively active, but is activated with upon dimerization. For example, the mutant FLT3 kinase is constitutively active via internal tandem duplication mutations or point mutations in the activation domain. Suitable cells include those derived through cell culture from patient samples as well as cells derived using routine molecular biology techniques, e.g., retroviral transduction, transfection, mutagenesis, etc. Exemplary cells include Ba/F3 or 32Dc13 cells transduced with, e.g., MSCV retroviral constructs FLT3-ITD (Kelly et al., 2002); Molm-13 and MolI-14 cell line (Fujisaki Cell Center, Okayama, Japan); HL60 (AML-M3), AML193 (AML-M5), KG-1, KG-1a, CRL-1873, CRL-9591, and THP-1 (American Tissue Culture Collection, Bethesda, Md.); or any suitable cell line derived from a patient with a hematopoietic malignancy.

In some embodiments, the compounds described herein significantly inhibit receptor tyrosine kinases. A significant inhibition of a receptor tyrosine kinase activity refers to an $IC_{50}$ of less than or equal to 100 μM. In one embodiment, the compound can inhibit activity with an $IC_{50}$ of less than or equal to 50 μM, in other embodiment, less than or equal to 10 in other embodiment, less than 1 μM, less than 100 nM, less than 50 nM, less than 10 nM, less than 5 nM or less than 1 nM. Lower $IC_{50}$'s are preferred because the $IC_{50}$ provides an indication as to the in vivo effectiveness of the compound. Other factors known in the art, such as compound half-life, biodistribution, and toxicity should also be considered for therapeutic uses. Such factors may enable a compound with a lower $IC_{50}$ to have greater in vivo efficacy than a compound having a higher $IC_{50}$. In one embodiment, a compound that inhibits activity is administered at a dose where the effective tyrosine phosphorylation, i.e., $IC_{50}$, is less than its cytotoxic effects, $LD_{50}$.

Compound binding may also be determined using phage display of fusion proteins exposed on the outer surface of the phage head, for example using an affinity based phage display screening system as described in Fabian et al., (*Nat Biotechnol.* 2005 23(3):329-36). This approach employs a competition binding assay to determine the relative affinity of a compound of interest to a protein expressed as a fusion protein on the surface of the T7 bacteriophage. The assay uses phage tagged with a kinase of interest and an immobilized bait which are combined with the compound to be tested. A test compound which binds to the kinase directly or indirectly competes with the immobilized bait and prevents the binding of the phage-tagged kinase to the solid support. If the compound does not bind to the kinase, the tagged phage can bind to the solid support through the interaction between the kinase and the immobilized bait. The results can be read out by quantifying the amount of fusion protein bound to the solid support, which can be accomplished by either traditional plaque assays or by quantitative PCR (QPCR) using the phage genome as a template.

F. Methods of Use of the Compounds and Compositions

Also provided herein are methods of using the disclosed compounds and compositions, or pharmaceutically acceptable salts, solvates or hydrates thereof, for the treatment, prevention, or amelioration of a disease or disorder that is mediated or otherwise affected via protein kinase activity or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7:334-339 (1994)). Consistent with the description above, such diseases or disorders include without limitation:

1). a) carcinomas, including Kit-mediated carcinomas, adenocarcinoma, squamous cell carcinoma, adenosquamous carcinoma, teratocarcinoma, head and neck cancer, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including flt3 and/or Kit-mediated small cell lung cancer, stomach/gastric cancer, gastrointestinal cancer, gastrointestinal stromal tumors (GIST) including Kit-mediated GIST and PDGFRα-mediated GIST, colon cancer, colorectal cancer, pancreatic cancer, islet cell carcinoma, hepatic/liver cancer, metastases to the liver, bladder cancer, renal cell cancer including PDGFR-mediated renal cell cancer, cancers of the genitourinary tract, ovarian cancer including Kit-mediated and/or PDGFR-mediated ovarian cancer, endometrial cancer including CSF-1R-mediated endometrial cancer, cervical cancer, breast cancer including Flt3-mediated and/or PDGFR-mediated breast cancer, prostate cancer including Kit-mediated prostate cancer, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF-1R-mediated bone metastases, metastatic tumors including VEGFR-mediated tumors, stromal tumors, neuroendocrine tumors, tumor angiogenesis including VEGFR-mediated tumor angiogenesis, mixed mesodermal tumors;

b) sarcomas including PDGFR-mediated sarcomas, osteosarcoma, osteogenic sarcoma, bone cancer, glioma including PDGFR-mediated and/or CSF-1R-mediated glioma, astrocytoma, vascular tumors including VEGFR-mediated vascular tumors, Kaposi's sarcoma, carcinosarcoma, hemangiosarcomas including VEGFR3-mediated hemangiosarcomas, lymphangiosarcoma including VEGFR3-mediated lymphangiosarcoma;

c) myeloma, leukemia, myeloproliferative diseases, acute myeloid leukemia (AML) including flt3 mediated and/or KIT-mediated and/or CSF1R-mediated acute myeloid leukemia, chronic myeloid leukemias (CML) including Flt3-mediated and/or PDGFR-mediated chronic myeloid leukemia, myelodysplastic leukemias including Flt3-mediated myelodysplastic leukemia, myelodysplastic syndrome, including Flt3 mediated and/or Kit-mediated myelodysplastic syndrome, idiopathic hypereosinophilic syndrome (HES) including PDGFR-mediated HES, chronic eosinophilic leukemia (CEL) including PDGFR-mediated CEL, chronic myelomonocytic leukemia (CMML), mast cell leukemia including Kit-mediated mast cell leukemia, or systemic mastocytosis including Kit-mediated systemic mastocytosis; and d) lymphoma, lymphoproliferative diseases, acute lymphoblastic leukemia (ALL), B-cell acute lymphoblastic leukemias, T-cell acute lymphoblastic leukemias, natural killer (NK) cell leukemia, B-cell lymphoma, T-cell lymphoma, and natural killer (NK) cell lymphoma, any of which may be Flt3 mediated and/or PDGFR-mediated, Langerhans cell histiocytosis including CSF-1R-mediated and flt3-mediated Langerhans cell histiocytosis, mast cell tumors and mastocytosis;

2) Nonmalignant proliferative diseases; atherosclerosis including PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated;

3) Inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), including any of the aforementioned diseases which are flt3-mediated and/or CSF-1R-mediated; and 4) Infectious diseases mediated either via viral or bacterial pathogens and sepsis, including KIT-mediated sepsis.

Also provided are methods of modulating the activity, or subcellular distribution, of kinases in a cell, tissue or whole organism, using the compounds and compositions provided herein, or a pharmaceutically acceptable salt, solvate or hydrate thereof.

Kinases of high interest, i.e. those that mediate one or more of the aforementioned diseases or disorders, include without limitation the following enzymes:

1) The platelet derived growth factor receptor (PDGFR) subfamily, which includes PDGFR α, PDGFR β, CSF-1R, Kit and Flt3;
2) The vascular endothelial growth factor (VEGF) receptor subfamily, which includes VEGFR1 (Flt1), VEGFR2 (KDR or Flk1) and VEGFR3 (Flt4);
3) Ret;
4) The HER (EGFR) subfamily;
5) The FGFR subfamily;
6) The HGFR (Met) subfamily;
7) The Abl protein tyrosine subfamily;
8) The Src subfamily, which includes Src, Yes1, Fyn, Lyn, Lck, Blk, Hck, Fgr and Yrk;
9) Frk, Btk, Csk, Abl, Syk, Fes, Fps, Fak, Jak and Ack, (and their respective subfamilies);
10) A kinase selected form the group consisting of prostate-derived sterile 20, sterile 11 and sterile 7;
11) the cam kinase subfamily (calmodulin regulated kinases and related kinases);
12) the AGC subfamily; and
13) the CMGC sub family (cdk, map kinase, glycogen synthetase kinase and clk).

In one embodiment, the methods provided herein are for treating cancers, including, but not limited to head and neck cancer, (originating lip, oral cavity, oropharynx, hypopharynx, larynx, nasopharynx, nasal cavity and paranasal sinuses, salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of vater; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, prostate cancer, penile cancer, urethral cancer; neurologic tumors; endocrine neoplasms, including carcinoid and islet cell tumors, pheochromocytoma, adrenal cortical carcinoma, parathyroid carcinoma and metastases to endocrine glands.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer.

In one embodiment, the cancer is a leukemia. In one embodiment, the leukemia is chronic lymphocytic leukemia, chronic myelocytic leukemia, acute lymphoblastic leukemia, acute myeloid leukemia, and acute myeloblastic leukemia.

In another embodiment, the leukemia is acute leukemia. In one embodiment, the acute leukemia is acute myeloid leukemia (AML). In one embodiment, acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myeloid leukemia is undifferentiated AML (M0). In yet another embodiment, the acute myeloid leukemia is myeloblastic leukemia (M1). In yet another embodiment, the acute myeloid leukemia is myeloblastic leukemia (M2). In yet another embodiment, the acute myeloid leukemia is promyelocytic leukemia (M3 or M3 variant [M3V]). In yet another embodiment, the acute myeloid leukemia is myelomonocytic leukemia (M4 or M4 variant with eosinophilia [M4E]). In yet another embodiment, the acute myeloid leukemia is monocytic leukemia (M5). In yet another embodiment, the acute myeloid leukemia is erythroleukemia (M6). In yet another embodiment, the acute myeloid leukemia is megakaryoblastic leukemia (M7). In yet another embodiment, the acute myeloid leukemia is promyelocytic leukemia. In yet another embodiment, the leukemia is attributable to a FLT3 internal tandem duplication (ITD) mutation. In yet another embodiment, the leukemia is attributable to a FLT3 point mutation. In still another embodiment, the FLT3 point mutation is a point mutation at amino acid D835.

In another embodiment, the acute leukemia is acute lymphocytic leukemia (ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In still another embodiment, the leukemia is drug resistant. In one embodiment, the subject has developed drug resistance to the anticancer therapy. In yet another embodiment, the subject has developed drug resistance to imatinib, sunitinib, gefitinib, erlotinib, nilotinib, dasatinib, lapatinib or sorafenib. In another embodiment, the subject has developed drug resistance to a FLT3 kinase inhibitor. In yet another embodiment, the subject has been treated with PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, or CHIR-258. In still another embodiment, the subject has a constitutively activating FLT3 mutation.

The cancers to be treated herein may be primary or metastatic. In one embodiment, the cancer is a solid or blood born metastatic tumor. In another embodiment, the cancer is metastatic cancer of bone.

The active ingredient(s) in one embodiment are administered in an amount sufficient to deliver to a patient a therapeutically effective amount of the active compound in order to e.g., treat the diseases described herein, without causing serious toxic effects in a treated subject.

A typical dose of the compound may be in the range of from about 1 to about 50 mg/kg, from about 1 to about 20 mg/kg, from about 0.1 to about 10 mg/kg, from about 0.5 mg/kg to about 10 mg/kg, of body weight per day, more generally from about 0.1 to about 100 mg/kg body weight of the recipient per day. Lower dosages may be used, for example, doses of about 0.5-100 mg, 0.5-10 mg, or 0.5-5 mg per kilogram body weight per day. Even lower doses may be useful, and thus ranges can include from about 0.1-0.5 mg/kg body weight of the recipient per day. The effective dosage range of the pharmaceutically acceptable derivatives is calculated based on the weight of the parent indole derivative compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 1 to 2000 mg, from about 10 to 1000 mg, or from about 25 to 700 mg of active ingredient per unit dosage form. In one embodiment, the unit dose is selected from 12, 18, 25, 27, 40, 50, 60, 90, 100, 135, 200, 250, 300, 400, 450, 500, 600, 675, 700, 800, 900 and 1000 mgs. For example, an oral dosage of from about 25 to 1000 mg is usually convenient, including in one or multiple dosage forms of 10, 12, 18, 25, 27, 40, 50, 60, 90, 100, 135, 200, 250, 300, 400, 450, 500, 600, 675, 700, 800, 900 or 1000 mgs. In certain embodiments, lower dosages may be used, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose or preferably as divided doses throughout a day. In particular embodiments, the compound or composition is administered four times per day. In particular embodiments, the compound or composition is administered three times per day. In particular embodiments, the compound or composition is administered two times per day. In particular embodiments, the compound or composition is administered once per day.

In one embodiment, the active ingredient is administered to achieve peak plasma concentrations of the active compound of from about 0.02 to 20 µM, from about 0.2 to about 5 µM or from about 0.5 to 10 µM. For example, this can be achieved by intravenous injection of a 0.1 to 5% solution of active ingredient, optionally in saline, or administered as a bolus of active ingredient. It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

G. Combination Therapy

Furthermore, it will be understood by those skilled in the art that the compounds provided herein, including pharmaceutical compositions and formulations containing these compounds, can be used in a wide variety of combination therapies to treat the conditions and diseases described above. Thus, also contemplated herein is the use of compounds, pharmaceutically acceptable salts, solvates or hydrates thereof provided herein in combination with other active pharmaceutical agents for the treatment of the disease/conditions described herein.

In one embodiment, such additional pharmaceutical agents include without limitation anti-cancer agents, anti-inflammatory agents and anti-emetics.

In certain embodiments, the anti-cancer agents include anti-metabolites (e.g., 5-fluoro uracil, methotrexate, 5-azacytidine, decitabine, gemcitabine, cytarabine (also known as cytosine arabinoside or Ara-C), HDAC (high dose cytarabine), fludarabine or clofarabine), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment. In another embodiment, the antimetabolite is administered in combination with gemtuzumab ozogamicin, daunorubicin, idarubicin or mitoxantrone.

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, glucocorticoid receptor agonists (e.g., corticosteroids, methylprednisone, prednisone, and cortisone) or antifolates such as methotrexate.

The compound or composition provided herein, or pharmaceutically acceptable salt of the compound, may be administered simultaneously with, prior to, or after administration of one or more of the above agents.

Pharmaceutical compositions containing a compound provided herein or pharmaceutically acceptable salt thereof, and one or more of the above agents are also provided.

Also provided is a combination therapy that treats or prevents the onset of the symptoms, or associated complications of cancer and related diseases and disorders comprising the administration to a subject in need thereof, of one of the compounds or compositions disclosed herein, or a pharmaceutically acceptable salt, solvate or hydrate thereof, with one or more anti-cancer agents.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the examples may be substituted with other suitable reagents. See, e.g., Smith & March, *Advanced Organic Chemistry*, 5$^{th}$ ed. (2001).

EXAMPLES

Example 1

In Vitro Metabolic Disposition of Compound IA in Rat, Monkey and Human Liver Microsomal Fractions Metabolic stability of Compound IA was measured in mouse, rat, dog, Cynomolgus monkey, and human microsomes.

Study Procedures and Methods

Microsomal Stability:

Test compound (1 µM) was incubated with pooled liver microsomes. Aliquots were taken at 0, 5, 15, 30, and 60 min and quenched immediately with two-volumes of ACN containing an internal standard (IS). The samples were extracted and analyzed by LC-MS/MS.

Experimental Procedure:

Reagents 0.5 M KPO$_4$, pH 7.4 (GAL-PAC, Sigma 936-4GP) or 1 M KH$_2$PO$_4$+1 M K$_2$HPO$_4$ (19 mL 1 M monobasic (Sigma P8709)+89 mL 1 M dibasic (Sigma P8584)+100 mL H$_2$O); 0.065 M MgCl$_2$, 6H$_2$O (Sigma M-0250) (1.33 g+100 mL H$_2$O); 10 mM NADPH (4Na) (8.33 mg/mL) (Sigma N7785); NADPH regenerating system Solution A: NADP (Sigma N0505) (2 g+10 mL H$_2$O)+glucose-6-phosphate (Sigma G7250) (2 g+10 mL H$_2$O) and Solution B: glucose-6-phosphate dehydrogenase (Sigma G6378) (14 unit/ml).

Materials 2 or 15 mL plastic cap tubes were used to make compound solutions and microsomal dilutions (mixtures 1 and 2); 20 mL scintillation vial was used for NADPH (mixture 3); removable well, 2 mL, 96 well plate was used for the incubation plate at 37 C; 2 mL NUNC 96 well plate for receiving plate.

Pooled liver microsomes for several species (mouse (lot BDS), rat (lot LMO), dog (lot LQU), and Cynomolgus monkey (lot DIS)) were purchased from In Vitro Technologies. Pooled human liver microsomes (male and female) were purchased from BD Gentest (lot 23). Microsomes were stored at −80° C. prior to use.

Microsomes (final concentration 0.5 mg/mL), 0.1M phosphate buffer pH 7.4, 6.5 mM $MgCl_2$, and test compound (final substrate concentration=1 µM; final DMSO concentration=0.2%) were pre-mixed prior to the addition of NADPH (final concentration=1 mM) to initiate the reaction. The final incubation volume was 600 µL. A control incubation was included for each compound tested where water was added instead of NADPH (minus NADPH). Testosterone was included with each incubation as a positive control. All incubations were performed in duplicate for each test compound.

50 µL aliquots were taken from each incubation at 0, 5, 15, 30 and 60 min, and added to 200 µL ACN containing internal standard to quench the reaction. The samples were then diluted with 100 µL 50/50 ACN/water, and the incubation plates were vortexed and centrifuged at 36000 rpm for 10 min at 4° C. to precipitate the protein.

Following protein precipitation, the sample supernatants were analyzed by LC-MS/MS.

Data Analysis:

The peak area ratio (compound peak area/internal standard peak area) was normalized to 100% using the time=0 min data and the natural log (ln) of the percent compound remaining was plotted against time. The slope of the line was determined using a linear fit and the elimination rate constant was calculated.

The elimination rate constant $(k)=(-\text{slope})$

From the above, half-life and intrinsic clearance was calculated using the following equations.

$$\text{Half life } (t_{1/2})(\text{min}) = \frac{0.693}{k}$$

$$\text{Intrinsic Clearance } (CL_{int})(\mu\text{L/min/mg protein}) = \frac{V \times 0.693}{t_{1/2}}$$

where V is a volume term expressed as µL/mg protein.

One to two control compounds were included in the assay to verify the enzymes were active. If the control compounds were not sufficiently turned over, the results were rejected.

Compound IA demonstrated low intrinsic clearance in mouse, rat, and human microsomal incubations. Clearance was modest in dog microsomes, and high in Cynomolgus monkey microsomes. The stability of Compound IA in all animal species tested is summarized in Table 1. Using a comparison of in vitro and in vivo clearance, human clearance can be predicted. The in vitro intrinsic clearance is influenced by animal weight, hepatic blood flow, relative liver weight, and amount of protein/liver weight. Therefore, the clearance calls for different species vary and are calculated using the above listed parameters for low and high extraction ratios (0.3 and 0.7, respectively). Human clearance is predicted to be low (Table 2).

TABLE 1

Compound IA Microsomal Stability.

| Species | Half-life (min) | Intrinsic Clearance (µL/min/mg) | Testosterone Half life (min) |
|---|---|---|---|
| Mouse | >60 | <23 | 6 |
| Rat | >60 | <23 | 4 |
| Dog | 33 | 42 | 60 |
| Monkey | 19 | 73 | 3 |
| Human | >60 | <23 | 11 |

Limit of calculation for intrinsic clearance is 23 µL/min/mg at 60 min.

TABLE 2

Species Comparison of in vitro and in vivo Clearance.

| | In Vivo | | In Vitro (Microsomes) | |
|---|---|---|---|---|
| | $t_{1/2}$ (hr) | Cl | $t_{1/2}$ (min) | Cl |
| Mouse | na | Low | >60 | Low |
| Rat | 6.9 | Low | >60 | Low |
| Dog | 6.1 | Modest | 24 | Med-High |
| Monkey | 2.7 | High | 19 | High |
| Human | na | Low | >60 | Low | na = not available

Metabolite Analysis:

For metabolism studies, Compound IA was incubated under similar conditions as described for microsomal stability with the following exceptions. Test compound concentration was increased to 10 µM with a concomitant increase in protein concentration (1 µM). The incubation time was 60 min.

Experimental Procedure:

Pooled liver microsomes for several species (mouse (lot BDS), rat (lot LMO), dog (lot LQU), and Cynomolgus monkey (lot DIS) were purchased from In Vitro Technologies. Pooled human liver microsomes (male and female) were purchased from BD Gentest (lot 23). Microsomes are stored at −80° C. prior to use.

Microsomes (final concentration 1 mg/mL), 0.1M phosphate buffer pH7.4, 6.5 mM $MgCl_2$, and test compound (final substrate concentration 10 µM; final DMSO concentration 0.2%) were pre-mixed prior to the addition of NADPH (final concentration 1 mM) to initiate the reaction. The final incubation volume was 200 µL. To quench the reaction, 400 µl, ACN was added. The samples were then vortexed and centrifuged at 36000 rpm for 10 min at 4° C. to precipitate the protein.

Following protein precipitation, the sample supernatants were analyzed by LC-MS using a 30 min LC gradient. Expected metabolites were searched for by their expected molecular ion (±1) using LC-MS/MS (multiple reaction monitoring, MRM). Unexpected metabolites were searched for using LC-MS enhanced mass spectrometry (EMS). Additionally, Precursor Ion Scans (PCI, m/z=308 and 421) and Constant Neutral Loss Scans (CNL, m=140) were collected for some samples. Tuning conditions were optimized on the parent molecule.

Two control samples (0 min time point and minus NADPH negative control) were run under the same analysis conditions to identify non-CYP mediated, non-parent products and/or contaminants.

The samples were analyzed using the following LC methods described below:

Column: Prodigy 150×2; 5 µm 30 min gradient (solvent A=0.05% Formic Acid, B=Acetonitrile+0.05% Formic Acid)

| Time | % B |
|---|---|
| 0 | 5 |
| 20 | 60 |
| 23 | 60 |
| 25 | 95 |
| 28 | 95 |
| 29 | 5 |
| 30 | stop |

MS/MS Method:
DP=96
CE=41
CXP=18

Data Analysis and Results:

Samples were analyzed utilizing a three step process. First, all LC-MS/MS fragments from the parent peak were identified. Secondly, the chromatograms from the two controls and active incubations were compared to exclude non CYP-mediated peaks. Finally, all metabolite peaks were analyzed by comparison of molecular weight and fragmentation products to determine the most likely transformation, and where possible, on which portion of the parent molecule the transformation occurred.

Compound IA metabolism in liver microsomes was evaluated in four species (rat, dog, Cynomolgus monkey, and human). The metabolic turnover was in agreement with the microsomal stability data. As such, turnover was very low for Compound IA in human and rat liver microsomes, modest in dog microsomes, and higher in Cynomolgus monkey microsomes, but in all cases turnover was not extensive.

Compound I-1 was isolated and identified as a metabolite of Compound IA in liver microsomes of human and Cynomolgus monkey and Compound I-2 was isolated and identified as a metabolite of Compound IA in liver microsomes of rat, dog, human and Cynomolgus monkey.

Conclusion

Compound IA demonstrated low intrinsic clearance in mouse, rat, and human microsomal incubations. Clearance was modest in dog microsomes, and high in Cynomolgus monkey microsomes. Likewise, metabolic turnover was in agreement with the microsomal stability data. As such, turnover was very low for Compound IA in human and rat liver microsomes, modest in dog microsomes, and higher in Cynomolgus monkey microsomes.

Example 2

Tissue Sample Preparation and Analysis

Study Procedures and Methods

Tissue sample preparation is described with respect liver tissue in this example. Similar procedures were used for studies with kidney samples.

Liver tissue slices were cut into smaller pieces by using a scalpel. Half-gram samples were then weighed into a 15 mL conical tubes. Nine volumes of water per gram of tissue was added (approximately 4.5 mL) to the tubes. The samples were homogenized thoroughly by the homogenizer. The homogenized samples were placed in a water bath sonicator for 60 min at 37 C. A 200 µL aliquot of sample was then transferred into a 2 mL tube and 800 mL of acetonitrile was added. The solutions were further sonicated for 20 min at 37 C, then centrifuged at 13,000 rpm for 15 min. 400 µL aliquots of the supernatant were transferred into LC vials for MS analyses using MRM-IDA, which identifies molecules by a series of intact molecule-to-fragment monitored transitions; Neutral Loss-IDA, which identifies molecules that have a common non-ionized fragment; and Precursor-IDA, which identifies molecules that have a common ionized fragment. LC parameters are described below.

In addition, 100 µL aliquots of the homogenate and the precipitate post extraction were placed onto glass slides for microscopic observation of birefringent crystals.

Finally, to determine if the crystals contained protein aggregates or small molecules, 200 µL aliquots of the homogenate containing crystals were incubated with either 800 µL of DMSO followed by 4 hours sonication or 800 L of 0.25 mg/100 mL trypsin (CellGro) followed by incubation at 37 C for 4 hours. 100 µL aliquots of the homogenates and the precipitates post extraction were placed on glass slides for microscopic observation of birefringent crystals.

LC Parameters:
Model: SPD-10Avp
Run Time: 30.00
Wavelength (Ch1): 298 nm
Lamp: D2
Polarity: Positive
Time Program: (Gradient)
Solvent A: 0.05% Formic Acid in Water
Solvent B: 0.05% Formic Acid in Acetonitrile

| Time  | Module            | Events | Parameter |
|-------|-------------------|--------|-----------|
| 0.05  | Pumps             | % B    | 5         |
| 2.00  | Pumps             | % B    | 30        |
| 25.00 | Pumps             | % B    | 75        |
| 26.00 | Pumps             | % B    | 95        |
| 28.00 | Pumps             | % B    | 95        |
| 29.00 | Pumps             | % B    | 5         |
| 30.00 | System Controller | Stop   |           |

Scan Type: MRM (MRM)
Polarity: Positive
Scan Mode: N/A
Ion Source Turbo Spray
Resolution Q1: Low
Resolution Q3: Low
Intensity Thres.: 0.00 cps
Settling Time: 0.0000 msec
MR Pause: 5.0070 msec
MCA: No
Step Size: 0.00 amu
CUR: 15.00
IS: 5200.00
TEM: 500.00
GS1: 50.00
GS2: 50.00
ihe: ON
CAD: 8.00
DP 96.00
EP 10.00
CE 41.00
CXP 12.00
Scan Type: Neutral Loss (NL)
Polarity: Positive
Scan Mode Profile
Ion Source Turbo Spray
Loss Of: 140.00 amu
Resolution Q1: Low
Resolution Q3: Low
Intensity Thres.: 0.00 cps
Settling Time: 0.0000 msec
MR Pause: 5.0070 msec
MCA: No
Center/Width: No
Step Size: 0.10 amu

| Start (amu) | Stop (amu) | Time (sec) |
|-------------|------------|------------|
| 150.00      | 800.00     | 1.00       |

Parameter Table (Period 1 Experiment 1)
CUR: 40.00
IS: 4500.00
TEM: 550.00
GS1: 60.00
GS2: 60.00
ihe: ON
CAD: 12.00
DP 96.00
EP 10.00
CE 41.00
CXP 12.00
Scan Type: Precursor Ion (Prec)
Polarity: Positive
Scan Mode Profile
Ion Source Turbo Spray
Precursor Of: 114.18 amu
Resolution Q1: Low
Resolution Q3: Low
Intensity Thres.: 0.00 cps
Settling Time: 0.0000 msec
MR Pause: 5.0070 msec
MCA: No
Center/Width: No
Step Size: 0.10 amu

| Start (amu) | Stop (amu) | Time (sec) |
|---|---|---|
| 300.00 | 900.00 | 1.00 |

Parameter Table (Period 1 Experiment 1)
CUR: 40.00
IS: 4500.00
TEM: 550.00
GS1: 60.00
GS2: 60.00
ihe: ON
CAD: 12.00
DP 96.00
EP 10.00
CE 61.00
CXP 6.00

The following metabolites were identified in dog liver samples:

| Compound | Δ Mass | Retention time (min) | MRM transition Q1/Q3 |
|---|---|---|---|
| Compound IA | | 11.40 | 561.2/421.1 |
| Compound I-1 | P + 16 | 6.93/12.22 | 577.2/421.1 |
| Compound I-2 | | 15.36 | |
| Compound I-4 | P + 32 | 7.49/9.80 | 593.2/421.1 |
| Compound I-5 | P + 30 | 7.09/9.76 | 591.2/421.1 |
| Compound I-6 | P + 176 | 6.44 | 737.2/421.1 |
| Compound I-7 | P + 305 | 12.22 | 866.3/421.1 |

The following metabolites were identified in rat kidney samples:

| Compound | Δ Mass | Retention time (min) | MRM transition Q1/Q3 |
|---|---|---|---|
| Compound IA | | 11.97 | 561.2/421.1 |
| Compound I-1 | P + 16 | 9.06/12.55 | 577.2/421.1 |
| Compound I-4 | P + 32 | 9.71 | 593.2/421.1 |
| Compound I-5 | P + 30 | 9.23 | 591.2/421.1 |

Example 3

Metabolism of Compound IA in Human Urine and Plasma

Urine Analysis

The following stock solutions were used in the analysis:
A1. STOCK 2 mg/mL (free base) in DMSO.
A2. STOCK 0.1 mg/mL in DMSO (50 µL of 2 mg/mL stock+950 µL DMSO)

Standard curve and QC's in urine were prepared as follows:
1. Standard: 1000 ng/mL (10 µL of 0.1 mg/mL solution (A2 above)+990 µL of urine). Vortex immediately.
2. QC 800 ng/mL (8 µL of 0.1 mg/mL solution (A2 above)+992 µL of urine). Vortex immediately.

Serial dilutions of standards and QCs were prepared as follows:
1. Pipet 600 µL diluent (control urine) into wells A2-12, B2-B4, and B6-12.
2. Pipet 600 µL STD 1000 into well A1.
3. Pipet 600 µL QC 800 into wells B1 and B5.
4. Standards-1:1 dilution of STD+urine to make STD 500, 250, 125, 62.5, 31.25, 15.6, 7.8 ng/mL (i.e. add 600 µL of STD1000 to 600 µL of control urine in well A2 for STD500, etc.) Note: serial dilutions only go to well A9. Wells A10-A12 are blank urine.
5. QCs-1:3 (four-fold) dilution of QC+urine to make QC 200 ng/mL, QC 50 ng/mL, and QC 12.5 ng/mL (i.e. add 200 µL of QC 800 to 600 µL of control urine in wells B2 & B6 for QC200). Note: QC dilutions only go to well B8. Wells B9-B12 are blank urine.

Sample preparation and addition of Internal Standard was conducted as follows:
1. Transfer 500 µL from rows A and B (standard curve, QC, and blank urine) to a fresh 96 well plate.
2. Add 500 µL of patient sample(s) to row C—H as needed and 500 µL of water to any remaining wells.
3. Add 100 µL of internal standard (AC012168 or current DMPK standard 25 ng/mL in acetonitrile) to each well. Mix.

Urine samples were extracted as follows:
Prepare Biotage Isolute C18(EC) 25 mg 96 well plate as follows
1. Add 5 µL/well of methanol. Allow the plate to sit for 1 minute and then remove methanol using brief (5-10 seconds) vacuum (<5" Hg).
2. Add 250 µL/well of water. Allow the plate to sit for 1 minute and then remove the water using brief vacuum. The plate is now ready for samples.
1. Load the prepared plate with 250 µL of samples (standard curve, QC, patient samples, etc.) containing the internal standard. Add 250 µL of water to any unused wells.
2. Let samples sit for 1 minute then remove urine under brief vacuum.
3. Wash samples with water, 250 µL/well. Let samples sit for 1 minute then remove water under brief vacuum.

4. Elute off Compound IA using 2×250 µL washes with methanol. For first wash, add 250 µL/well methanol. Let sit for 1 minute the collect eluant under brief vacuum. For second wash, add 250 µL/well methanol and allow to sit for 4 minutes (with the collection plate from wash 1 still in place). After 4 minutes apply brief vacuum.

Samples were analyzed using Shimadzu LC system with the following parameters:
Model: SPD-10Avp
Wavelength (Ch1): 254 nm
Lamp: D2
Polarity: Positive
Period 1 Experiment 1:
Scan Type: MRM (MRM)
Polarity: Positive
Scan Mode: N/A
Ion Source Turbo Spray
Resolution Q1: Low
Resolution Q3: Low
Intensity Thres.: 0.00 cps
Settling Time: 0.0000 msec
MR Pause: 5.0070 msec
MCA: No
Step Size: 0.00 amu
Parameter Table (Period 1 Experiment 1)
CUR: 15.00
IS: 5200.00
TEM: 500.00
GS1: 50.00
GS2: 50.00
ihe: ON
CAD: 8.00
DP 96.00
EP 10.00
CE 41.00
CXP 12.00
Period 1 Experiment 2:
Scan Type Enhanced Product Ion (EPI)
Polarity: Positive
Scan Mode: Profile
Ion Source: Turbo Spray
Scans to Sum: 1
Product Of: 30.00 amu
Resolution Q1: Unit
Scan Rate: 4000 amu/s
Intensity Thres.: 0.00 cps
Settling Time: 0.0000 msec
MR Pause: 5.0070 msec
Q0 trapping: Yes
MCA: No
Center/Width: No
LIT fill time: 20.00 msec
Q3 Entry Barrier: 8.00 V
Step Size: 0.12 amu
Parameter Table (Period 1 Experiment 2)
CUR: 15.00
CAD: High
IS: 5200.00
TEM: 500.00
GS1: 50.00
GS2: 50.00
ihe: ON
DP 96.00
CES 17.00
CE 57.00

Time Program: (Gradient)
Solvent A: 0.05% Formic Acid in Water
Solvent B: 0.05% Formic Acid in Acetonitrile

| Time | Module | Events | Parameter |
|---|---|---|---|
| 0.01 | Pumps | % B | 5 |
| 25.00 | Pumps | % B | 50 |
| 26.00 | Pumps | % B | 50 |
| 27.00 | Pumps | % B | 95 |
| 28.00 | Pumps | % B | 95 |
| 29.00 | Pumps | % B | 5 |
| 30.00 | System Controller | Stop | |

Metabolites identified in human urine samples include compounds of formula I-1, I-3, I-5, and I-6. The LC retention times of the compounds are as follows:

| Compound | Δ Mass | Retention time (min) | MRM transition Q1/Q3 |
|---|---|---|---|
| Compound IA | | 16.5 | 561.2/421.1 |
| Compound I-1 | P + 16 | 12.3 | 577.2/421.1 |
| Compound I-3 | P − 12 | 17.5 | 549/409 |
| Compound I-5 | P + 30 | 12.6 | 591/421 |
| Compound I-6 | P + 176 | 10.3 | 737/421 |

Plasma Analysis

Human plasma samples were taken from two patients to whom Compound IA was administered in the 60 mg and 90 mg cohorts. The plasma samples were combined by cohort and then extracted with acetonitrile. The samples were analyzed on a Sciex 4000 Q-Trap LC/MS/MS system. Standard expected and non-predicted metabolites were scanned for using a combination of Multiple Reaction Monitoring (MRM), Pre-curser Ion (PCI, m/z=114, 421, and 130), and Constant Neutral Loss (CNL, m=140 and 156) MS transitions. These different scans provide a fairly comprehensive overview of the putative metabolites of Compounds IA.

Study Procedures And Methods

Plasma samples were combined by cohort; 25 µL each from patient in the 60 mg and 90 mg cohorts. The combined samples and blank human plasma were extracted with 200 µL acetonitrile, vortexed, and placed in the centrifuge for 20 minutes. The resulting supernate was analyzed on a Sciex 4000 Q-Trap LC/MS/MS system using a 30 minute LC gradient with 20 µL injections. Tuning conditions were optimized on the parent molecule. The protocol and scan conditions are described below.

Samples were analyzed by LC-MS as described above using the following parameters:
LC Parameters:
Model: SPD-10Avp
Run Time: 30.00
Wavelength (Ch1): 254 nm
Lamp: D2
Polarity: Positive
Time Program: (Gradient)
Solvent A: 0.05% Formic Acid in Water
Solvent B: 0.05% Formic Acid in Acetonitrile

| Time | Module | Events | Parameter |
|---|---|---|---|
| 0.5 | Pumps | % B | 5 |
| 25.00 | Pumps | % B | 75 |
| 26.00 | Pumps | % B | 95 |
| 28.00 | Pumps | % B | 95 |
| 29.00 | Pumps | % B | 5 |
| 30.00 | System Controller | Stop | |

Metabolites identified in human plasma include compounds of formula I-1 and Compound I-7. The LC retention times of the compounds are as follows:

| Compound | Δ Mass | Retention time (min) | MRM transition Q1/Q3 |
|---|---|---|---|
| Compound IA | | 11.8 | 561.2/421.1 |
| Compound I-1 | P + 16 | 9.13 | 577.2/421.1 |
| Compound I-7 | P + 305 | 12.99 | |

Figure 2:
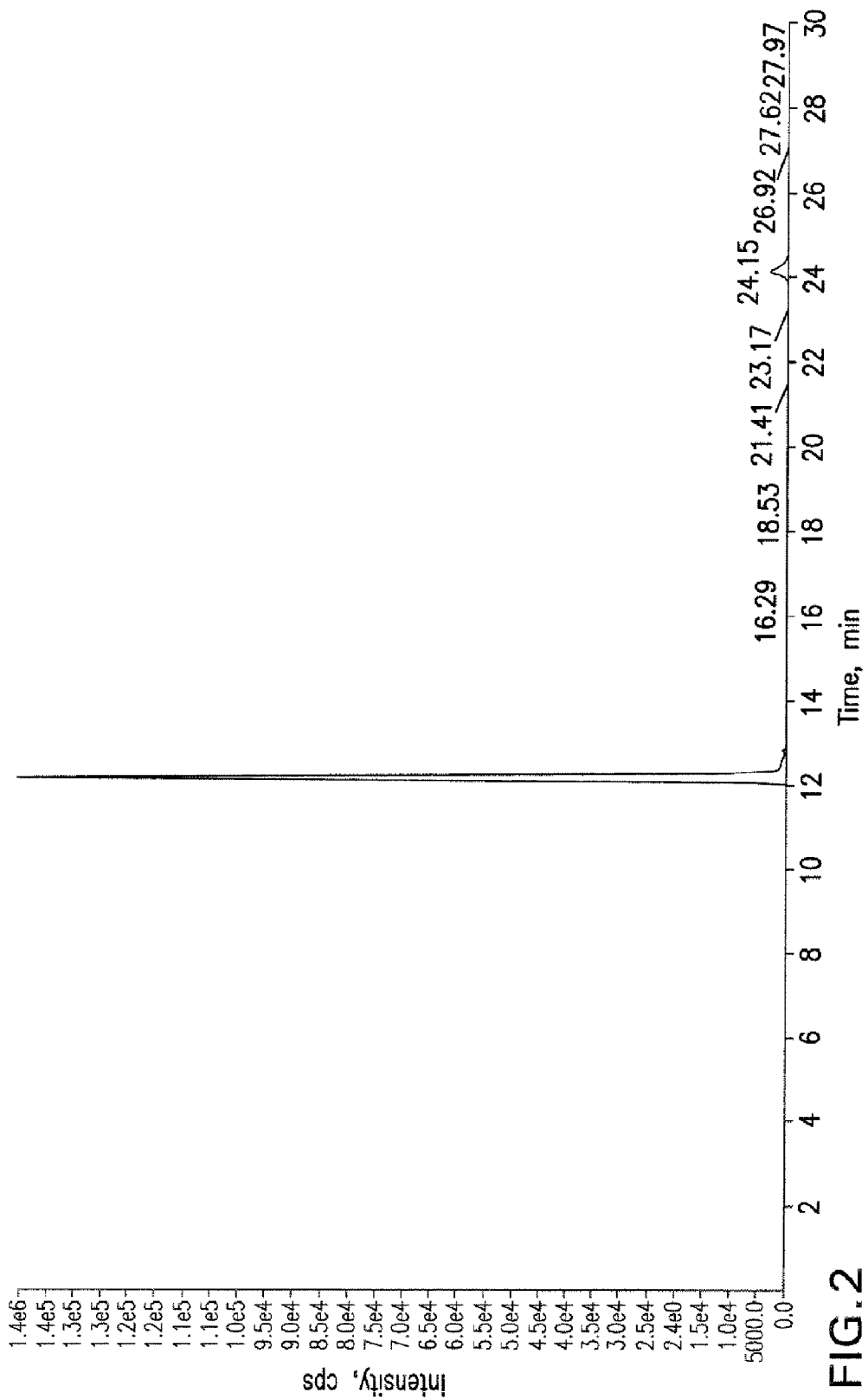
FIG. 2 illustrates extracted ion chromatogram (XICs) for 577/421 transition in the MRM scan for synthesized Compound I-1.
Figure 3:
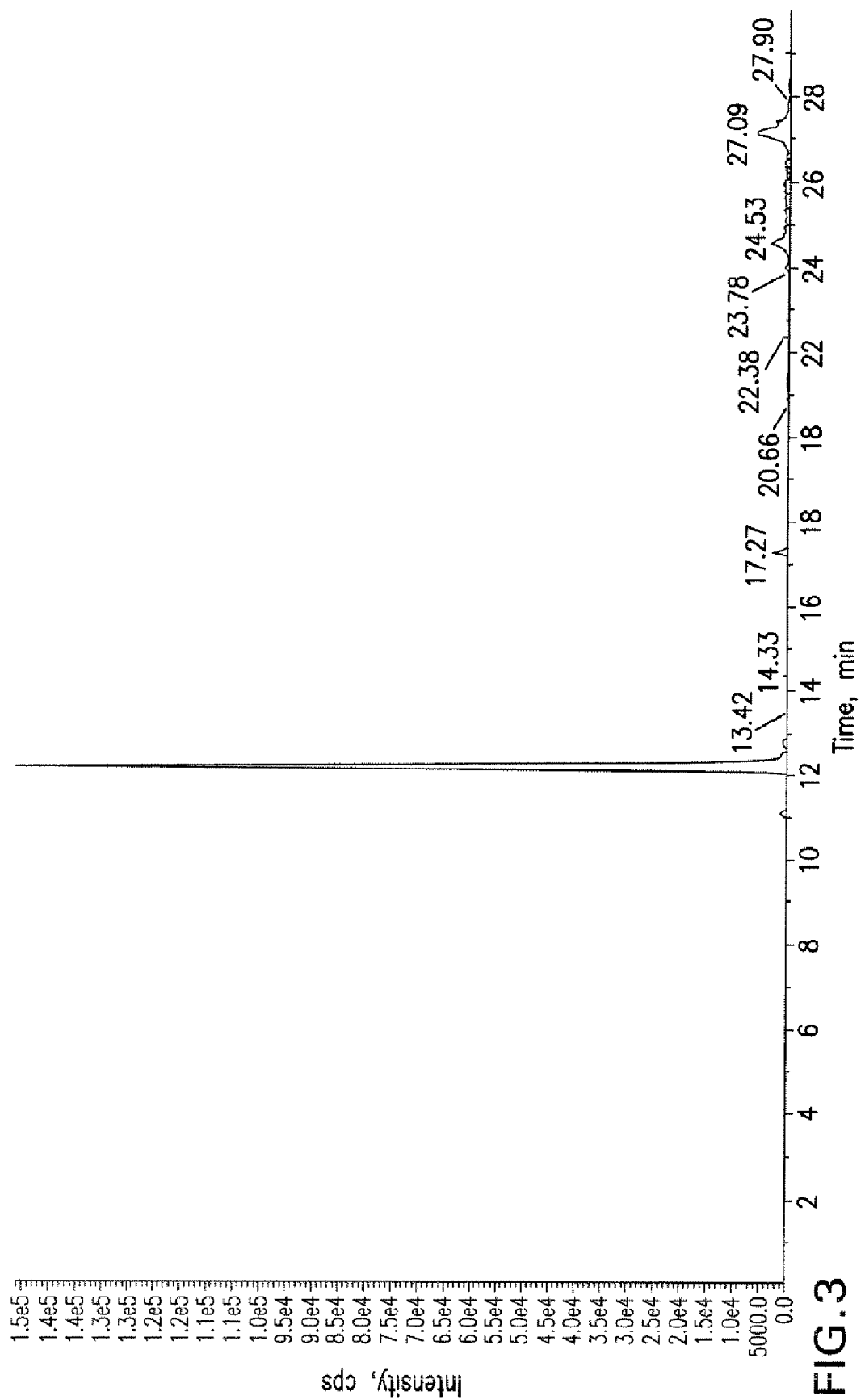
FIG. 3 illustrates extracted ion chromatogram (XICs) for 577/421 transition in the MRM scan for Compound I-1 isolated from human plasma sample.
Figure 4:
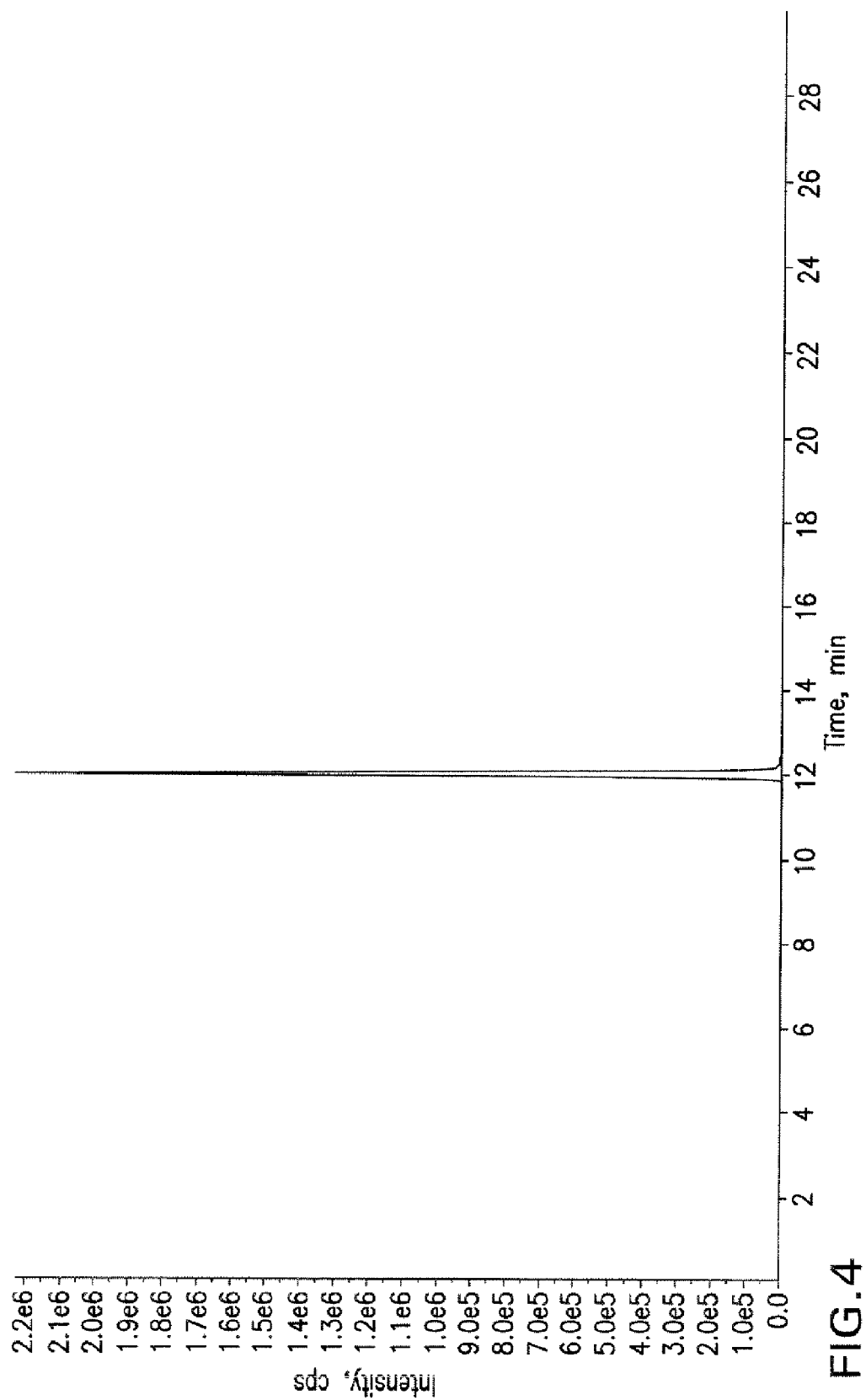
FIG. 4 illustrates extracted ion chromatogram for 577/421 transition in the MRM scan for a sample of Compound I-1 isolated from human plasma sample spiked 1:1 with 1000 ng/m synthesized Compound I-1.

Preliminary identification of Compound I-1 was conducted by comparing the retention time of Compound I-1 isolated as metabolite from plasma samples with retention times obtained with chemically synthesized standards (synthesis described in Example 4) using the chromatography conditions described above. FIGS. 2 and 3 illustrate extracted ion chromatograms (XICs) for 577/421 transition in the MRM scan for synthesized Compound I-1 and isolated Compound I-1, respectively. FIG. 4 illustrates extracted ion chromatogram for 577/421 transition in the MRM scan for a sample of Compound I-1 spiked 1:1 with 1000 ng/m synthesized Compound I-1.

Figure 5:
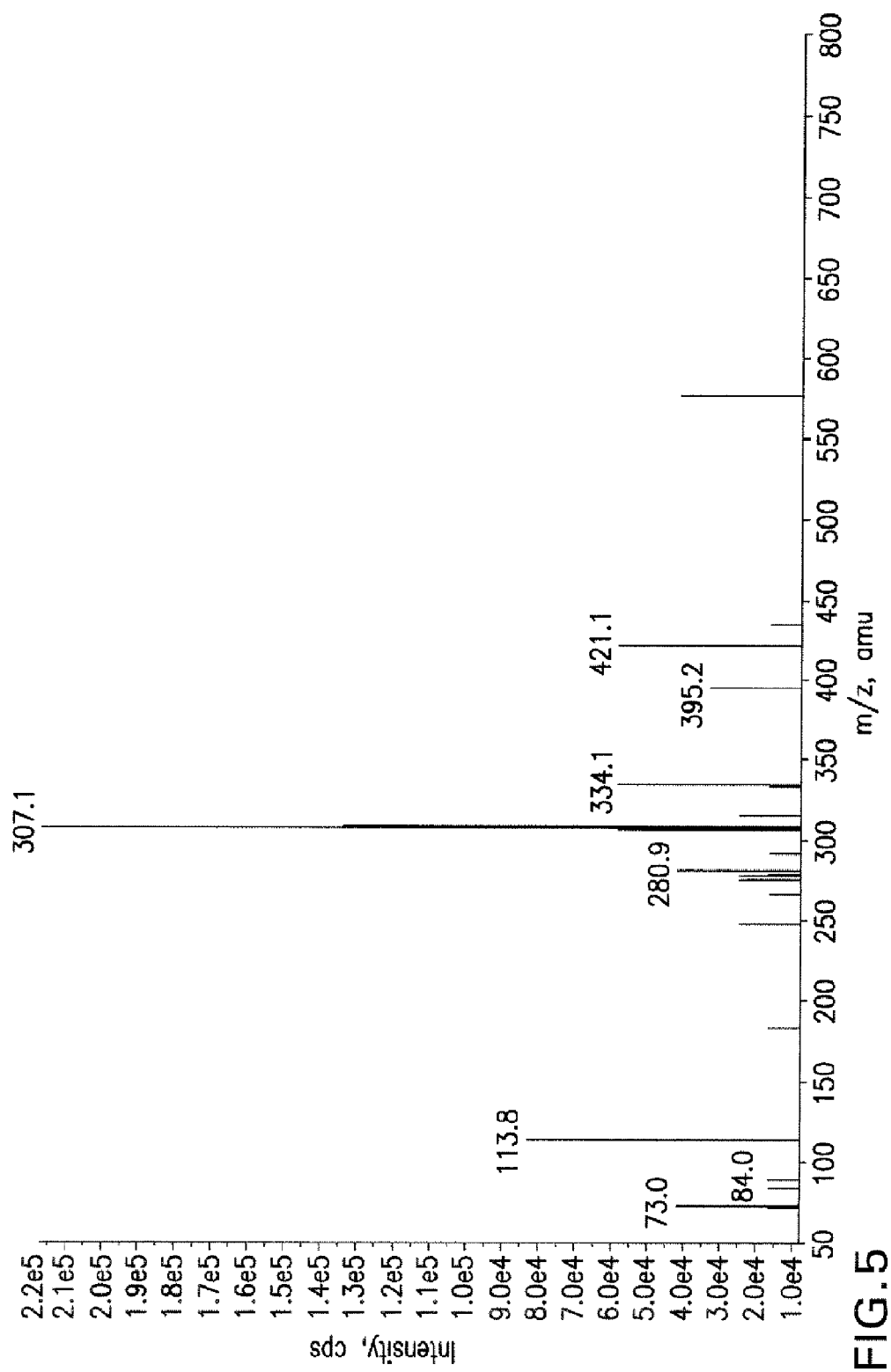
FIG. 5 illustrates the enhanced product ion scan for synthesized Compound I-1
Figure 6:
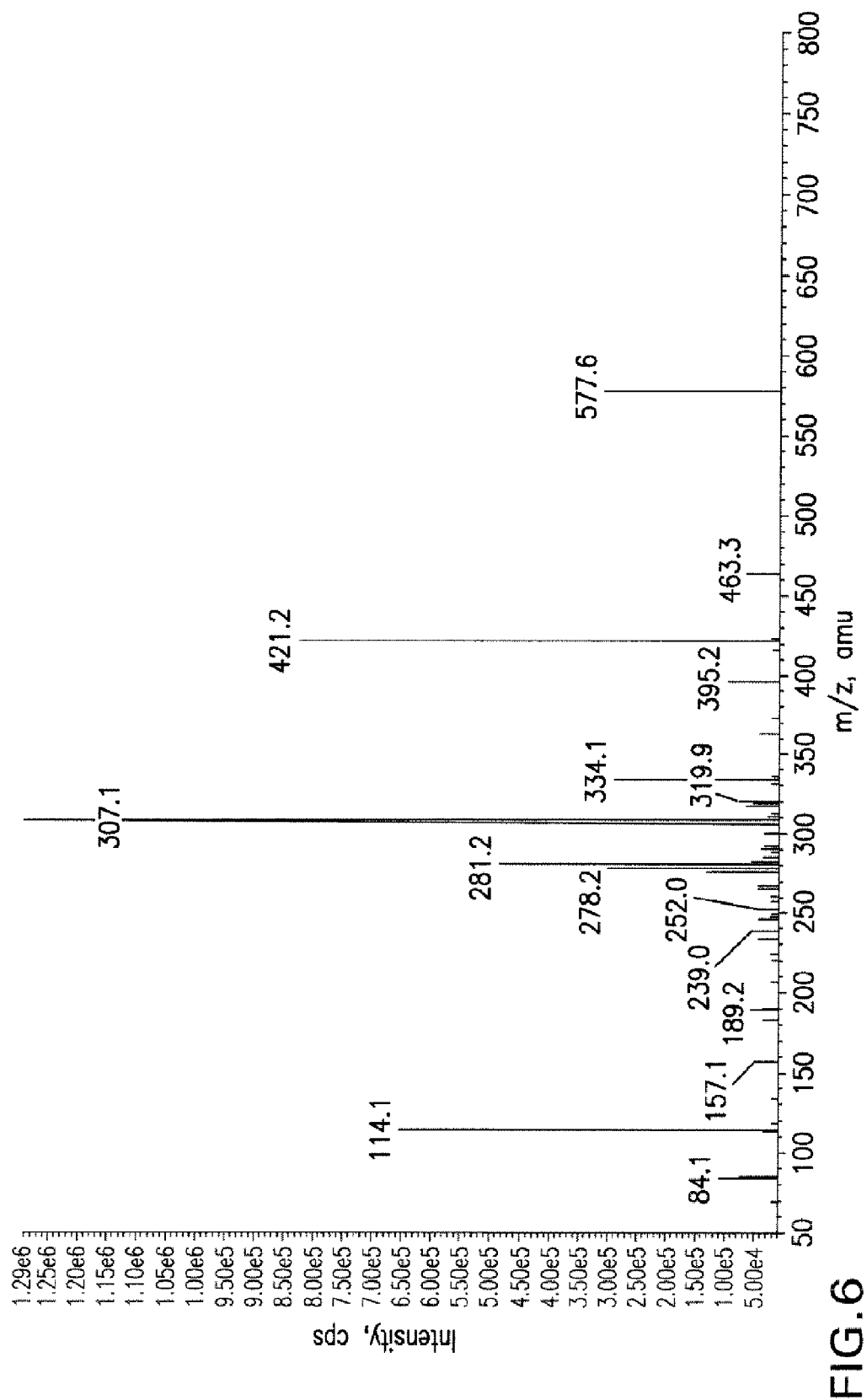
FIG. 6 illustrates the enhanced product ion scan for isolated Compound I-1 isolated from human plasma.
Figure 7:
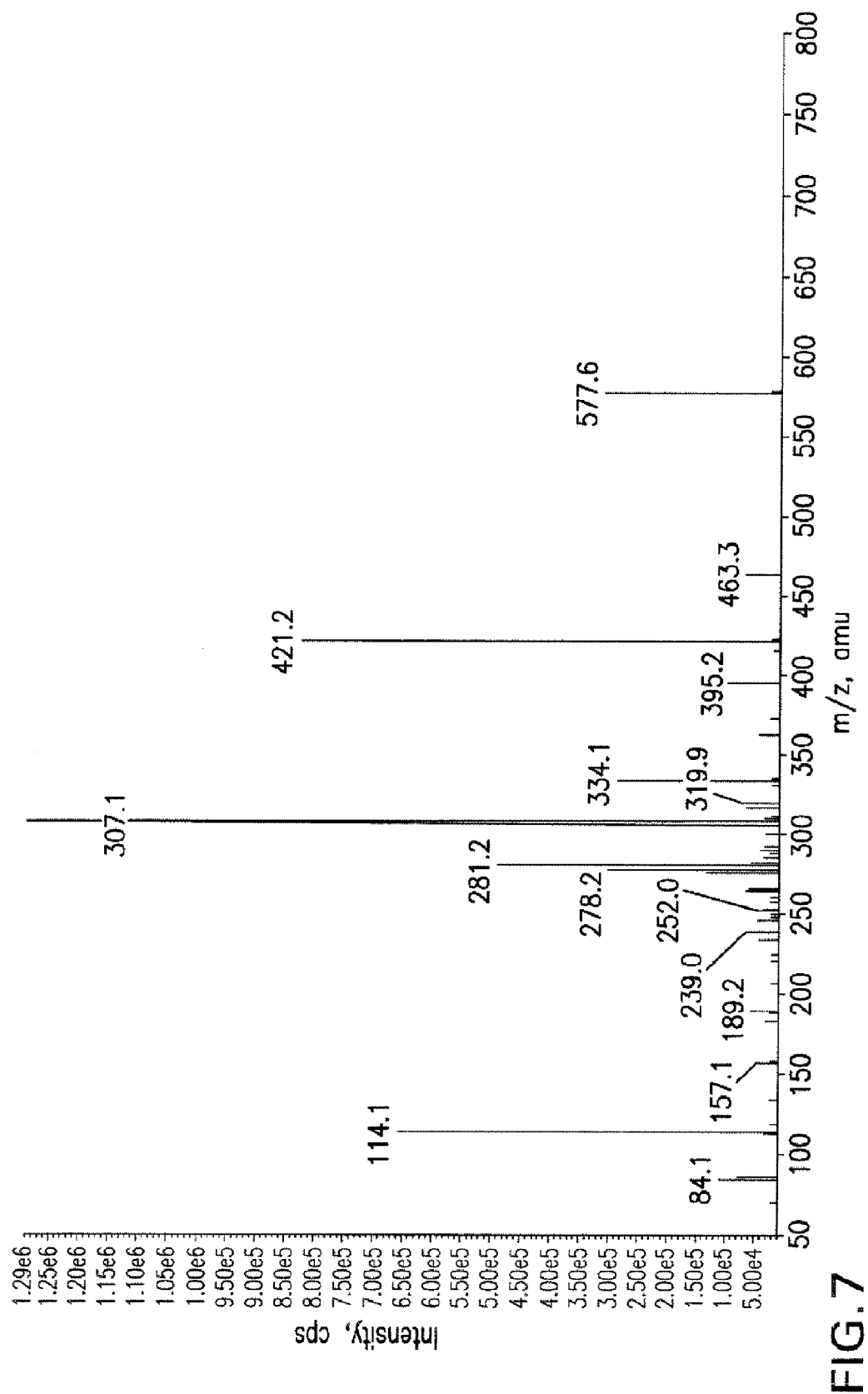
FIG. 7 illustrates extracted ion chromatogram for a sample of Compound I-1 isolated from human plasma spiked with synthesized Compound I-1.
Figure 8:
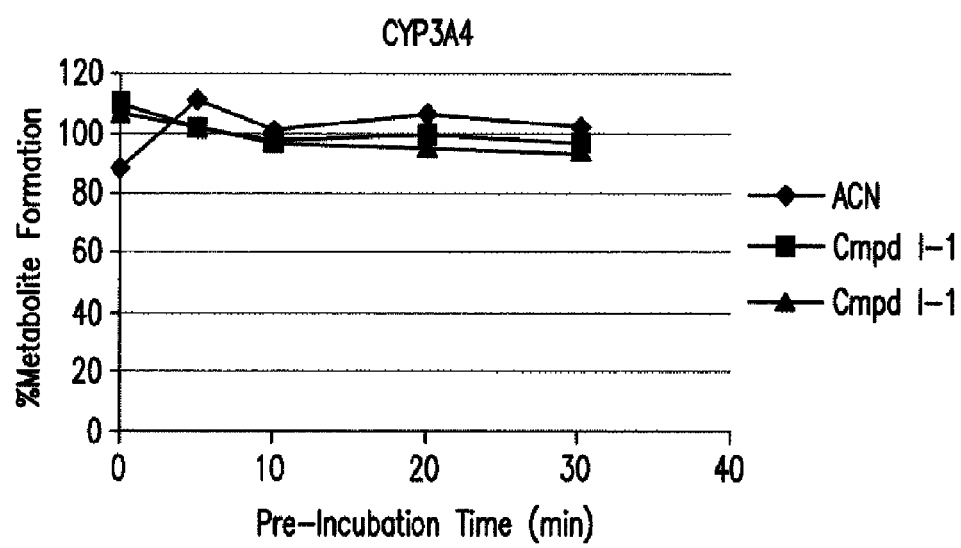
FIG. 8 demonstrates time dependant inhibition of CYP3A4 by Compound I-1.
Figure 9:
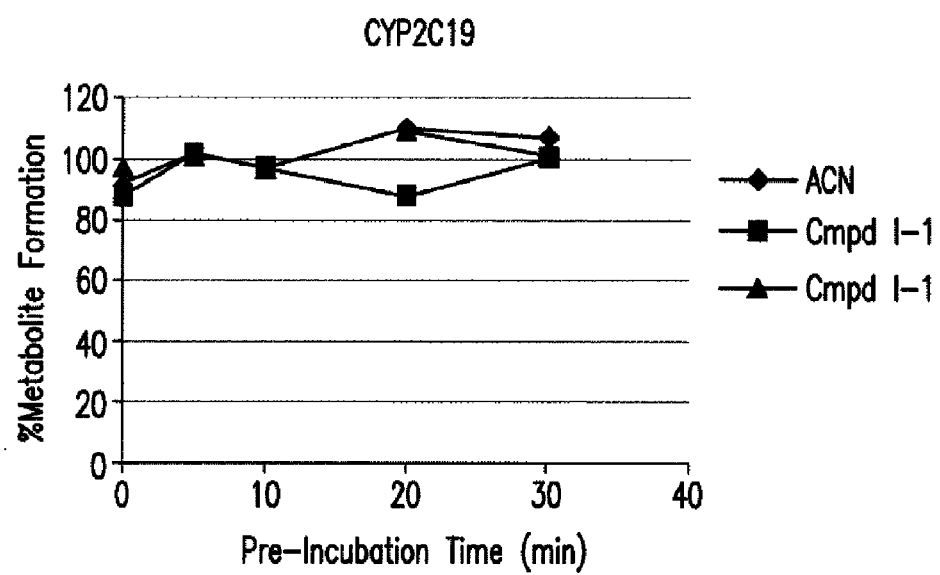
FIG. 9 demonstrates time dependant inhibition of CYP2C19 by Compound I-1.
Figure 10:
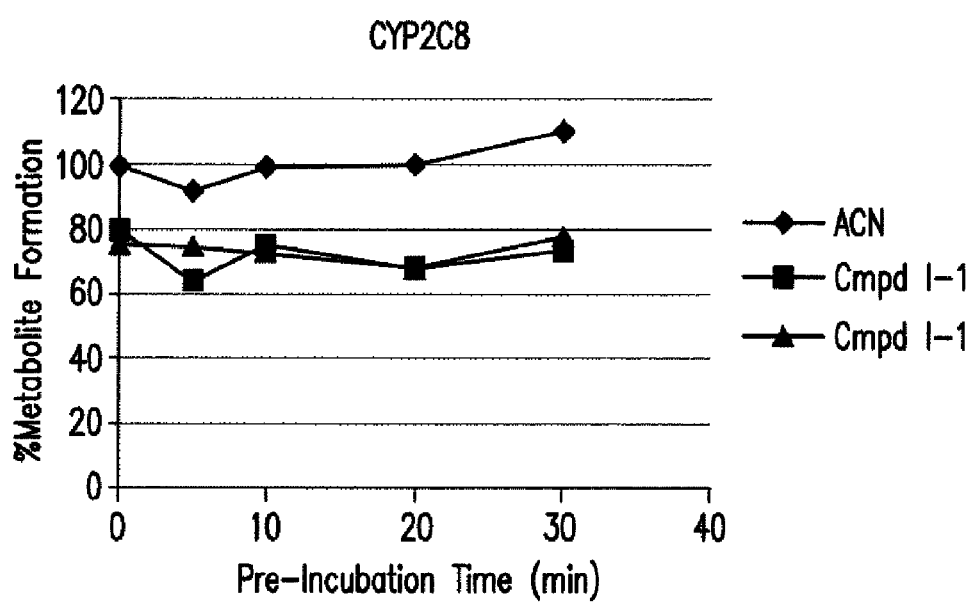
FIG. 10 demonstrates time dependant inhibition of CYP2C8 by Compound I-1.

Further identification of Compound I-1 was carried out by comparing enhanced product ion scans of Compound I-1 isolated as metabolite from plasma samples and chemically synthesized Compound I-1. FIGS. 5 and 6 illustrate the enhanced product ion scans for synthesized Compound I-1 and isolated Compound I-1, respectively. FIG. 7 illustrates extracted ion chromatogram for a sample of Compound I-1 spiked synthesized Compound I-1.

Example 4

Preparation of Compound I-1

Procedure A: Preparation of 2-Amino-6-hydroxybenzothiazole

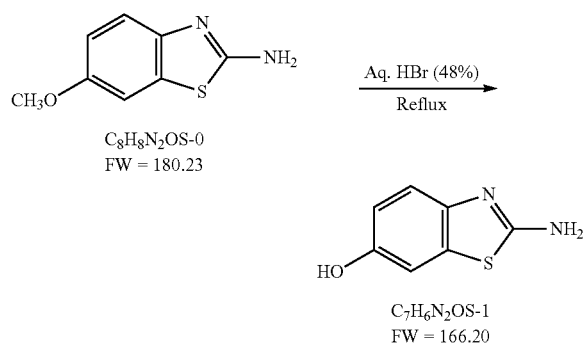

1. A 22 L 3-neck round bottom flask was equipped with a mechanical agitator, thermocouple probe, reflux condenser, and a heating mantle.

2. The flask was charged with 48% hydrobromic acid (14 L, 123.16 mol, 13.10 eq). The heating was initiated and 2-amino-6-methoxybenzothiazole was added (1.7 Kg, 9.4 mol, 1.00 eq) with stirring over 10 minutes.

3. The heating of the reaction mixture was continued to reflux, and maintained (≥107° C.) for approximately 5 hours. The reaction mixture turned into a clear solution between 75° C. and 85° C.

4. The reaction progress was monitored by TLC until no starting material was observed [5% Methanol/Dichloromethane; $R_f$(product)=0.35; $R_f$ (starting material)= 0.40]. For preparation of samples for TLC analysis, a ~0.5 mL reaction mixture aliquot was diluted with ~0.5 mL of water as a clear solution, neutralized with sodium acetate to pH ~5 and extracted with 1 mL of dichloromethane; the organic layer was spotted 5. The reaction mixture was cooled to ~20° C. (overnight). White solids precipitated. The solids were filtered onto a polypropylene filter and pressed to remove as much of the hydrobromic acid from the solids as possible.

6. The slightly wet crude product was dissolved in hot (50° C.) water (5 L). The clear solution was filtered to remove the any insoluble material present. The solids were washed with 50° C. water. then the filtrated was cooled to 10° C.

7. The cooled filtrate was neutralized with sodium acetate (~1.0 Kg) to pH 4.5 to 5.5 with vigorous stirring. A thick white solid precipitated. The solids were collected by filtration, and washed with cool (~10° C.) water (2×1.0 L) and air dried.

8. The wet crude product was briefly slurried in hot (50° C.) isopropanol (3 L) and allowed to stand in a cool room (~5° C.) overnight. The solids were collected by filtration and washed with methyl tert-butylether (2×500 mL).

9. The solids were dried in a vacuum oven overnight (<30 mmHg) at 30° C., (first lot).

10. Secondary crop: The organic filtrate was collected to a total volume of 1.0 L, cooled to 10° C., and the off-white solids were collected by filtration.

11. The solids were dried in a vacuum oven overnight (<30 mmHg) at 30° C., (second lot).

First Lot:
Yield: 1068 g (68%), white solid.
HPLC: 99.4% (area)
$^1$H NMR: conforms (300 MHz, DMSO)
Second Lot:
Yield: 497 g (32%), off-white solid.
HPLC: 99.8% (area)
Overall Yield: 1565 g, (99%)

Procedure B: Preparation of 2-(4-Nitrophenyl)imidazo[2,1-b]benzothiazol-7-ol) (2)

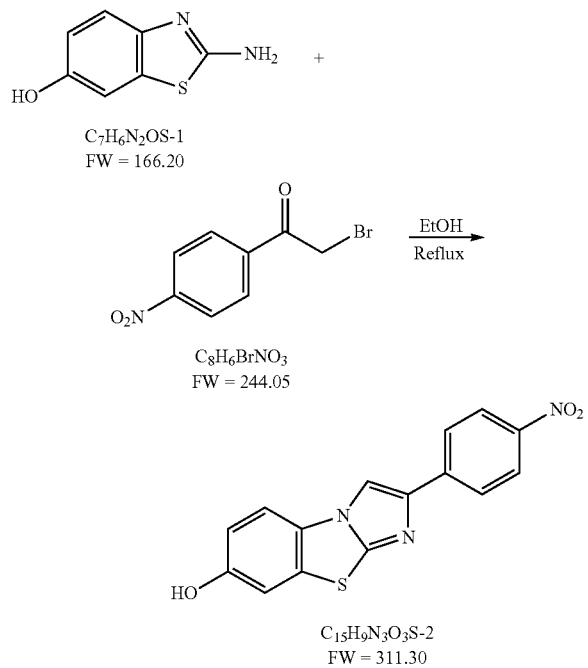

TABLE 3

| Materials: | |
|---|---|
| 2-Amino-6-hydroxybenzothiazole: | 1068 g, 6.43 mol, 1.0 eq |
| 2-Bromo-4-nitroacetophenone: | 1667 g (95%), 6.49 mol, 1.01 eq |
| Ethanol (200 Proof): | 32.0 L |
| Tetrabutylammonium iodide: | 10 g |

1. 50 L 3-neck round bottom flask was equipped with a mechanical agitator, thermocouple probe, reflux condenser, and a heating mantle.
2. The flask was charged with 2-amino-6-hydroxybenzothiazole (1068 g, 6.43 mol, 1.0 eq) and ethanol (200 pf., 32.0 L) and the suspension was stirred for 10 minutes.
3. 2-Bromo-4-nitroacetophenone (1667 g, 6.49 mol, 1.01 eq) was added in one portion.
4. The reaction mixture was heated to reflux (78° C.). Reflux was maintained for approximately 25 hours, resulting in a yellow suspension.
5. The reaction progress was monitored by TLC: [20% methanol/ethyl acetate; $R_f$ (product)=0.85; $R_f$ (starting material)=0.30]. TLC indicated ~50% starting material after 24 hours of reflux.
Tetrabutylammonium iodide (10 g) was added and reflux was maintained for an additional 12 hours, TLC indicated still ~50% starting material present. Coupling was seen to occur at both the thiazole and the amine.
6. The reaction mixture was cooled to 0-5° C. The solids were collected by filtration, washing the yellow solid with ethanol, 200 pf. (2×1.0 L) and diethyl ether (2×1.5 L).
7. The solids were dried in a vacuum oven (<10 mmHg) at 40° C.

Yield: 930 g (46%), yellow solid.
HPLC: 99.5% (area)
$^1$H NMR: conforms (300 MHz, DMSO)

Alternatively, the reaction may be carried out in the presence of a base, for example, in the presence of one or more carbonate or bicarbonate salt. For example, sodium bicarbonate is added to a mixture of 2-amino-6-hydroxybenzothiazole and 2-bromo-4-nitroacetophenone in a suitable solvent such as ethanol, isopropanol or n-butanol, and the resulting mixture is stirred at a suitable temperature, for example, to reflux and maintained at reflux (110-115° C.) for 2-3 h or until the reaction is substantially complete.

Procedure C: Preparation of 7-(2-Morpholin-4-yl-ethoxy)-2-(4-nitrophenyl)imidazo[2,1-b]benzothiazole (3)

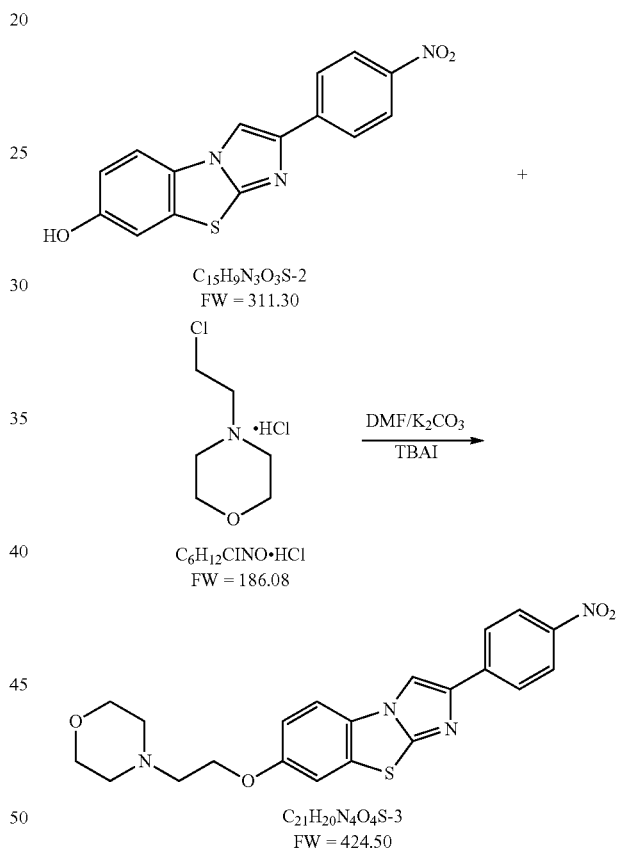

TABLE 4

| Materials: | |
|---|---|
| 2-(4-Nitrophenyl) imidazo[2,1-b]benzothiazol-7-ol: | 1.770 Kg, 5.69 mol, 1.0 eq |
| 4-(2-Chloroethyl)morpholine hydrochloride: | 2.751 Kg, 14.78 mol, 2.6 eq |
| Potassium carbonate: | 2.360 Kg, 17.10 mol, 3.0 eq |
| Tetrabutylammonium iodide: | 0.130 Kg, 0.36 mol, 0.06 eq |
| N,N-Dimethylformamide: | 18.0 L |

1. A 50 L 3-neck round bottom flask was equipped with a mechanical agitator, thermocouple probe, drying tube, reflux condenser, and a heating mantle.

2. The flask was charged with 2-(4-nitrophenyl)imidazo[2,1-b]benzothiazol-7-ol (1.770 Kg), N,N-dimethylformamide (18.0 L), 4-(2-chloroethyl)morpholine hydrochloride (2.751 Kg), potassium carbonate (2.360 Kg) and tetrabutylammonium iodide (0.130 Kg) with stirring.
3. The resulting yellow suspension was heated to 90° C. to 95° C., maintaining the temperature for approximately 5 hours.
4. The reaction was monitored by TLC until no starting material was observed. (20% methanol/ethyl acetate; $R_f$(product)=0.15; $R_f$(starting material)=0.85).
5. The reaction mixture was cooled to ~10° C., the yellow solids collected by filtration onto a polypropylene filter pad. The solids were slurried in water (2×5 L) and filtered.
6. The crude wet product was slurried in acetone (5 L), filtered and the solids rinsed with acetone (2×1.5 L).
7. The solids were dried in a vacuum oven (<10 mmHg) at 45° C.

Yield: 2.300 Kg (95%), yellow solid.

TLC: $R_f$=0.15 (20% methanol/EtOAc)

HPLC: 95.7% (area)

$^1$H NMR: conforms (300 MHz, DMSO)

TABLE 5

7-(2-Morpholin-4-yl-ethoxy)-2-(4-nitrophenyl) imidazo [2,1-b]benzothiazole lot summary

| 2-(4-Nitrophenyl) imidazo [2,1-b]benzothiazol-7-ol | 4-(2-Chloroethyl) morpholine hydrochloride | Yield | Yield % | HPLC (% A) |
|---|---|---|---|---|
| 0.004 Kg | 0.007 Kg | 0.005 Kg | 91% | 98.4% |
| 0.140 Kg | 0.217 Kg | 0.170 Kg | 90% | 98.2% |
| 0.110 Kg | 0.170 Kg | 0.140 Kg | 93% | 97.0% |
| 0.170 Kg | 0.266 Kg | 0.220 Kg | 95% | NA |
| 0.930 Kg | 1.446 Kg | 1.220 Kg | 96% | 98.8% |
| 1.770 Kg | 2.751 Kg | 2.300 Kg | 95% | 95.7% |

Procedure D Preparation of 7-(2-Morpholin-4-yl-ethoxy)-2-(4-aminophenyl)imidazo[2,1-b]benzothiazole (4)

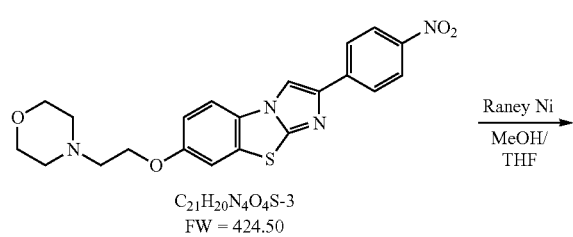

$C_{21}H_{20}N_4O_4S$-3
FW = 424.50

Raney Ni
MeOH/THF

-continued

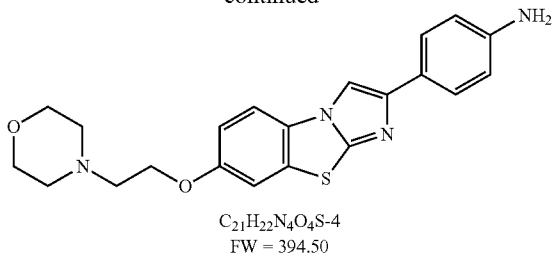

$C_{21}H_{22}N_4O_4S$-4
FW = 394.50

TABLE 6

| Materials: | |
|---|---|
| 7-(2-Morpholin-4-yl-ethoxy)-2-(4-nitrophenyl) imidazo [2,1-b]benzothiazole: | 580 g, 1.37 mol, 1.0 eq |
| Hydrogen ($H_2$): | As required at 150 psi |
| Raney Nickel: | ~55 g |
| Tetrahydrofuran (THF): | 7.5 L |
| Methanol (MeOH,AR): | 7.5 L |

1. Into a 5 gallon autoclave were added 7-(2-morpholin-4-yl-ethoxy)-2-(4-nitrophenyl) imidazo[2,1-b]benzothiazole (580 g), THF (7.5 L), methanol, AR (7.5 L) and Raney nickel catalyst (~55 g, weighed on balance total weight-removed Raney Ni with minimum water).
2. The reaction vessel was purged with nitrogen (3×50 psi) and hydrogen (2×50 psi), with stirring briefly under pressure and then venting.
3. The autoclave was pressurized with hydrogen (150 psi).
4. The mixture was stirred and the hydrogen pressure was maintained at 150 psi for over 24 hours with repressurization as necessary.
5. The reaction progress was monitored by TLC [10% methanol/chloroform plus 1 drop ammonium hydroxide; $R_f$(product) 0.20; $R_f$(7-(2-morpholin-4-yl-ethoxy)-2-(4-nitrophenyl)imidazo[2,1-b]benzothiazole) 0.80]. Reaction was complete when the TLC indicated no starting material present, typically after 24 hours of stirring at 150 psi. Hydrogenation was continued at 150 psi for a minimum of 4 hours or until complete if 7-(2-morpholin-4-yl-ethoxy)-2-(4-nitrophenyl)imidazo[2,1-b]benzothiazole was still present.
6. The reaction mixture was filtered through a Buchner funnel equipped with a glass fiber filter topped with a paper filter. Any un-reacted starting material was removed together with the catalyst.
7. The filtrate was concentrated to a total volume of 0.5 L, and the residue was triturated with methyl tert-butyl ether (0.5 L). The resultant solids were collected by filtration, washed with methyl tart-butyl ether (0.3 L).
8. Secondary crop: the filtrate was concentrated to dryness and the residue was diluted with methyl tart-butyl ether (2 L). The resultant solids were collected by filtration, washing with methyl tart-butyl ether (0.5 L).
9. The solids were dried in a vacuum oven (<10 mmHg) at 25° C.

Yield: 510 g (95%), beige solid.

TLC: $R_f$ 0.2 (10% methanol/chloroform and one drop of ammonium hydroxide)

HPLC: 99.0% (area)

$^1$H NMR: conforms (300 MHz, DMSO)

TABLE 7

| 7-(2-Morpholin-4-yl-ethoxy)-2-(4-aminophenyl) imidazo [2,1-b]benzothiazole lot summary | | | | |
|---|---|---|---|---|
| 7-(2-Morpholin-4-yl-ethoxy)-2-(4-nitrophenyl) imidazo [2,1-b]benzothiazole | Raney Ni | Yield | Yield % | HPLC (% A) |
| 0.580 Kg | ~55 g | 0.510 Kg | 95% | 99.0% |
| 0.446 Kg | ~50 g | 0.446 Kg | 96% | 99.2% |
| 0.550 Kg | ~55 g | 0.970 Kg | 95% | 99.0% |
| 0.550 Kg | ~55 g | | | |
| 0.550 Kg | ~55 g | 1.030 Kg | 95% | 98.8% |
| 0.550 Kg | ~55 g | | | |

Procedure E: Preparation of phenyl 5-(1-hydroxy-2-methylpropan-2-yl)isoxazol-3-ylcarbamate

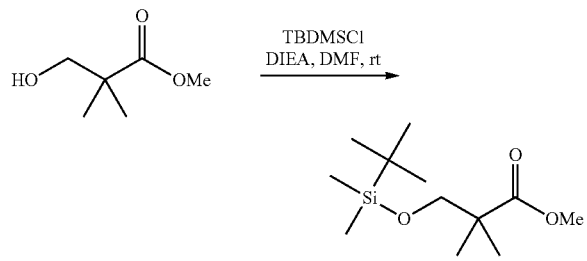

Step 1: A solution of methyl 3-hydroxy-2,2-dimethylpropanoate (5.00 g, 38 mmol), N,N-diisopropylethylamine (7.30 g, 57 mmol) and tert-butyldimethylchlorosilane (6.80 g, 45 mmol) in dry DMF (70 mL) was stirred at room temperature for 12 h. The reaction solution was quenched with water (225 mL) and extracted with diethyl ether (3×50 mL). The combined organic extracts were washed with water (100 mL), brine (100 mL), then dried over MgSO$_4$. Concentration under reduced pressure afforded methyl 3-(tert-butyldimethylsilyloxy)-2,2-dimethylpropanoate as colorless oil (9.36 g, 100%). It was used in the next step without further purification. $^1$H NMR (300 MHz, CDCl$_3$) δ 3.64 (s, 3H), 3.55 (s, 2H), 1.13 (s, 6H), 0.85 (s, 9H), 0.0 (s, 6H).

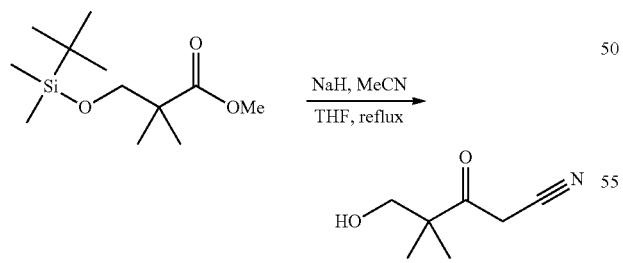

Step 2: To a refluxing suspension of sodium hydride (1.40 g of a 60% suspension in mineral oil, 35 mmol) in anhydrous toluene (45 mL), was added dropwise (over 1 h) a mixture of methyl 3-(tert-butyldimethylsilyloxy)-2,2-dimethylpropanoate (6.0 g, 24.39 mmol) from Step A and acetonitrile (1.80 mL, 35 mmol). After refluxing for a further 5 h, the mixture was cooled to rt and the pH was adjusted to 4 with aqueous HCl solution. The mixture was extracted with ethyl acetate (3×200 mL) and the combined organic layers washed with brine (2×200 mL), separated, dried over Na$_2$SO$_4$, and filtered. Concentration under reduced pressure, followed by Purification via silica gel chromatography eluting with 33% ethyl acetate in petroleum ether, afforded 5-hydroxy-4,4-dimethyl-3-oxopentanenitrile as a yellow oil (1 g, 29%). $^1$H NMR (300 MHz, CDCl$_3$) δ 3.76 (s, 2H), 3.61 (s, 2H), 1.19 (s, 6H).

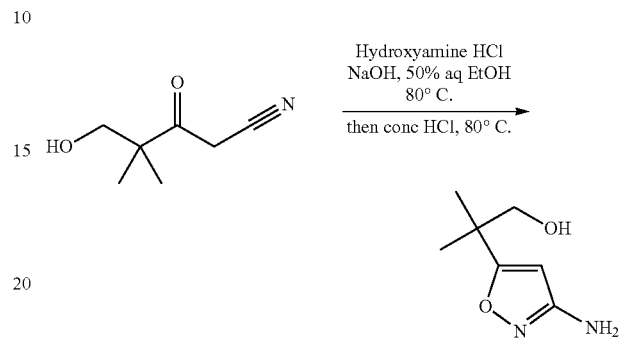

Step 3: A mixture of 5-hydroxy-4,4-dimethyl-3-oxopentanenitrile from Step B (1 g, 7.09 mmol), sodium hydroxide (378 mg, 9.45 mmol), and hydroxylamine hydrochloride (656 mg, 9.43 mmol) in a mixture of ethanol (100 mL) and water (100 mL), was heated at 60° C. for 22 h. After cooling to rt, concentrated HCl (1 g) was added and stirred at 50° C. for 2 h followed by 80° C. for a further 1 h. After concentration under reduced pressure, the mixture was treated with 30% sodium hydroxide solution and extracted with chloroform (3×100 mL). The combined organic layers were washed with water (100 mL), brine (100 mL), dried over Na$_2$SO$_4$, and filtered. Concentrated under reduced pressure, followed by purification via recrystallisation from diethyl ether, afforded 2-(3-aminoisoxazol-5-yl)-2-methylpropan-1-ol as a colorless solid (600 mg, 54%). $^1$H NMR (300 MHz, CDCl$_3$) δ 5.64 (s, 1H), 3.65 (s, 2H), 2.30 (brs, 2H), 1.31 (s, 6H); LC-MS (ESI) m/z 156 (M+H)$^+$.

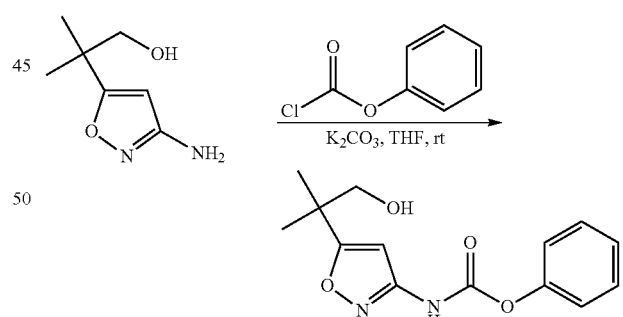

Step 4: To a stirred mixture of 2-(3-aminoisoxazol-5-yl)-2-methylpropan-1-ol from Step C (100 mg, 0.64 mmol) and potassium carbonate (166 mg, 1.20 mmol) in anhydrous tetrahydrofuran (15 mL) at rt, was added dropwise a solution of phenyl chloroformate (100 mg, 0.64 mmol) in tetrahydrofuran (6 mL). After stirring at rt for 15 h, the mixture was filtered and concentrated under reduced pressure. The residue was dissolved in dichloromethane (50 mL) and washed with water (50 mL), brine (50 mL), separated, and dried over MgSO$_4$. The mixture was filtered and concentrated under reduced pressure. Crystallization from a mixture of ether and hexane afforded afforded phenyl 5-(1-hydroxy-2-methylpropan-2-yl)isoxazol-3-ylcarbamate as a colorless solid (120 mg, 68%). $^1$H NMR (300 MHz, CDCl$_3$) δ 8.30 (brs, 1H), 7.42-7.43 (m, 2H), 7.26 (m, 1H), 7.16-7.21 (m, 2H), 6.65 (s, 1H), 3.67 (s, 2H), 1.98 (brs, 1H), 1.33 (s, 6H).

Procedure F: Preparation of Compound I-1

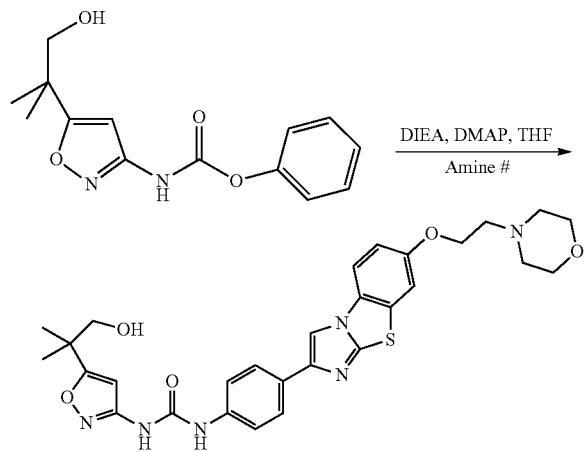

In a round bottomed flask 7-(2-Morpholin-4-yl-ethoxy)-2-(4-aminophenyl)imidazo [2,1-b]benzothiazole (1.07 g, 2.7 mmoles), phenyl 5-(1-hydroxy-2-methylpropan-2-yl)isoxazol-3-ylcarbamate (0.750 g, 2.7 mmoles), diisopropylethyl amine (0.700 ml, 0.517 g, 4.0 mmoles) and DMAP (50 mg, 0.4 mmoles) were dissolved in 20 mL of dry THF and heated to 50 C overnight. The reaction was concentrated to dryness and chromatographed over silica gel eluting with a methanol/dichloromethane gradient 0-15% over 18 column volumes. The main peak was collected and concentrated to a tan solid weighing 1.25 g, 80% yield.

$^1$H NMR (DMSO-d6) 9.51 (s, 1H); 8.86 (s, 1H); 8.60 (s, 1H); 7.87-7.76 (m, 4H); 7.66 (s, 1H); 7.50 (d, 2H); 7.16 (m, 1H); 6.54 (s, 1H); 4.95 (s, 1H); 4.15 (m, 2H); 3.58 (m, 5H); 3.45 (m, 3H); 3.16 (m, 1H); 2.73 (m, 2H); 1.23 (s, 6H)

LCMS M+H 577

Alternatively, the reaction may be carried out on a large scale by setting a reactor to 20° C. and charging with one equivalent of 7-(2-morpholin-4-ylethoxy)-2-(4-aminophenyl)imidazo[2,1-b]benzothiazole, 1.1 equivalent of 3-amino-5-t-butylisoxazole phenyl carbamate, 0.06 equivalent of DMAP and 260 kg of DCM. Following agitation of the mixture, 0.15 equivalent of TEA is added, followed by additional DCM (5 kg). The reaction is allowed to heat at reflux (about 40° C.) with agitation for at least 20 hours. Complete dissolution may be observed followed by product crystallizing from solution after about 30 minutes.

Example 5

Cyp Enzyme Inhibition Assay for Compound I-1

The ability of the compound I-1 to inhibit human metabolizing enzymes CYP3A4, CYP2C9, CYP2D4, CYP2C19 and CYP1A2, was assessed using those enzymes found collectively in human liver microsomes. The test compound I-1 was prepared as a solution in DMSO or acetonitrile and plated in duplicate rows of a 96-well plate (Nunc) for a final assay concentration of 40 μM in 0.2% DMSO (or 2% acetonitrile) in the first column and serially diluted two-fold going down the row. A known selective inhibitor of a given CYP enzyme listed in Table 8 was selected as the appropriate positive control. For each CYP enzyme inhibition assay, an appropriate enzyme-substrate mixture was prepared to afford a final assay concentration of 75 mM KPO$_4$/pH 7.4, 6.5 mM MgCl$_2$, 0.25 mg/mL pooled male and female human liver microsome (CellzDirect lot HMMC-PL020) with the amounts of the appropriate substrate for each CYP enzyme assay given in Table 8. The enzyme-substrate mixture was added to columns 1 through 10 and column 11 served as a negative control with enzyme solution lacking substrate. A solution of NADPH (Calbiochem) was then added to all rows except for one where NADPH would be added after the incubation period, in order to detect NADPH-independent non-CYP-mediated metabolism. The plate was briefly vortexed and left to shake in a 37° C. water bath for 20 minutes. The enzymatic activity was terminated using a stopping solution containing 3:1 acetonitrile/H$_2$0+0.05% formic acid and the appropriate internal standard given for each CYP inhibition assay in Table 8. Then NADPH was added to the first column and the plate was vortexed and then centrifuged at 3600 rpm for 10 minutes. The wells were further diluted with 1:1 with acetonitrile/water with 0.05% formic acid prior to detection by LC-MS of the formation of the corresponding CYP metabolites listed in Table 8. The IC$_{50}$ value was obtained from the curve generated by the Hill equation with a coefficient fixed at 1. The IC$_{50}$ values of compound I-1 for each CYP enzyme is given in Table 8 and represents the amount of compound I-1 necessary to inhibit a given CYP enzyme activity by 50%.

TABLE 8

| CYP enzyme | CYP3A4 | CYP2C9 | CYP2D4 | CYP2C19 | CYP1A2 |
|---|---|---|---|---|---|
| Positive control (final assay concentration) | ketoconazole (0.5 mM, Sigma) | sulfaphenazole (2 mM, Sigma) | quinidine (1.0 mM, Sigma) | triclopidine (1.0 mM, Sigma) | furafylline (0.6 mM, BD Biosciences) |
| Substrate (final assay concentration) | testosterone (75 mM, Sigma) | Diclofenac (16 μM, Sigma) | dextromethorphan (8 μM, Sigma) | mephenytoin (51 μM, Toronto Research Chemicals, Inc.) | phenacetin (78 μM, Sigma) |
| Metabolite detected by LC/MS | 6b-hydroxy testosterone | 4-hydroxy diclofenac | dextrorphan | 4-hydroxy mephenytoin | acetominophen |
| Internal Standard in stopping solution | Cortisone (0.6 μg/mL, Sigma) | flufenamic acid (0.6 μg/mL, Sigma) | propranolol HCl (0.6 μg/mL, Sigma) | Phenytoin (0.3 μg/mL, Sigma) | 4-hydroxy butyranilide (0.6 μg/mL, Sigma) |
| Compound I-1 IC$_{50}$ | >40 μM | >40 μM | >40 μM | 15.5 μM | >40 μM |

Example 6

MV4-11 Cellular Proliferation Assay

Cancer cell viability and proliferation was measured using a fluorimetric assay that measures reduction of a resazurin-containing dye CTB, (Cell Titer Blue®, Promega #G8081), into the highly fluorescent resorufin by various redox enzymes, where metabolic activity is taken as a measure of cell viability.

MV4;11 is a well-characterized Flt3-dependent human cell line that contains the internal tandem duplication mutation (ITD mutation) found in a certain subset of patients with acute myeloid leukemia and which expresses constitutively active Flt3 receptors (Yee et al. *Blood* 2002 100(8), 2941-2949). This cell line was used to determine the ability of Compound I-1 to inhibit Flt3 receptors having the ITD mutation. RS4;11 is a cell line expressing wild type FLT3 established from the bone marrow of an acute leukemia patient having the t(4;11) chromosomal abnormality. This cell line was used to determine the ability of Compound I-1 to inhibit wild type FLT3.

MV4;11 and RS4;11 cells were obtained from ATCC (Manassas, Va.) and cultured in Iscove's media with 10% FBS and RPMI complete with 10% FBS, respectively. Cells were cultured overnight in low serum media with 0.5% FBS. The following day, cells were seeded on to a 96-well plate at 40,000 cells per well at a volume of 100 µL per well. The compound plate containing Compound I-1 or positive control (Compound IA) was set up to achieve a final working concentration of 185 nM down to 0.03 nM by serially diluting three-fold with DMSO. DMSO was used as a negative control. 100 µL of compound was added to 100 µL of cells and incubated at 37° C. in 5% $CO_2$ for 72 hrs for MV4;11 cells and 48 hours for RS4;11 cells.

CTB reagent was thawed in a 37° C. water bath. 40 µL of CTB reagent was added to the plate containing the cells, and the cells were incubated with the reagent at 37° C. in 5% $CO_2$ for 3 hours. The absorbance was measured at 560 nm (excitation)/590 nm (emission) using Spectramax Plus 384 Absorbance Microplate Reader by Molecular Devices.

Cellular proliferation values were measured in terms of concentration of Compound I-1 that achieves 50% inhibition of MV4;11 cellular proliferation compared to control ($EC_{50}$) and was found to be 0.3 nM. The positive control, Compound IA, was found to have an $EC_{50}$ of 0.6 nM in MV4;11. Compound I-1 was also found to be more potent than Compound IA in RS4;11 cells, having an $EC_{50}$ of 2 nM, while the positive control, Compound IA, was found to have an $EC_{50}$ of 4 nM.

Example 7

Pharmacokinetic Studies with Compound I-1

Study Design

Rats were dosed either intravenously at 1 mg/kg dose or orally at 10 mg/kg dose with Compound I-1. Blood samples were collected over a 24 hour time-course. The plasma was analyzed for Compound I-1 and the pharmacokinetic parameters were determined.

Study Procedures And Methods

Pre-catheterized (jugular vein), male Sprague-Dawley rats (230-300 g) obtained from Charles River, Hollister, Calif., were acclimated at the vivarium of Rabbit and Rodent Diagnostic Associates (San Diego, Calif.) for at least three days following delivery and prior to entering a study. Rats were fasted overnight before intravenous or oral dosing. For intravenous dosing, Compound I-1 was dissolved in a 3:1 PEG400:$H_2O$ (Water For Injection) solution and administered at a dose of 1 mg/kg. For oral dosing, Compound I-1 was dissolved in a 22% hydroxypropyl-β-cyclodextrin (HPBCD) solution and administered at a dose of 10 mg/kg. Blood was collected at 5 (IV only), 15, 30 min, 1, 2, 4, 6, and 24 hr postdose using $K_3$EDTA as anticoagulant and plasma was harvested for the analysis of Compound I-1.

Plasma samples, calibration standards and quality control samples (20 µL) were extracted with six volumes of acetonitrile containing an internal standard (25 ng/mL) and analyzed using LC-MS/MS analysis (API 3200). Sample separation was achieved on a Zorbax SB C8 column (5 µm, 4.6×50 mm) at a flow rate of 1.6 mL/min. The gradient program was from 5-95% acetonitrile in 0.05% formic acid over one minute. The mass transition from m/z 577.18 to 421.10 was monitored for Compound I-1. The internal standard mass transitions monitored were 483.0 to 317.2.

Data Analysis and Results

Pharmacokinetic parameters of Compound I-1 were calculated based on the plasma concentration-time profiles of each animal using the noncompartmental models in WinNonlin v5.2 (Pharsight, Mountain View, Calif.).

Following a single 1 mg/kg IV dose in rats, Compound I-1 demonstrated a clearance of 8.83 mL/min/kg, apparent volume of distribution of 1.34 L/kg, and apparent half-life of 3.4 hours. Following a single 10 mg/kg oral dose, Compound I-1 reached a $C_{max}$ of 0.36 µM at 1.2 hours ($T_{max}$) and absolute bioavailability was 6.9% (FIG. 1).

TABLE 9

Summary of Compound I-1 Oral and Intravenous Pharmacokinetic Parameters in Rats

| Oral (mg/kg) | $C_{max}$ (µM) | $T_{max}$ (hr) | $AUC_{0-\infty}$ (µM · hr) | $T_{1/2}$ (hr) | F (%) | Vehicle |
|---|---|---|---|---|---|---|
| 10 | 0.36 | 1.2 | 2.27 | 3.7 | 6.9 | 3:1 PEG400:H20 |

| Intravenous (mg/kg) | CL (mL/min/kg) | $V_d$ (L/kg) | $AUC_{0-\infty}$ (µM · hr) | $T_{1/2}$ (hr) | | Vehicle |
|---|---|---|---|---|---|---|
| 1 | 8.83 | 1.34 | 3.29 | 3.4 | | 22% HPBCD |

*F % calculated with the dose normalized $AUC_{0-inf}$ IV data.
n = 3 PO and n = 2 IV

Example 8

Plasma Protein Binding Assay for Compound I-1

Reagents: 1× Isotonic PBS (Mediatech, Inc., Herndon, Va.); 96 Well Equilibrium Dialyzer (Harvard Apparatus, Holliston, Mass.) and Animal plasma from species of interest.

Assay Conditions:

1 µM solutions of test compound were prepared in both isotonic PBS and 10% animal plasma in isotonic PBS.

200 µl of each test solution was added to opposite sides of the equilibrium dialysis membrane.

Samples were incubated for 16-20 hours at 37° C.

After incubation, 100 µl sample was removed from the PBS side and diluted with 100 µl of 20% animal plasma in PBS.

100 µl sample was removed from the 10% animal plasma side and diluted with 100 µl of 10% animal plasma.

A calibration curve was prepared in 10% animal plasma to extrapolate unknown concentrations.

Samples were analyzed by LC/MS/MS.

Sample Analysis

50 µl of samples, calibration standards and quality control standards were extracted with 100 µl of acetonitrile containing 25 ng/ml of internal standard.

All samples were filtered to remove precipitate.

10 µl sample was injected onto a 4.6×50 mm, 5 µm, Zorbax C8 HPLC column under the following conditions:

Mobile Phase A=0.05% Formic acid in water

Mobile Phase B=0.05% Formic acid in acetonitrile

Eluted with a gradient of 5%-90% B from 0.2 to 0.8 minutes at 1.6 ml/min.

Product ions were monitored at relevant mass transitions as determined by infusion. Unknown concentration was determined by comparing against calibration standards, after accounting for sample dilution.

Calculations

Calculate fraction unbound in 10% plasma $Fu(10\%)$
=1−(PC−PF)/PC

Convert 10% plasma value to 100% $Fu(100\%)$
=$Fu10\%/(10-9*Fu10\%)$.

Percentage of unbound Compound I-1 in 10% plasma was 42.5%. Percentage of unbound Compound IA, hydrochloride salt in 10% plasma was 17%.

Example 9

Binding Constant ($K_d$) Measurements for Small-Molecule-Kinase Interactions

Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17× PBS, 0.05% Tween 20, 6 mM DTT). Test compounds were prepared as 100× stocks in DMSO and rapidly diluted into the aqueous environment. DMSO was added to control assays lacking a test compound. Primary screen interactions were performed in polypropylene 384-well plates in a final volume of 34 µL, while Kd determinations were performed in polystyrene 96-well plates in a final volume of 135 µL. The assay plates were incubated at room temperature with shaking for 1 hour, long enough for binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 2 µM non-biotinylated affinity ligand) and incubated at room temperature with shaking for 30 min. The kinase concentration in the eluates was measured by quantitative PCR. Each kinase was tested individually against each compound. Kds were determined using eleven serial three-fold dilutions.

TABLE 10

| Kinase | Compound I-1 Kd (nM) | Compound IA Kd (nM) |
|---|---|---|
| FLT3 | 0.68 | 1.6 |
| FLT3 (D835H) | 1.9 | 3.7 |
| FLT3 (D835Y) | 5.5 | 7.1 |
| FLT3 (ITD) | 8.8 | 5.7 |
| FLT3 (K663Q) | 0.69 | 2.2 |
| FLT3 (N841I) | 0.77 | 4.1 |

Example 10

Time Dependant Inhibition of CYP 3A4, 2C8, and 2C19 by Compound I-1

The purpose of this study was to determine if Compound I-1 is a time dependent inhibitor of the CYP isoforms 3A4, 2C19 and 2C8.

For each CYP isoform tested, 10 µM Compound I-1 was pre-incubated with pooled male and female human liver microsomes with NADPH in a 37° C. shaking water bath in duplicate to afford a final pre-incubation assay concentration of 100 mM KPO4/pH 7.4, 10 mM MgCl2, 2 mg/mL of human liver microsome (CellzDirect lot HLM HMMC-PL020) and 1 mM NADPH (Calbiochem). At each pre-incubation time point (0, 5, 10, 20, and 30 minutes) 20 µL was removed and placed in a second 96 well plate on ice. After all pre-incubation time points were collected 180 uL of additional human microsome liver preparation containing the appropriate CYP specific substrate at its Km concentration listed in Table 11 plus NADPH, was added to each time point. The samples were incubated for an additional 10 minutes in a 37° C. shaking water bath and then quenched with 75:25 acetonitrile (ACN):water containing the appropriate internal standards listed in Table 11. After brief mixing, the plate was centrifuged and the supernatant removed for analysis by LC/MS/MS (API 4000 Qtrap) for the formation of 6-hydroxy-testosterone (CYP3A4), 4-hydroxy-mephenyloin (CYP2C19), or 6-hydroxy-taxol (CYP2C8). As determined by analysis on the effect of metabolite formation of CYP specific substrates after various pre-incubation times of Compound I-1 in human liver microsomes, Compound I-1 was not a time dependant inhibitor of CYP3A4, 2C19, or 2C8. Consistent with Example 5, Compound I-1 did inhibit CYP2C8-mediated metabolite formation at 10 µM, but not in a time dependent manner.

TABLE 11

| CYP enzyme | CYP3A4 | CYP2C8 | CYP2C19 |
|---|---|---|---|
| Positive control (final assay concentration) | ketoconazole (10 µM, Sigma) | Quercertin (90 µM, Tocris) | triclopidine (10 µM, Sigma) |
| Substrate (final assay concentration) | testosterone (75 µM, Sigma) | taxol (14 µM, Tocris) | mephenytoin (50 µM, Toronto Research Chemicals, Inc.) |
| Metabolite detected by LC/MS | 6b-hydroxy testosterone | 6a-hydroxy taxol | 4-hydroxy mephenytoin |
| Internal Standard in stopping solution | Cortisone (0.3 µg/mL, Sigma)/ Propranolol (0.3 µg/mL, Aldrich) | Cortisone (0.3 µg/mL, Sigma)/ Propranolol (0.3 µg/mL, Aldrich) | Cortisone (0.3 µg/mL, Sigma)/ Propranolol (0.3 µg/mL, Aldrich) |

Example 11

Inhibitory constant $K_I$, for the Human CYP Isoforms 3A4, 2C19 and 2C8

This study was designed to determine the inhibitory constant, $K_I$, for the human CYP isoforms 3A4, 2C19 and 2C8 and to characterize the type of inhibition (competitive, non-competitive, or uncompetitive).

A 2 mM stock of Compound I-1 was prepared in acetonitrile (ACN) and serially diluted 2-fold from 2000 µM to 15.63 µM in ACN. Several human liver microsome (CellzDirect lot HLM HMMC-PL020) preparations containing substrate (testosterone for CYP3A4, mephenyloin for CYP2C19 or taxol for CYP2C8) were prepared with substrate concentrations ranging from 5-fold Km to 0.039-fold Km (serial 2-fold dilutions). Individual human liver microsome preparations containing the substrate were then incubated with Compound I-1 (final concentration range 40 µM to 0.31 µM of Compound I-1) for a final incubation concentration of 0.5 mg/mL microsome, 75 mM $KPO_4$, 6.5 mM $MgCl_2$, 1 mM NADPH and 2% acetonitrile (ACN). The samples were incubated in a 37° C. shaking water bath for 20 minutes then quenched with ACN:water (75:25) containing internal standards propranolol at 0.3 ng/mL and cortisone at 0.3 ng/mL. After brief mixing, the plate was centrifuged and the supernate removed for analysis by LC/MS/MS (API 4000 Qtrap) for formation of 6-hydroxy-testosterone (CYP3A4), 4-hydroxy-mephenyloin (CYP2C19) or hydroxy-taxol (CYP2C8). The data was analyzed using global non-linear regression software (GraphPad Prism) and the overall fit of the data ($R^2$) was used to determine if Compound I-1 was a competitive, non-competitive, or uncompetitive inhibitor. In addition the data was plotted as a Lineweaver-Burke graph (1/V versus 1/S, where V is the maximum enzyme velocity and S is the substrate concentration) for each inhibitor concentration. Based on the location of convergence (competitive and non-competitive) or non convergence (uncompetitive) of the plots at each inhibitor concentration, the type of inhibition was determined.

Global non-linear regression allows analysis of all the individual inhibitor curves simultaneously and determines the best fit value for shared parameters between the data sets, in this case $K_I$ (or $K_I'$). The results of the global nonlinear analysis of Compound I-1 inhibition of the CYP450 isoforms 3A4, 2C19 and 2C8 are shown in Table 12.

TABLE 12

$K_I$ and $R^2$ values for Compound I-1 inhibition of CYP3A4, CYP2C19 and CYP2C8

|  | Competitive | Non-competitive | Uncompetitive |
|---|---|---|---|
| CYP2C19 | | | |
| Best Fit $K_I$ (µM) | 1.7 | 10.4 | 7.4 ($K_I'$) |
| Global $R^2$ | 0.9650 | 0.9919 | 0.9783 |
| CYP2C8 | | | |
| Best Fit $K_I$ (µM) | 22.1 | 60.8 | 37.7 ($K_I'$) |
| Global $R^2$ | 0.9832 | 0.9920 | 0.9917 |
| CYP3A4 | | | |
| Best Fit $K_I$ (µM) | 13.1 | 48.9 | 36 ($K_I'$) |
| Global $R^2$ | 0.9652 | 0.9788 | 0.9784 |

Figure 11:
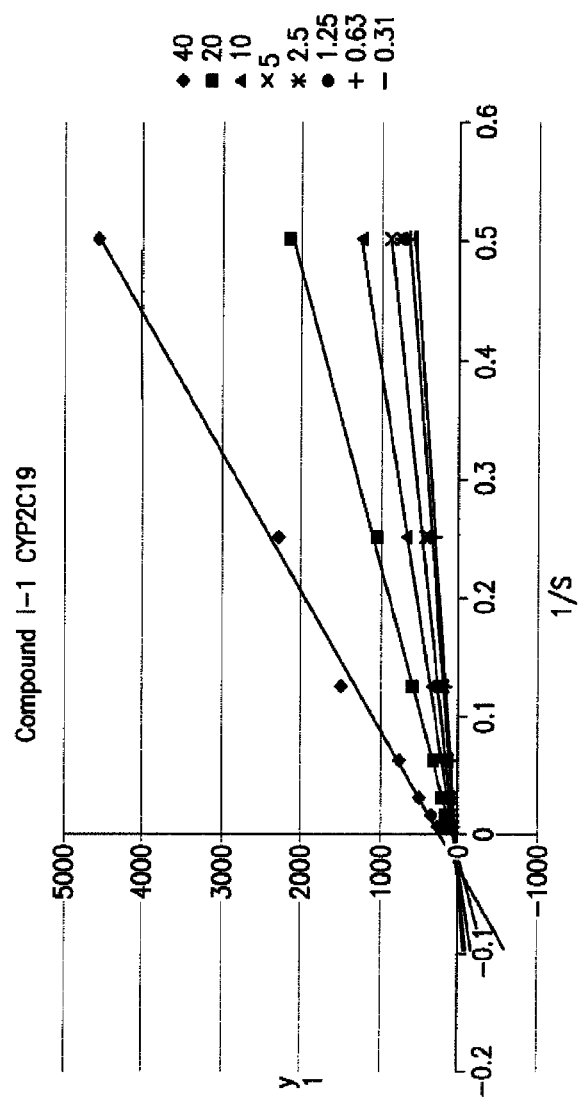
FIG. 11 provides Lineweaver-Burke plot for inhibition of CYPC19 by Compound I-1.
Figure 12:
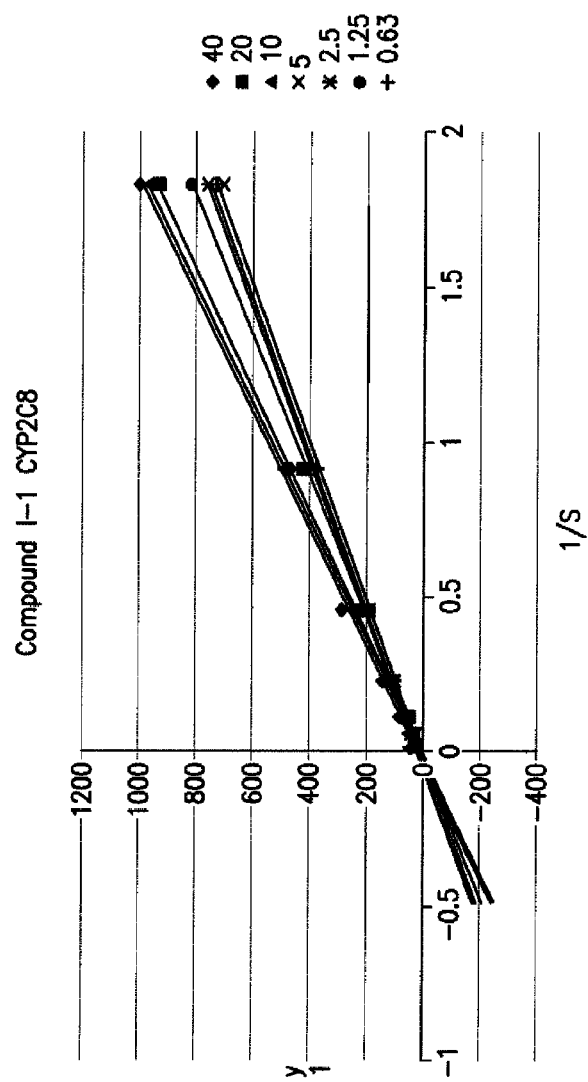
FIG. 12 provides Lineweaver-Burke plot for inhibition of CYP2C8 vy Compound I-1.
Figure 13:
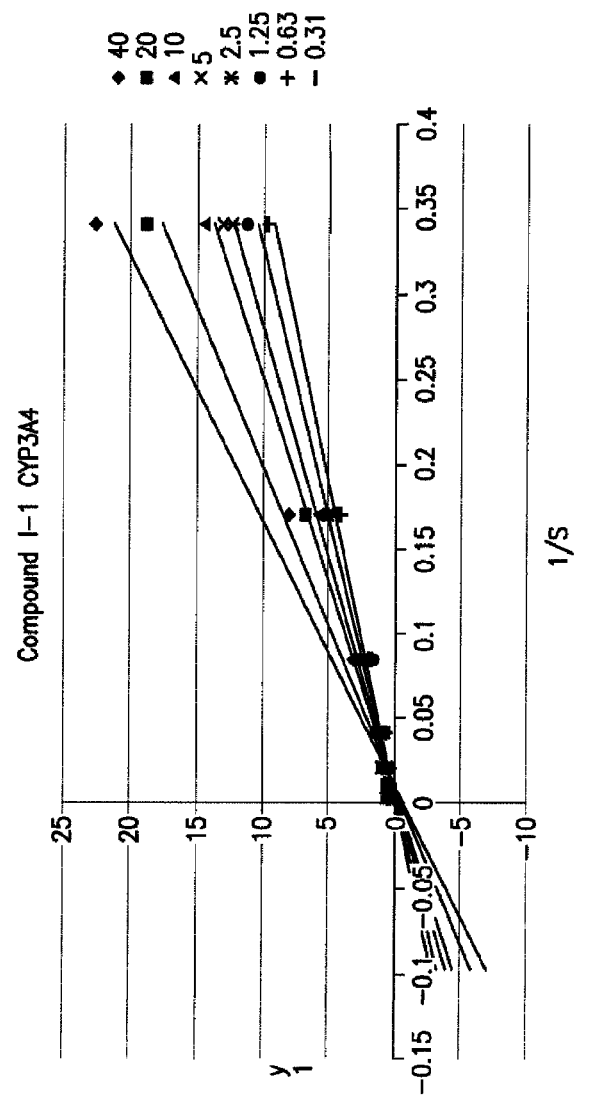
FIG. 13 provides Lineweaver-Burke plot for inhibition of CYP3A4 by Compound I-1.

As Table 12 indicates, the fit for competitive inhibition is poor for all three isoforms. Therefore, Compound I-1 does not appear to be a competitive inhibitor of any of the CYP isoforms tested. The best fit for CYP2C19 is non-competitive inhibition, with a $K_I$ value of 10.4 µM. This is also supported by the Lineweaver-Burke plot for Compound I-1 inhibition of CYPC19 (FIG. 11) which clearly indicates the concentration of inhibitor slopes converge on the X-axis, which is indicative of a non-competitive inhibitor. For CYP2C8 and CYP3A4 the best fit data suggests Compound I-1 could be either a non-competitive or uncompetitive inhibitor. However, in both cases, when the individual curve fits for each concentration of inhibitor are examined the data sets for non-competitive inhibition have better individual fits ($R^2$ values greater than 0.9500) than the data sets for uncompetitive inhibition. Examination of the Lineweaver-Burke plot for CYP2C8 (FIG. 12) and CYP3A4 (FIG. 13) show convergence at the X-axis, instead of nonconvergent parallel lines (as would be expected for an uncompetitive inhibitor) supporting that Compound I-1 is a non-competitive inhibitor of both isoforms.

As determined by global nonlinear regression analysis on the effect of metabolite formation at various concentrations of Compound I-1 and CYP specific substrates; Compound I-1 is a weak non-competitive inhibitor of CYP2C19 (KI=10.4 µM), but is effectively not an inhibitor of CYP3A4 (KI=48.9 µM), and CYP2C8 (KI=60.8 µM).

Example 12 hERG Channel Inhibition

The purpose of this assay is to determine the inhibition of hERG cardiac potassium ion channels, which is the most common mechanism underlying adverse cardiac events. This current is important for cardiac myocyte repolarization and is a common target for drugs that prolong the QT interval. Test articles in this study were therefore characterized to determine their ability to inhibit the hERG channel. Ion channel activity was measured using a stably transfected Chinese Hamster Ovary (CHO) cell line expressing the hERG mRNA.

A CHO cell line stably expressing hERG channels was obtained from Aviva Systems Biology LLC and used for the study. Cells were cultured in DMEM/F12 containing 10% FBS, 1% penicillin/streptomycin and 500 µg/ml G418. Before testing, cells were harvested using Accumax (Innovative Cell Technologies).

For electrophysiological recordings, the following solutions were used:

External Solution: 2 mM $CaCl_2$; 2 mM $MgCl_2$; 4 mM KCl; 150 mM NaCl; 10 mM Glucose; 10 mM HEPES; 310-320 mOsm; pH 7.4 (adjusted with 1M NaOH.)

Internal Solution: 140 mM KCl; 10 mM $MgCl_2$; 6 mM EGTA; 5 mM HEPES-Na; 5 mM ATP-Mg; 300-320 mOsm; pH 7.25 (adjusted with 1M KOH).

Whole cell recordings were performed using PX 7000A (Axon Instruments) with AVIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally a step back to −50 mV for 5 s removed activation and the deactivating tail current was recorded.

All compounds were prepared from either 10 or 30 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use. Equal amounts of DMSO (0.1%) were present in all final dilutions.

After achieving whole cell configuration, cells were monitored for 90 s to assess stability and then washed with External Solution for 66 s. The voltage protocol described above was then applied to the cells every 12 s throughout the procedure.

External solution containing 0.1% DMSO (vehicle) was applied to the cells to establish a baseline. After allowing the current to stabilize for 3 to 5 min, test articles were applied. Test article solutions were added to cells in 4 separate additions. Cells were kept in test solution until effect of the test article reached steady state, to a maximum of 12 min. Next, 1 μM cisapride (positive control) was added. Finally, washout with External Solution was performed until the recovery current reached a steady state.

Data analysis was performed using DataXpress (Axon Instruments), Clampfit (Axon Instruments) and Origin (Originlab Corporation) software and shown in Table 13:

TABLE 13

| Compound | Concentration | % Block Trial 1 | % Block Trial 2 |
| --- | --- | --- | --- |
| Compound I-1 | 10 μM | <10 | <10 |
| Cisapride | 1 μM | >95 | >95 |

Example 13

MDR1-MDCK Cell Permeability Using Compound I-1 as a P-Glycoprotein Inhibitor or Substrate This study was conducted to obtain aqueous and surfactant solubility of compound I-1 and to characterize the efflux substrate and inhibitor potential of Compound I-1 in the MDR1-MDCK cell model system. For inhibitor studies, the effect of Compound I-1 on bidirectional transport of Digoxin was evaluated.

Compound I-1 was dissolved in DMSO to give a concentration of 10 mM.

Assay reference compounds were obtained from Aldrich or Sigma. AcPhe(NMePhe)$_2$NH$_2$ was synthesized by ADMETRx. MDR1-MDCK cells were obtained from the Netherlands Cancer Institute (NKI). HPLC solvents and water were obtained from VWR and were of chromatography grade.

The identity of Compound I-1 was confirmed by comparing the observed mass spectral molecular ion with that expected from the molecular weight. Compound I-1 was run on a Waters X-Bridge C-18 (186003021) 50×2.1 mm column with 3.5 micron particle packing at a flow rate of 1 mL/min and with the temperature maintained at 50° C.

Solvent A was water with 0.1% formic acid. Solvent B was acetonitrile with 0.07% formic acid.

The gradient timetable was as follows:

| Time | % A | % B |
| --- | --- | --- |
| 0.00 | 95 | 5 |
| 1.50 | 5 | 95 via linear ramp |
| 2.20 | 5 | 95 |
| 2.30 | 95 | 5 |

The HPLC instrument was a Waters Alliance 2795. The mass spectrometer was a Waters Quattro micro or a Waters Quattro Premier and the MS/MS transition monitored was:

| Compound | Transition | Dwell | Cone Voltage | Collision Energy | Retention Time |
| --- | --- | --- | --- | --- | --- |
| Compound I-1 | 577.23 > 421.10 | .050 | 54 | 28 | 0.88 ES+ |

Determination of Aqueous and Surfactant Solubility:

Aliquots of the DMSO stocks were transferred to either pH 7.4, Hank's balanced salt solution containing 25 mM HEPES (HBSS) or HBSS containing 0.05% Polysorbate 80 to give target concentrations of 250 μM in solute and 2.5% DMSO. After equilibration at room temperature overnight the solutions were filtered and solute concentration determined by fast gradient HPLC without further dilution of the samples. UV/VIS/MS detection was used with reference to 1, 5, 10, 50, 100 and 250 μM analytical standards. These analytical standards were prepared from a 500 μM intermediate stock solution made by diluting 10 μl of the 10 mM sample stocks into 190 μl of 50:50 (v/v) acetonitrile/water. Aliquots of this solution were transferred in duplicate into a 96 well plate in the amounts of 0.4, 2, 4, 20, 40, and 100 μl with the volumes made up to 200 total μl with acetonitrile/water and the plate was then heat sealed with a foil sheet. Prior to sample filtration, filters were primed with 600 μl of sample to resolve potential adsorption problems. Both sample replicates were collected through the primed filter. Duplicate determinations were made in all cases.

Determining Bidirectional MDR1-MDCK Permeability

MDR1-MDCK cells were grown to confluence for 5-10 days on 1 μm filters in 24-well plate. Aliquots of DMSO solute stocks were diluted into Hank's balanced salt solution (HBSS) pH 7.4 containing 25 mM HEPES+−0.05% PS80 to give 0.5, 1.5 or 5.0 μM solute concentrations. Final concentrations of DMSO in the assayed samples ranged from 0.005% for the 0.5 μM concentration to 0.05% for the 5 μM concentration. DMSO in this concentration range has previously been shown to have no effect on monolayer or transport properties. The solute containing donor solutions were transferred to either the apical or basolateral chamber of the permeability diffusion apparatus. Receiver solutions consisted of Hank's balanced salt solution (HBSS) pH 7.4 containing 25 mM HEPES+0.05% PS80. The entire receiver solution was removed at 20 minute intervals and manually replaced with fresh buffer. The concentration of transported solute during each sampling interval was determined by HPLC/UV/MS. The standard curve was produced from serial dilutions of the dosing solution. D0 was a 50 μl aliquot of dosing solution from the donor well diluted with 450 μl of HBSS. The standard curve was produced from serial dilutions of the dosing solution (1:10, 1:25, 1:50, 1:100, 1:500 and 1:1000). Permeability coefficients were calculated for each sampling interval using the following equation:

$$P_{app1} = \frac{V_D}{A} \left[ \frac{1}{M_{D(0)}} \cdot \frac{\Delta M_{R(t)}}{\Delta t} \right]_{i^{th} interval}$$

Where VD=volume of donor (0.4 ml for Ap_Bl flux and 1.0 ml for Bl_Ap flux), A=surface area of the filter on which the monolayer was grown (0.31 cm2), MD(0)=mass in the donor at the beginning of the ith sampling interval, MR (t)=mass in the receiver at time t, and _t is the experimental interval (20 minutes). The apparent permeability, Papp, is then calculated as the average:

$$P_{app} = \frac{P_{app1} + P_{app2} + \ldots P_n}{n}$$

The average and standard deviation from the intervals is reported. Mass balance in the system was ascertained by comparing the sum of total transported solute and remaining donor solute with the starting mass of solute and is expressed as a percentage of donor solute at time zero. Significant deviations from 100% (generally less than 70%) suggest solute adsorption to the apparatus or monolayer, or chemical or metabolic instability during the course of the experiment. At the termination of the experiment, the cell monolayers are stored in the cold until the data is analyzed. After analysis, if mass balance falls below 70% in a given experiment, those monolayers are retrieved and extracted with acetonitrile.

After separation of cellular debris, the extract is analyzed for recoverable solute of interest. Reference compounds Ranitidine (low permeability), Pindolol (high permeability) and AcPhe(NMePhe)$_2$NH$_2$ (P-glycoprotein standard) were also included. All determinations were performed in duplicate.

The results of the aqueous solubility and bidirectional MDR1-MDCK permeabilities experiments are shown in Tables 14, 15, 16 and 17.

TABLE 14

Summary of Average Aqueous Solubility (µM)

| Compound | pH 7.4 | | 0.05% Polysorbate 80 | |
|---|---|---|---|---|
| | Average | Range | Average | Range |
| Compound I-1 | <1 | NA | 2 | 0 |
| Reserpine | <1 | NA | 5 | 1 |
| Ketoconazole | 18 | 2 | 86 | 1 |
| Furosemide | 192 | 7 | 243 | 1 |

TABLE 15

Summary of Bidirectional MDR1-MDCK Permeabilities: Compound I-1 as a substrate

| Compound | Conc | Pe$_{AP \to BL}$[1] | Mass Bal | Pe$_{BL \to AP}$[1] | Mass Bal | Assymetry Index | Conditions |
|---|---|---|---|---|---|---|---|
| Compound I-1 | 5 µM | 5.10 | 84% | 6.31 | 54 | 1.2 | Surf. |
| Compound I-1 repeat | 5 µM | 2.81 | 60 | 4.67 | 50 | 1.7 | Surf. |
| Ranitidine | 10 µM | 1.63 | 96 | 3.02 | 96 | 1.9 | Std |
| Pindolol | 10 µM | 31.7 | 99 | 30.6 | 92 | 1.0 | Std |
| AcPhe(NMePh)$_2$NH$_2$ | 10 µM | 1.72 | 85 | 42.4 | 80 | 24.7 | Std |
| AcPhe(NMePh)$_2$NH$_2$ | 10 µM | 9.26 | 96 | 27.8 | 89 | 3.0 | Surf. |

TABLE 16

Summary of Digoxin Bidirectional MDR1-MDCK Permeabilities: Compound I-1 as an Inhibitor - Preliminary Experiment

| Compound | Pe$_{AP \to BL}$[1] | Mass Bal | Pe$_{BL \to AP}$[1] | Mass Bal | Assymetry Index | Conditions |
|---|---|---|---|---|---|---|
| Digoxin (1 µM) | 0.24 | 122% | 20.0 | 117% | 83.3 | Std |
| Digoxin (1 µM) | 2.91 | 96% | 6.03 | 94% | 2.1 | Surf. |
| Digoxin (1 µM), Compound I-1 (0.5 µM) | 2.31 | 98% | 5.05 | 91% | 2.4 | Surf. |
| Digoxin (1 µM), Compound I-1 (1.5 µM) | 2.43 | 98% | 5.40 | 94% | 2.2 | Surf. |
| Digoxin (1 µM), Compound I-1 (5.0 µM) | 2.29 | 93% | 4.97 | 99% | 2.2 | Surf. |

TABLE 17

Summary of Digoxin Bidirectional MDR1-MDCK Permeabilities: Compound I-1 as an Inhibitor

| Compound | Pe$_{AP \to BL}$[1] | Mass Bal | Pe$_{BL \to AP}$[1] | Mass Bal | Assymetry Index | Conditions |
|---|---|---|---|---|---|---|
| Digoxin (1 µM) | 8.76 | 116% | 29.3 | 98% | 3.3 | Std |
| Digoxin (1 µM) | 2.21 | 106% | 4.93 | 97% | 2.2 | Surf. |
| Digoxin (1 µM), | 2.42 | 104% | 4.42 | 98% | 1.8 | Surf. |

TABLE 17-continued

Summary of Digoxin Bidirectional MDR1-MDCK Permeabilities:
Compound I-1 as an Inhibitor

| Compound | Pe$_{AP \rightarrow BL}$[1] | Mass Bal | Pe$_{BL \rightarrow AP}$[1] | Mass Bal | Assymetry Index | Conditions |
|---|---|---|---|---|---|---|
| Compound I-1 (5.0 µM) Digoxin (1 µM), Cyclosporin (20 µM) | 6.00 | 103% | 4.51 | 90% | 0.8 | Surf. |

[1]$\times 10^{-6}$ cm/sec
Mass Bal = mass balance, Surf. = surfactant, Std = standard Example 14

Preparation of 1-[5-(2-hydroxy-1-hydroxymethyl-1-methyl-ethyl)-isoxazol-3-yl]-3-{4-[7-(2-morpholin-4-yl-ethoxy)-benzo[d]imidazo[2,1-b]thiazol-2-yl]-phenyl}-urea (I-1a)

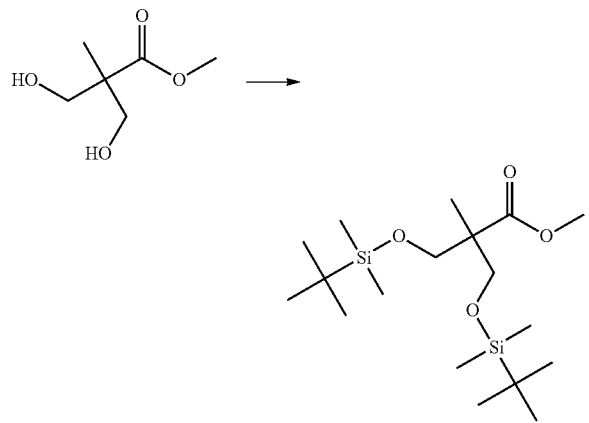

Step A: To a stirred solution of methyl 3-hydroxy-2-(hydroxymethyl)-2-methylpropanoate prepared as described in WO 2009/117080 A1 (1 equivalent) and N,N-diisopropylethylamine (2-5 equivalents) in anhydrous DMF at rt is added tert-butyldimethylchlorosilane (2-5 equivalents) and the mixture is stirred at rt until the reaction is substantially complete as monitored by LCMS or TLC. Water is added to the mixture, followed by extraction with diethyl ether. The organic layer is separated, dried over magnesium sulfate, filtered, and concentrated under reduced pressure. The residue is purified by silica gel flash chromatography to afford methyl 3-(tert-butyldimethylsilyloxy)-2-((tert-butyldimethylsilyloxy)methyl)-2-methylpropanoate.

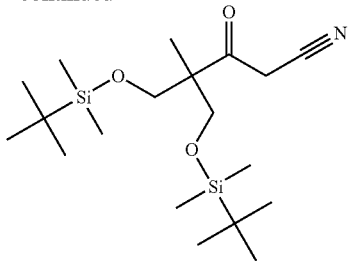

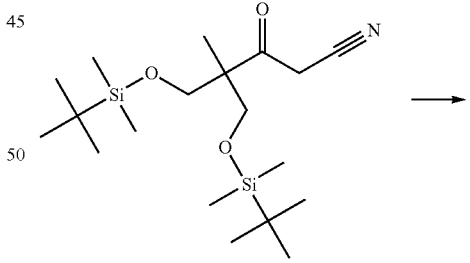

Step B: To a stirred refluxing suspension of 60% sodium hydride/mineral oil (1-2 equivalents) in anhydrous THF is added dropwise a mixture of methyl 3-(tert-butyldimethylsilyloxy)-2-((tert-butyldimethylsilyloxy)methyl)-2-methylpropanoate (1 equivalent) and anhydrous acetonitrile (1-2 equivalents). Stirring is continued at 70-80° C. for 5 to 22 h, and then the mixture is concentrated under reduced pressure. The residue is dissolved in water to yield a basic solution (pH>8), which is washed with ether, and the ether layer is discarded. The aqueous layer is acidified with aq hydrochloric acid to pH<2 and then extracted with diethyl ether. The combined extracts are dried over magnesium sulfate, filtered, and concentrated under reduced pressure to afford 5-(tert-butyldimethylsilyloxy)-4-((tert-butyldimethylsilyloxy)methyl)-4-methyl-3-oxopentanenitrile.

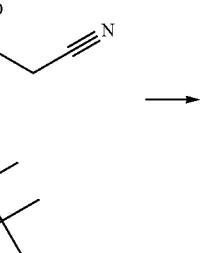

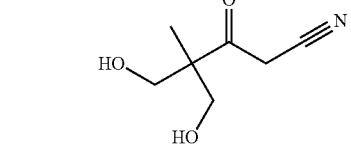

Step C: To a stirred solution of 5-(tert-butyldimethylsilyloxy)-4-((tert-butyldimethylsilyloxy)methyl)-4-methyl-3-oxopentanenitrile (1 equivalent) in anhydrous THF at 0° C. is added tetrabutylammonium fluoride (1-5 equivalents) and stirring is continued at rt until the reaction is substantially complete as determined by LCMS or TLC. Water is added followed by extraction with EtOAc. The extracts are dried over magnesium sulfate, filtered, and concentrated under reduced pressure. The residue is purified by silica gel flash chromatography to afford 5-hydroxy-4-(hydroxymethyl)-4-methyl-3-oxopentanenitrile.

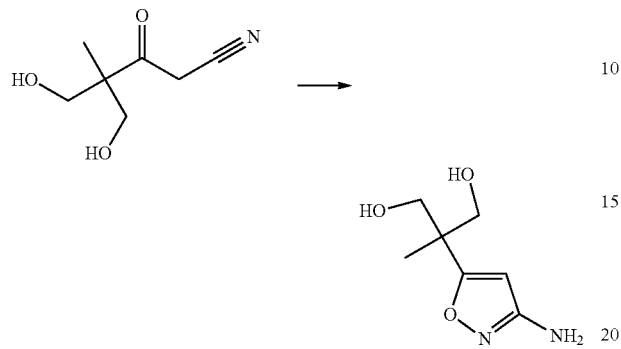

Step D: A mixture of 5-hydroxy-4-(hydroxymethyl)-4-methyl-3-oxopentanenitrile (1 equivalent) and sodium hydroxide (1.3 equivalents) in a mixture of water and EtOH is adjusted to pH 7.4-8 and then heated at 60-100° C. After 10 to 22 h, the mixture is acidified (pH≤1) with aq hydrochloric acid or aq sulfuric acid and heated for a further 2 to 5 h at 60-100° C. The reaction mixture is concentrated under reduced pressure and the residue is partitioned between 30% aq sodium hydroxide and chloroform. The organic layer is separated and the aqueous layer is further extracted with chloroform. The combined organic extracts are washed with water or brine, then dried over magnesium sulfate, filtered, and concentrated under reduced pressure. The residue is purified by silica gel flash chromatography to afford 2-(3-aminoisoxazol-5-yl)-2-methylpropane-1,3-diol.

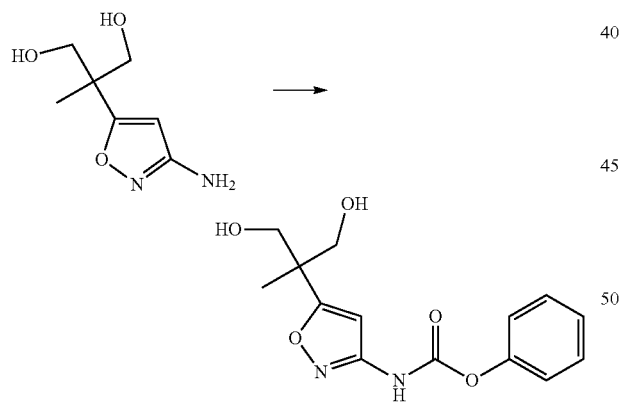

Step E: To a stirred mixture of 2-(3-aminoisoxazol-5-yl)-2-methylpropane-1,3-diol (1 equivalent) and potassium carbonate (2-5 equivalents) in anhydrous THF at rt is added dropwise phenyl chloroformate (1-2 equivalents) and stirring is continued at rt until the reaction is substantially complete as monitored by LCMS or TLC. The mixture is concentrated under reduced pressure and the residue is partitioned between water and dichloromethane. The organic layer is separated and the aqueous layer is further extracted with dichloromethane. The combined organic extracts are washed with water or brine, then dried over magnesium sulfate, filtered, and concentrated under reduced pressure. The residue is purified by silica gel flash chromatography to afford phenyl 5-(1,3-dihydroxy-2-methylpropan-2-yl)isoxazol-3-ylcarbamate.

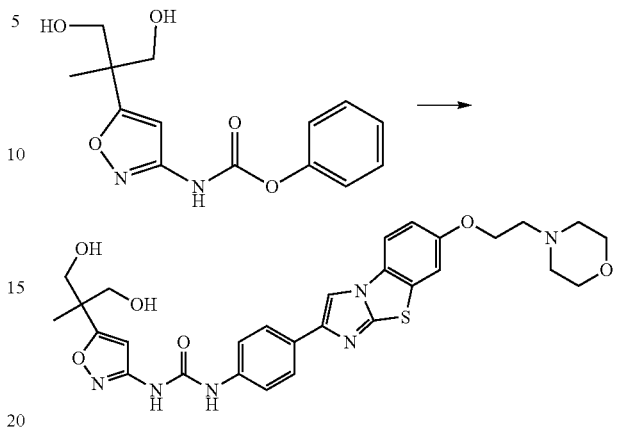

Step F: A mixture of phenyl 5-(1,3-dihydroxy-2-methylpropan-2-yl)isoxazol-3-ylcarbamate (1 equivalent), 7-(2-morpholin-4-yl-ethoxy)-2-(4-aminophenyl)imidazo[2,1-b]benzothiazole (4) (1 equivalent) and 4-(dimethylamino)pyridine (0.05-0.5 equivalents) in anhydrous THF is stirred at a temperature between rt and 50° C. until the reaction is substantially complete as monitored by LCMS or TLC. The mixture is concentrated under reduced pressure and the residue is purified by preparative reverse-phase HPLC or silica gel flash chromatography to afford 1-[5-(2-hydroxy-1-hydroxymethyl-1-methyl-ethyl)-isoxazol-3-yl]-3-{4-[7-(2-morpholin-4-yl-ethoxy)-benzo[d]imidazo[2,1-b]thiazol-2-yl]-phenyl}-urea (I-1a).

Alternatively, a mixture of phenyl 5-(1,3-dihydroxy-2-methylpropan-2-yl)isoxazol-3-ylcarbamate (1.1 equivalent), 7-(2-morpholin-4-yl-ethoxy)-2-(4-aminophenyl)imidazo[2,1-b]benzothiazole (4) (1 equivalent) and 4-(dimethylamino)pyridine (0.05-0.5 equivalents) in anhydrous DCM is stirred. To this reaction is added triethylamine (0.15 equivalent) and optionally, additional DCM and this mixture is then heated to reflux (~40° C.) until the reaction is substantially complete as monitored by LCMS, TLC or HPLC analysis.

Example 15

Preparation of 1-[5-(2-hydroxy-1,1-bis-hydroxymethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1b)

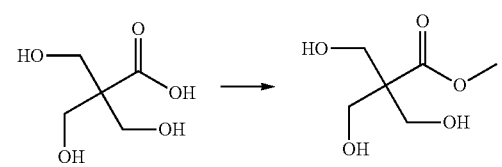

Step A: To a stirred solution of 3-hydroxy-2,2-bis(hydroxymethyl)propanoic acid, prepared according to EP 751223 A2, in MeOH at rt is added dropwise 2 M trimethylsilyl)diazomethane/diethyl ether (1-5 equivalents) and the mixture is stirred at rt until the reaction is substantially complete as monitored by LCMS or TLC. The mixture is concentrated under reduced pressure and the residue is partitioned between saturated aq sodium bicarbonate solution and dichloromethane. The organic layer is separated, dried over magnesium sulfate, filtered, and concentrated under reduced pressure. The residue is purified by silica gel flash chromatography to afford methyl 3-hydroxy-2,2-bis(hydroxymethyl)propanoate.

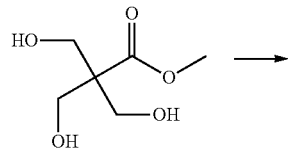

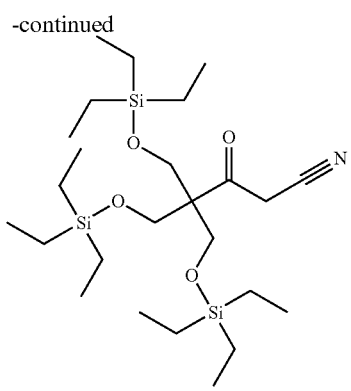

Step C: To a stirred refluxing suspension of 60% sodium hydride/mineral oil (1-2 equivalents) in anhydrous THF is added a mixture of methyl 3-(triethylsilyloxy)-2,2-bis((triethylsilyloxy)methyl)propanoate (1 equivalent) and anhydrous acetonitrile (1-2 equivalents) and stirring is continued at 70-80° C. for 5 to 22 h. The reaction mixture is concentrated under reduced pressure and the residue is dissolved in water to yield a basic solution (pH>8). The solution is washed with diethyl ether and the ether layer is discarded. The aqueous layer is acidified to pH<2 with aq hydrochloric acid and extracted with diethyl ether. The combined organic extracts are dried over magnesium sulfate, filtered, and concentrated under reduced pressure to afford 3-oxo-5-(triethylsilyloxy)-4,4-bis((triethylsilyloxy)methyl)pentanenitrile.

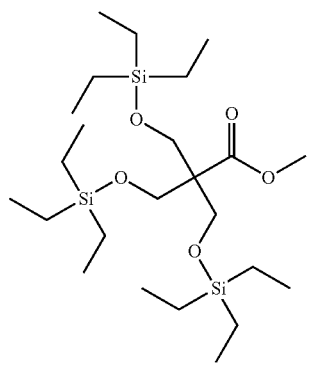

Step B: To a stirred solution of methyl 3-hydroxy-2,2-bis(hydroxymethyl)propanoate (1 equivalent) in pyridine at rt is added triethylsilyl chloride (3-6 equivalents) and the mixture is stirred at temperatures between rt and 60° C. until the reaction is substantially complete as monitored by LCMS or TLC. Water is added and the mixture is extracted with diethyl ether. The combined extracts are dried over magnesium sulfate, filtered, and concentrated under reduced pressure. The residue is purified by silica gel flash chromatography to afford methyl 3-(triethylsilyloxy)-2,2-bis((triethylsilyloxy)methyl)propanoate.

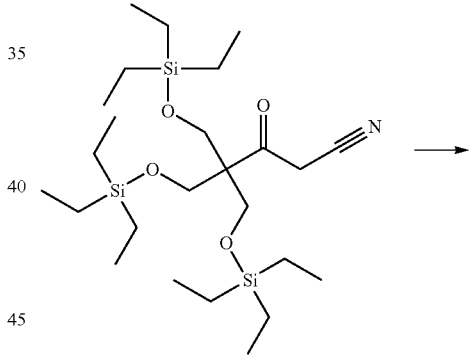

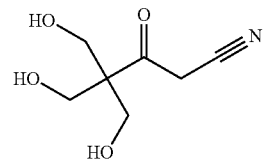

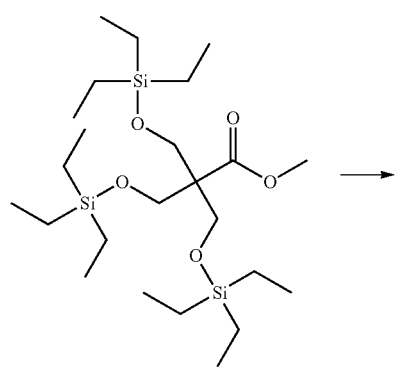

Step D: To a stirred solution of 3-oxo-5-(triethylsilyloxy)-4,4-bis((triethylsilyloxy)methyl)pentanenitrile (1 equivalent) in anhydrous THF at 0° C. is added tetrabutylammonium fluoride (1-5 equivalents) then stirring is continued at rt until the reaction is substantially complete as monitored by LCMS or TLC. Water is added followed by extraction with EtOAc. The combined organic layers are dried over magnesium sulfate, filtered, and concentrated under reduced pressure. The residue is purified by silica gel flash chromatography to afford 5-hydroxy-4,4-bis(hydroxymethyl)-3-oxopentanenitrile.

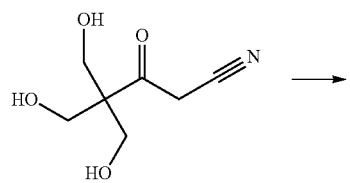
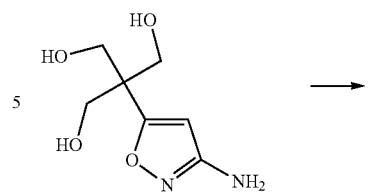
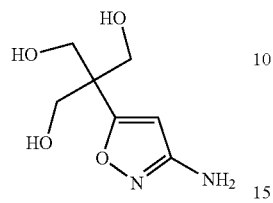
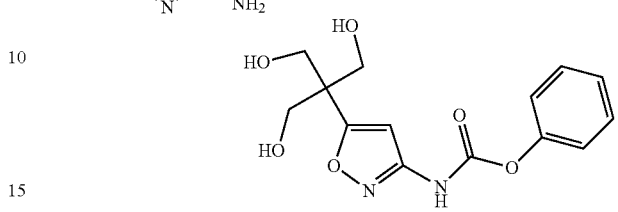

Step E: A mixture of 5-hydroxy-4,4-bis(hydroxymethyl)-3-oxopentanenitrile (1 equivalent) and sodium hydroxide (1.3 equivalents) in a mixture of water and EtOH is adjusted to pH 7.4-8 and heated at 60-100° C. After 10 to 22 h the mixture is acidified (pH≤1) with aq hydrochloric acid or aq sulfuric acid and heated for a further 2 to 5 h at 60-100° C. The mixture is concentrated under reduced pressure and the residue is partitioned between 30% aq sodium hydroxide and chloroform. The organic layer is separated and the aqueous layer is further extracted with chloroform. The combined organic layers are washed with water or brine then dried over magnesium sulfate, filtered, and concentrated under reduced pressure. The residue is purified by silica gel flash chromatography to afford 2-(3-aminoisoxazol-5-yl)-2-(hydroxymethyl)propane-1,3-diol.

Step F: To a stirred mixture of 2-(3-aminoisoxazol-5-yl)-2-(hydroxymethyl)propane-1,3-diol (1 equivalent) and potassium carbonate (2-5 equivalents) in anhydrous THF at rt is added phenyl chloroformate (1-2 equivalents), then stirring is continued at rt until the reaction is substantially complete as monitored by LCMS or TLC. The mixture is concentrated under reduced pressure and the residue is partitioned between water and dichloromethane. The organic layer is separated and the aqueous layer is further extracted with dichloromethane. The combined extracts are washed with water or brine, then dried over magnesium sulfate, filtered, and concentrated under reduced pressure. The residue is purified by silica gel flash chromatography to afford phenyl 5-(1,3-dihydroxy-2-(hydroxymethyl)propan-2-yl)isoxazol-3-ylcarbamate.

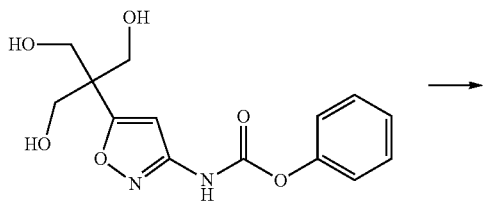

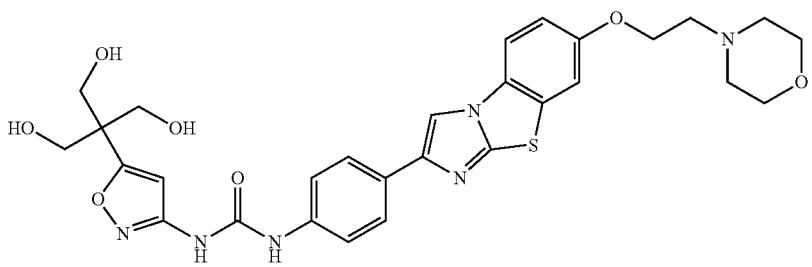

Step G: A mixture of phenyl 5-(1,3-dihydroxy-2-(hydroxymethyl)propan-2-yl)isoxazol-3-ylcarbamate (1 equivalent), 7-(2-morpholin-4-yl-ethoxy)-2-(4-aminophenyl)imidazo[2,1-b]benzothiazole (4) (1 equivalent) and 4-(dimethylamino)pyridine (0.05-0.5 equivalents) in anhydrous THF is stirred at a temperature between rt and 50° C. until the reaction is substantially complete as monitored by LCMS or TLC. The reaction mixture is concentrated under reduced pressure and the residue is purified by either preparative reverse-phase HPLC or silica gel flash chromatography to afford 1-[5-(2-hydroxy-1,1-bis-hydroxymethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1b).

Alternatively, a mixture of phenyl 5-(1,3-dihydroxy-2-(hydroxymethyl)propan-2-yl)isoxazol-3-ylcarbamate (1.1 equivalent), 7-(2-morpholin-4-yl-ethoxy)-2-(4-aminophenyl)imidazo[2,1-b]benzothiazole (4) (1 equivalent) and 4-(dimethylamino)pyridine (0.05-0.5 equivalents) in anhydrous DCM is stirred. To this reaction is added triethylamine (0.15 equivalent) and optionally, additional DCM and this mixture is then heated to reflux (~40° C.) until the reaction is substantially complete as monitored by LCMS, TLC or HPLC analysis.

Example 16

Preparation of 1-(5-tert-butyl-isoxazol-3-yl)-3-(4-{7-[2-(2-hydroxy-ethylamino)-ethoxy]-benzo[d]imidazo[2,1-b]thiazol-2-yl}-phenyl)-urea (I-2)

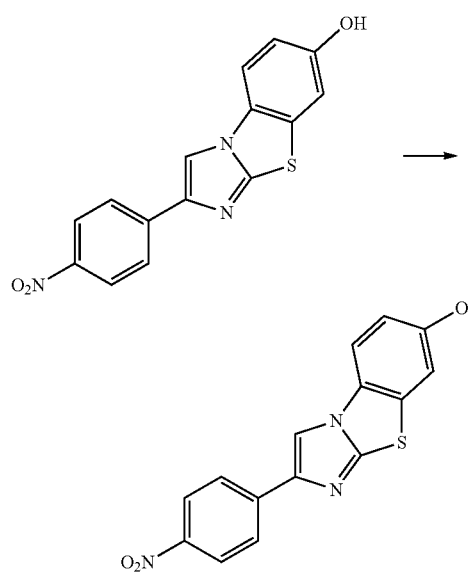

Step A: To a stirred solution of 2-(4-nitrophenyl)imidazo[2,2-b]benzothiazol-7-ol (2) (1 equivalent) in anhydrous DMF at rt are added potassium carbonate (2-3 equivalents) and 1-bromo-2-chloroethane (2-3 equivalents), and the mixture is stirred at a temperature between rt and 60° C. until the reaction is substantially complete as monitored by LCMS or TLC. The mixture is added to water and the resulting aqueous mixture is extracted with EtOAc. The organic layer is separated, dried over magnesium sulfate, filtered, and concentrated under reduced pressure. The residue is purified by silica gel flash chromatography to afford 7-(2-chloro-ethoxy)-2-(4-nitro-phenyl)-benzo[d]imidazo[2,1-b]thiazole.

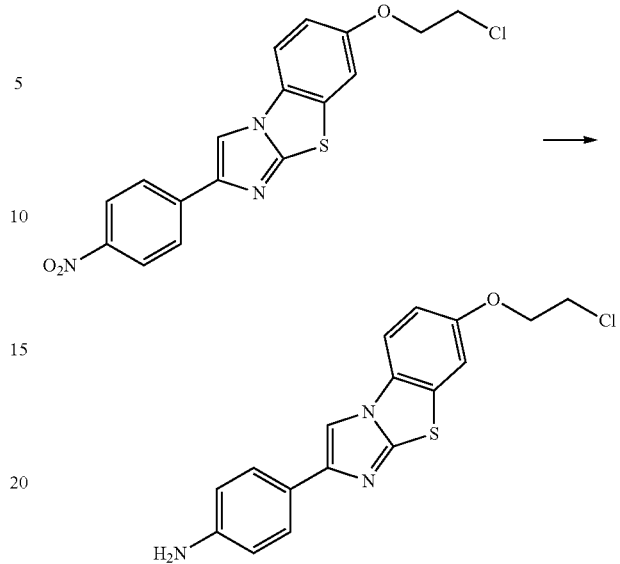

Step B: A mixture of 7-(2-chloro-ethoxy)-2-(4-nitro-phenyl)-benzo[d]imidazo[2,1-b]thiazole (1 equivalent) and 10% Pd/C (0.05-0.1 equivalents) in a mixture of MeOH and THF under 1 atmosphere of hydrogen gas is stirred at rt until the reaction is substantially complete as monitored by LCMS or TLC. The mixture is filtered through Celite and concentrated under reduced pressure. The residue is purified by silica gel flash chromatography to afford 7-(2-chloro-ethoxy)-2-(4-amino-phenyl)-benzo[d]imidazo[2,1-b]thiazole.

Alternatively, 7-(2-chloro-ethoxy)-2-(4-amino-phenyl)-benzo[d]imidazo[2,1-b]thiazole could be prepared in the following manner. A mixture of 7-(2-chloro-ethoxy)-2-(4-nitro-phenyl)-benzo[d]imidazo[2,1-b]thiazole (1 equivalent) and tin (II) chloride dihydrate (5-10 equivalents) in EtOH, is heated at 70 to 80° C. until the reaction is substantially complete as monitored by LCMS or TLC. The mixture is concentrated under reduced pressure and the residue is partitioned between saturated aq sodium hydrogen carbonate solution and EtOAc. If required, the biphasic mixture is filtered through Celite to remove emulsified by-products. The organic layer is separated and the aqueous layer is further extracted with EtOAc. The combined organic layers are washed with water or brine, dried over magnesium sulfate, filtered, and concentrated under reduced pressure. the residue is purified by silica gel flash chromatography to afford 7-(2-chloro-ethoxy)-2-(4-amino-phenyl)-benzo[d]imidazo[2,1-b]thiazole.

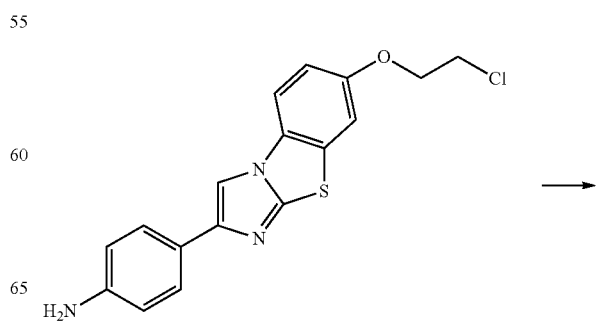

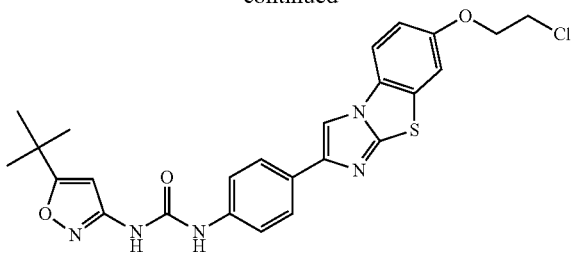

Step C: A mixture of 7-(2-chloro-ethoxy)-2-(4-amino-phenyl)-benzo[d]imidazo[2,1-b]thiazole (1 equivalent) and phenyl 5-tert-butylisoxazol-3-ylcarbamate, prepared as described in WO 2006/082404 A1 (1 equivalent) in anhydrous THF is stirred at selected temperatures between rt and 50° C. until the reaction is substantially complete as monitored by LCMS or TLC. The mixture is concentrated under reduced pressure and the residue is partitioned between water and either dichloromethane or a mixture of dichloromethane and isopropanol. The separated aqueous layer is further extracted with dichloromethane or a mixture of isopropanol and dichloromethane, and the combined organic layers are dried over magnesium sulfate, filtered, and concentrated under reduced pressure. The residue is purified by silica gel flash chromatography to afford 1-(5-tert-butyl-isoxazol-3-yl)-3-{4-[7-(2-chloro-ethoxy)-benzo[d]imidazo[2,1-b]thiazol-2-yl]-phenyl}-urea.

Alternatively, 1-(5-tert-butyl-isoxazol-3-yl)-3-{4-[7-(2-chloro-ethoxy)-benzo[d]imidazo[2,1-b]thiazol-2-yl]-phenyl}-urea could be prepared in the following manner. To a mixture of 7-(2-chloro-ethoxy)-2-(4-amino-phenyl)-benzo[d]imidazo[2,1-b]thiazole (1 equivalent) in anhydrous THF at 0° C. is added 5-tert-butyl-isoxazole-3-isocyanate (1-2 equivalents) and the mixture is stirred at selected temperatures between 0° C. and 50° C. until the reaction is substantially complete as monitored by LCMS or TLC. The mixture is treated with a mixture of water and MeOH, then partitioned between water and either dichloromethane or a mixture of dichloromethane and isopropanol. The organic layer is separated and the aqueous layer is further extracted with dichloromethane or a mixture of isopropanol and dichloromethane, and the combined organic layers are dried over magnesium sulfate, filtered, and concentrated under reduced pressure. The residue is purified by silica gel flash chromatography to afford 1-(5-tert-butyl-isoxazol-3-yl)-3-{4-[7-(2-chloro-ethoxy)-benzo[d]imidazo[2,1-b]thiazol-2-yl]-phenyl}-urea.

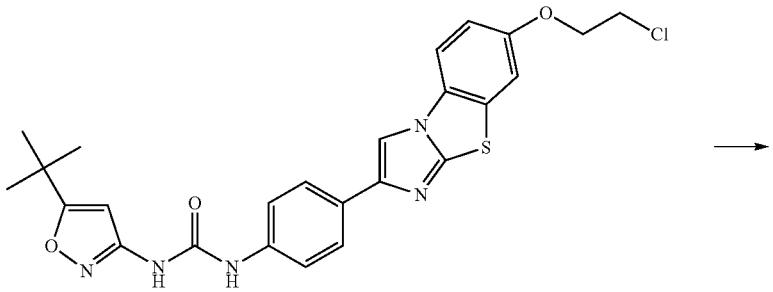

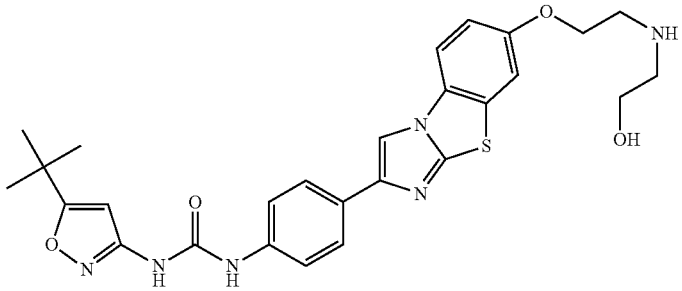

Step D: A mixture of 1-(5-tert-butyl-isoxazol-3-yl)-3-{4-[7-(2-chloro-ethoxy)-benzo[d]imidazo[2,1-b]thiazol-2-yl]-phenyl}-urea (1 equivalent), ethanolamine (1-3 equivalents), potassium carbonate (2-5 equivalents) and sodium iodide (2-5 equivalents) in anhydrous DMF is stirred at temperatures between rt and 80° C. until the reaction is substantially complete as monitored by LCMS or TLC. The mixture is partitioned between water and either dichloromethane or a mixture of isopropanol and dichloromethane. The separated aqueous layer is further extracted with dichloromethane or a mixture of isopropanol and dichloromethane, and the combined organic layers are washed with water or brine, then dried over magnesium sulfate, filtered, and concentrated under reduced pressure. The residue is purified by preparative reverse-phase HPLC or silica gel flash chromatography to afford 1-(5-tert-butyl-isoxazol-3-yl)-3-(4-{7-[2-(2-hydroxy-ethylamino)-ethoxy]-benzo[d]imidazo[2,1-b]thiazol-2-yl}-phenyl)-urea (I-2).

Example 17

Preparation of [2-(2-{4-[3-(5-tert-butyl-isoxazol-3-yl)-ureido]-phenyl}-benzo[d]imidazo[2,1-b]thiazol-7-yloxy)-ethylamino]-acetic acid (I-3)

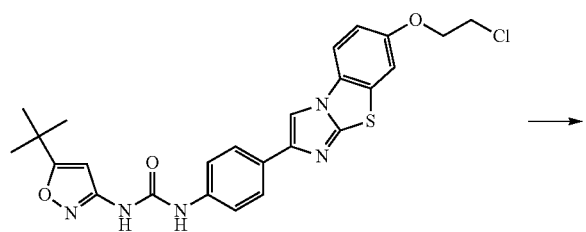

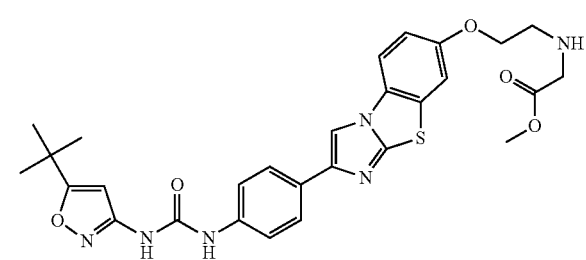

A mixture of 1-(5-tert-butyl-isoxazol-3-yl)-3-{4-[7-(2-chloro-ethoxy)-benzo[d]imidazo[2,1-b]thiazol-2-yl]-phenyl}-urea (1 equivalent), glycine ethyl ester hydrochloride (1-3 equivalents), potassium carbonate (2-6 equivalents), and sodium iodide (2-5 equivalents) in anhydrous DMF is stirred at selected temperatures between rt and 80° C. until the reaction is substantially complete as monitored by LCMS or TLC. The mixture is partitioned between water and either dichloromethane or a mixture of isopropanol and dichloromethane. The organic layer is separated and the aqueous layer is further extracted with dichloromethane or a mixture of isopropanol and dichloromethane. The combined extracts are washed with water or brine, then dried over magnesium sulfate, filtered, and concentrated under reduced pressure. The residue is purified by silica gel flash chromatography to afford [2-(2-{4-[3-(5-tert-butyl-isoxazol-3-yl)-ureido]-phenyl}-benzo[d]imidazo[2,1-b]thiazol-7-yloxy)-ethylamino]-acetic acid methyl ester.

Alternatively, [2-(2-{4-[3-(5-tert-butyl-isoxazol-3-yl)-ureido]-phenyl}-benzo[d]imidazo[2,1-b]thiazol-7-yloxy)-ethylamino]-acetic acid methyl ester is prepared in the following manner. To a stirred mixture of 1-(5-tert-butyl-isoxazol-3-yl)-3-{4-[7-(2-chloro-ethoxy)-benzo[d]imidazo [2,1-b]thiazol-2-yl]-phenyl}-urea (1 equivalent), glycine ethyl ester hydrochloride (1-3 equivalents) and potassium carbonate (2-6 equivalents) in anhydrous acetone is added tetrabutylammonium iodide (0.1-1 equivalent) and the mixture is stirred and heated under reflux until the reaction is substantially complete as monitored by LCMS or TLC. The mixture is partitioned between water and either dichloromethane or a mixture of isopropanol and dichloromethane. The organic layer is separated and the aqueous layer is further extracted with dichloromethane or a mixture of isopropanol and dichloromethane. The combined extracts are washed with water or brine, then dried over magnesium sulfate, filtered, and concentrated under reduced pressure. The residue is purified by silica gel flash chromatography to afford [2-(2-{4-[3-(5-tert-butyl-isoxazol-3-yl)-ureido]-phenyl}-benzo[d]imidazo[2,1-b]thiazol-7-yloxy)-ethylamino]-acetic acid methyl ester.

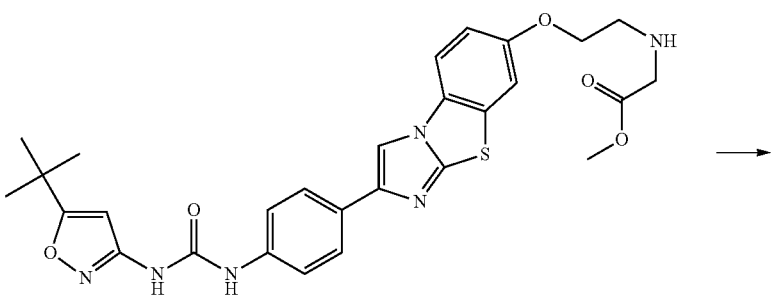

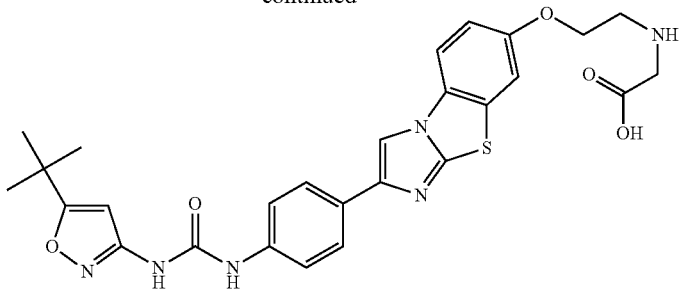

Step B: A mixture of [2-(2-{4-[3-(5-tert-butyl-isoxazol-3-yl)-ureido]-phenyl}-benzo[d]imidazo[2,1-b]thiazol-7-yloxy)-ethylamino]-acetic acid methyl ester (1 equivalent) and lithium hydroxide monohydrate (3-6 equivalents) in 50% aq THF is stirred at selected temperatures between rt and 60° C. until the reaction is substantially complete as monitored by LCMS or TLC. The reaction mixture is neutralized with aq hydrochloric acid and partitioned between water and either dichloromethane or a mixture of isopropanol and dichloromethane. The organic layer is separated and the aqueous layer is further extracted with dichloromethane or a mixture of isopropanol and dichloromethane. The combined organic layers are dried over magnesium sulfate, filtered, and concentrated under reduced pressure. The residue is purified by preparative reverse-phase HPLC or silica gel flash chromatography to afford [2-(2-{4-[3-(5-tert-butyl-isoxazol-3-yl)-ureido]-phenyl}-benzo[d]imidazo[2,1-b]thiazol-7-yloxy)-ethylamino]-acetic acid (I-3).

Example 18

Preparation of 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a)

Step A: A mixture of 1-[5-(2-hydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1) (1 equivalent) and Dess-Martin periodinane (1-1.5 equivalents) in anhydrous dichloromethane is stirred at rt until the reaction is substantially complete as monitored by LCMS or TLC. The mixture is filtered through Celite and the filtrate is concentrated under reduced pressure. The residue is purified by silica gel flash chromatography to afford 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a).

Alternatively, 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a) is prepared in the following manner. To a stirred mixture of dimethyl sulfoxide (1 equivalent) in anhydrous dichloromethane at −78° C. under an argon atmosphere is added dropwise oxalyl chloride (0.5 equivalents). After stirring for a further 20 to 40 min, compound 1-[5-(2-hydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1) (0.3 equivalents) is added and the mixture is stirred at −78° C. Triethylamine (1-2 equivalents) is added, and the mixture is allowed to warm to

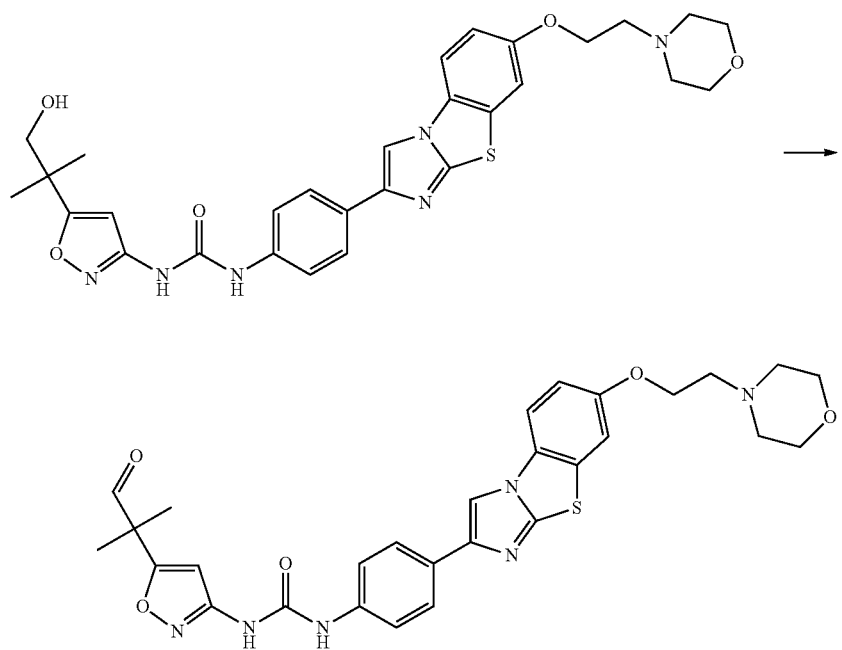 [SMILES: CC(C)(C=O)c1cc(NC(=O)Nc2ccc(-c3cn4c(n3)sc3cc(OCCN5CCOCC5)ccc34)cc2)no1 ; CC(C)(C(=O)O)c1cc(NC(=O)Nc2ccc(-c3cn4c(n3)sc3cc(OCCN5CCOCC5)ccc34)cc2)no1]

rt, then the mixture is filtered through Celite and concentrated under reduced pressure. The residue is purified by silica gel flash chromatography to afford 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a).

Example 19

Preparation of 1-[5-(2,2-dihydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-4)

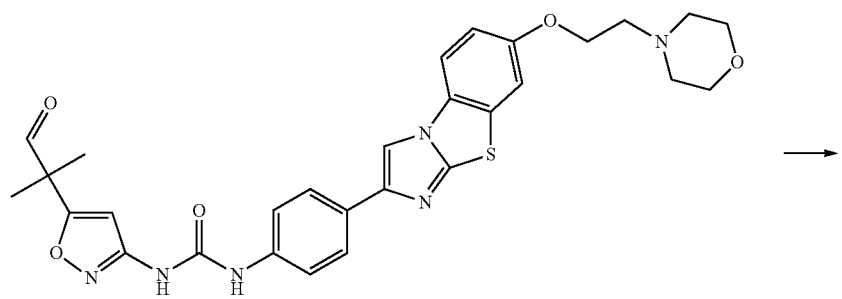

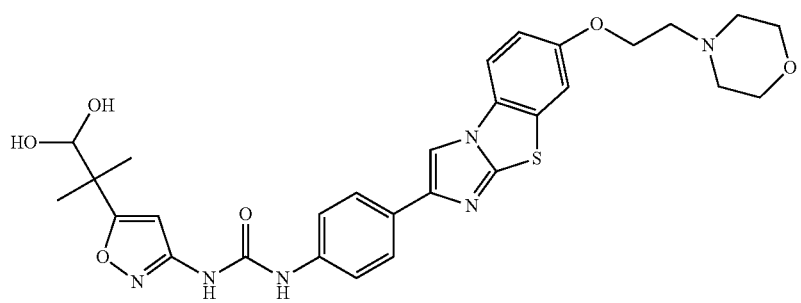

Step A: 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a) is dissolved in aqueous solution, whereupon an equilibrating mixture of 1-[5-(2,2-dihydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-4) and 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a) is formed over time. 1-[5-(2,2-dihydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-4) is used without isolation.

Example 20

Preparation of 2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propionic acid (I-5)

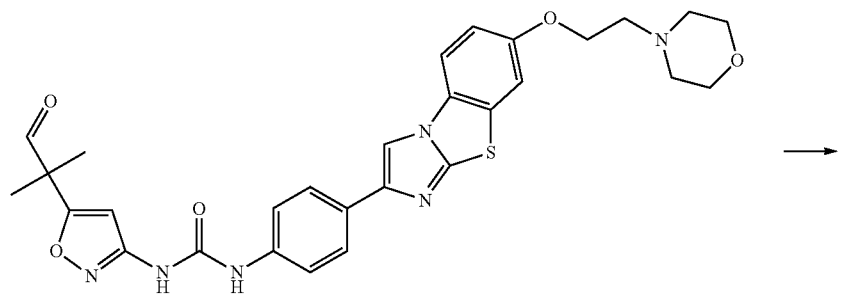

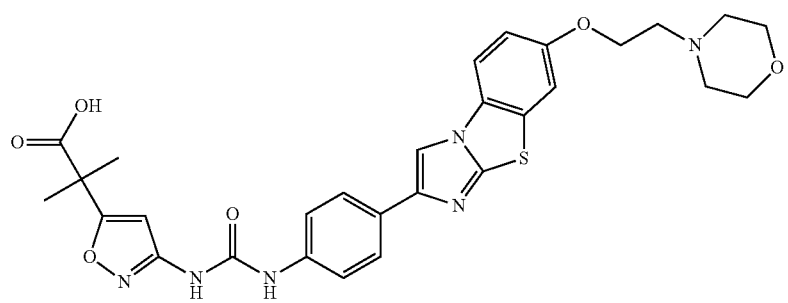

Step A: 2-Methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propionic acid (I-5) is prepared by following a general procedure given in J. Org. Chem. 2002, 67, 411. To a stirred solution of 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a) (1 equivalent) in a 5:1 mixture of tert-butanol and water at rt are added sequentially dihydrogen sodium phosphate (3 equivalents), 2-methyl-2-butene (6 equivalents), and sodium chlorite (1 to 1.5 equivalents) and the mixture is stirred at rt until the reaction is substantially complete as monitored by LCMS or TLC. The mixture is concentrated under reduced pressure and the residue is partitioned between water and either dichloromethane or a mixture of isopropanol and dichloromethane. The separated aqueous layer is further extracted with dichloromethane or a mixture of isopropanol and dichloromethane. The combined organic layers are washed with water or brine, dried over magnesium sulfate, filtered, and concentrated under reduced pressure. The residue is purified by preparative reverse-phase HPLC or silica gel flash chromatography to afford 2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propionic acid (I-5).

Alternatively final compound 2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propionic acid (I-5) is prepared by following a general procedure given in US 2005/0070549 A1. To a stirred solution of 1-[5-(1,1-dimethyl-2-oxo-ethyl)-isoxazol-3-yl]-3-{4-[7-(2-morpholin-4-yl-ethoxy)-benzo[d]imidazo[2,1-b]thiazol-2-yl]-phenyl}-urea (I-4a) (1 equivalent) in a mixture of acetic acid and water at rt is added a solution of amidosulfuric acid (1.5 equivalents) and sodium chlorite (1.5 equivalents) in water, and the mixture is stirred at rt until the reaction is substantially complete as monitored by LCMS or TLC. The mixture is neutralized with 30% aq sodium hydroxide and partitioned between water and either dichloromethane or a mixture of isopropanol and dichloromethane. The separated aqueous layer is further extracted with dichloromethane or a mixture of isopropanol and dichloromethane, and the combined organic layers are washed with water or brine dried over magnesium sulfate, filtered, and concentrated under reduced pressure. The residue is purified by preparative reverse-phase HPLC or silica gel flash chromatography to afford 2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propionic acid (I-5).

Example 21

Preparation of 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6)

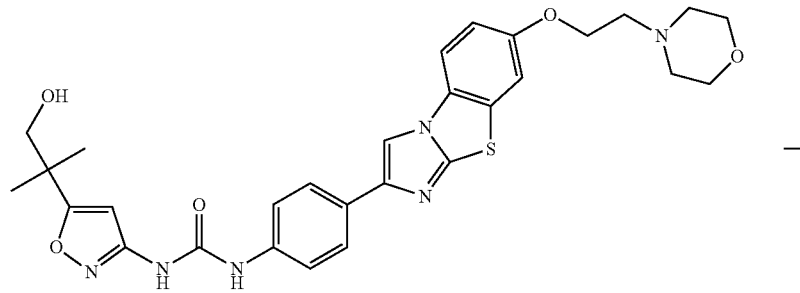

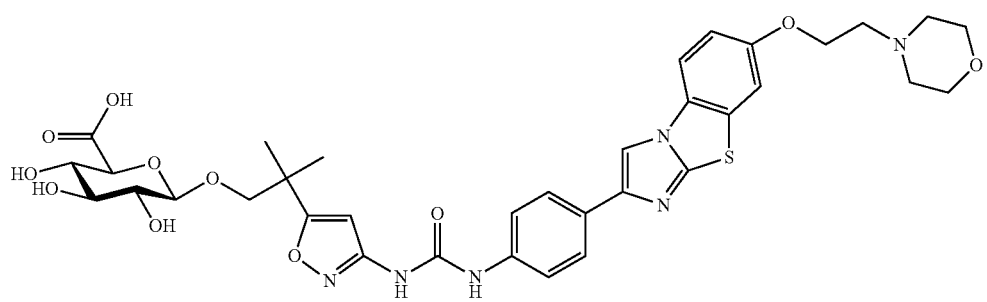

Step A: 3,4,5-Trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6) is prepared by following a general procedure given in Org. Lett. 2008, 10, 1585. To a stirred mixture of 1-[5-(2-hydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1) (1 equivalent), 1-deoxy-1-fluoro-α-D-glucopyranuronic acid ammonium salt, prepared as described in Org. Lett. 2008, 10, 1585 (1.2 equivalents) in 50 mM sodium phosphate buffer (pH=7.5) at rt, is added E. coli. E504G β-glucuronylsynthase (final concentration 0.1-0.2 mg/mL) or E. coli. E504A β-glucuronylsynthase (final concentration 0.1-0.2 mg/mL) and the mixture is stirred at rt for 4 days. Lyophilization of the mixture and purification of the residue by preparative reverse-phase HPLC or silica gel flash chromatography affords 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6).

Alternatively, 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6) is prepared by following an alternative general procedure given in Org. Lett. 2008, 10, 1585. To a stirred mixture of 1-[5-(2-hydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1) (1 equivalent) in a mixture of dimethyl sulfoxide (final volume 12.5-25% v/v) and 50 mM sodium phosphate buffer (pH=7.5) at rt, is added a solution of 1-deoxy-1-fluoro-α-D-glucopyranuronic acid ammonium salt (prepared as described in Org. Lett. 2008, 10, 1585) (1.2 equivalents) in 50 mM sodium phosphate buffer (pH=7.5). To this mixture is added E. coli. E504G β-glucuronylsynthase (final concentration 0.1-0.2 mg/mL) or E. coli. E504A β-glucuronylsynthase (final concentration 0.1-0.2 mg/mL) and the mixture is stirred at rt for 4 days. Lyophilization of the mixture and purification of the residue by preparative reverse-phase HPLC or silica gel flash chromatography affords 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6).

Alternatively, 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6) is prepared in the following manner.

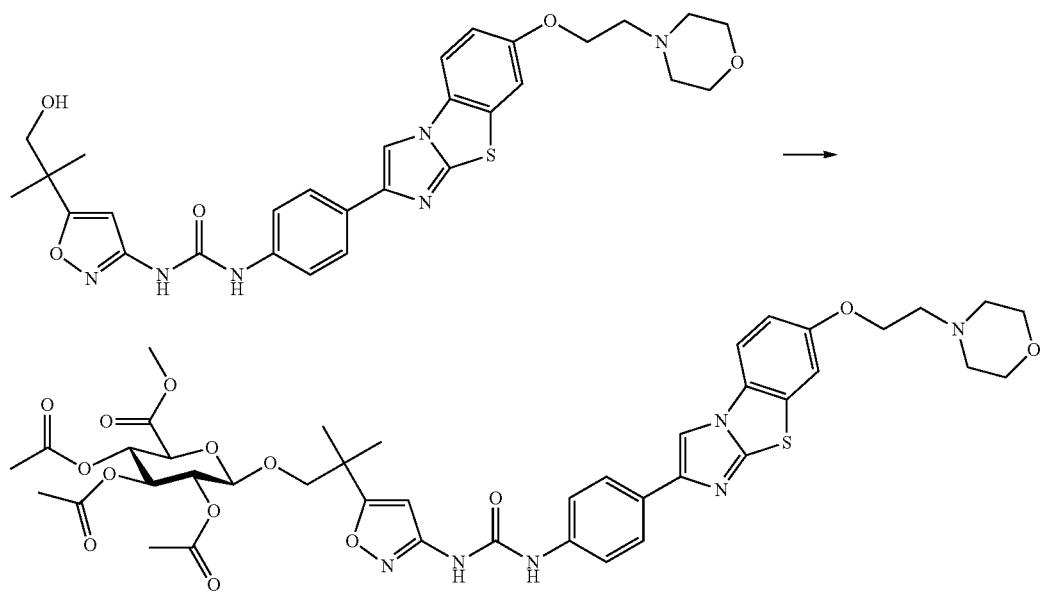

Step A: To a stirred mixture of 1-[5-(2-hydroxy-1,1-dimethyl-ethyl)-isoxazol-3-yl]-3-{4-[7-(2-morpholin-4-yl-ethoxy)-benzo[d]imidazo[2,1-b]thiazol-2-yl]-phenyl}-urea (I-1) (1 equivalent) and silver carbonate (0.5-1 equivalent) in toluene at rt is added 1-bromo-2,3,4-tri-O-acetyl-α-D-glucuronic acid methyl ester (0.8-1.5 equivalents) and the mixture is stirred at rt until the reaction is substantially complete as monitored by LCMS or TLC. The mixture is filtered and the filtrate is partitioned between water and either dichloromethane or a mixture of dichloromethane and isopropanol. The separated aqueous layer is further extracted with dichloromethane or a mixture of dichloromethane and isopropanol. The combined organic layers are washed with 2N aq sodium hydroxide dried over magnesium sulfate, filtered, and concentrated under reduced pressure. The residue is purified by preparative reverse-phase HPLC or silica gel flash chromatography to afford 3,4,5-triacetoxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid methyl ester.

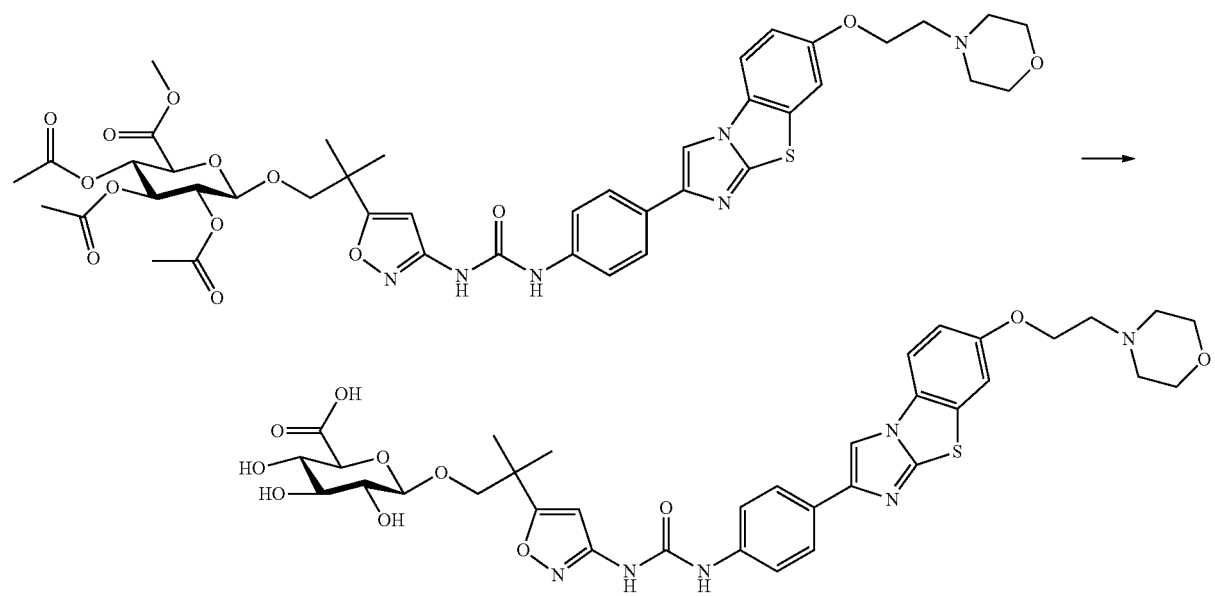

Step B: Final compound 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6) is prepared by following a general procedure given in *J. Med. Chem.* 1995, 38, 1911). To a stirred mixture of 3,4,5-triacetoxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid methyl ester (1 equivalent) in 4:1 MeOH:water at rt, is added dropwise aq potassium hydroxide (1-4 equivalents) and the mixture is stirred at rt until the reaction is substantially complete as monitored by LCMS or TLC. The mixture is acidified with glacial acetic acid and concentrated under reduced pressure. The residue is purified by preparative reverse-phase HPLC or silica gel flash chromatography to afford 3,4,5-trihydroxy-6-{2-methyl-2-[3-(3-{4-[7-(2-morpholin-4-yl-ethoxy)-benzo[d]imidazo[2,1-b]thiazol-2-yl]-phenyl}-ureido)-isoxazol-5-yl]-propoxy}-tetrahydro-pyran-2-carboxylic acid (I-6).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound having formula

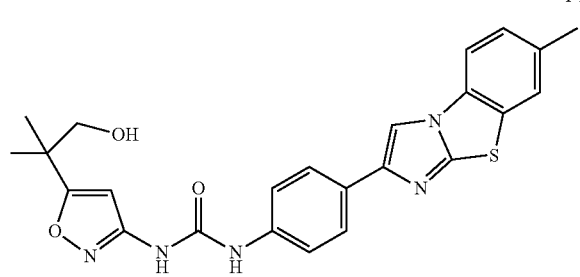

I-1

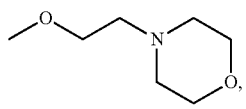

or a pharmaceutically acceptable salt or solvate thereof.

2. The compound of claim 1, wherein the compound is a purified compound.

3. The compound of claim 1 in a solid form.

4. A pharmaceutical composition comprising a therapeutically effective amount of a compound of claim 1 and a pharmaceutically acceptable carrier, excipient or diluent.

5. The composition according to claim 4 further comprising a second therapeutic agent selected from a chemotherapeutic agent, an anti-proliferative agent, an anti-inflammatory agent, an immunomodulatory agent, an immunosuppressive agent or an anti-emetic agent.

* * * * *